United States Patent
Barhoumi et al.

(10) Patent No.: US 11,597,925 B2
(45) Date of Patent: Mar. 7, 2023

(54) PEPTIDE NUCLEIC ACID CONJUGATES

(71) Applicant: Ventana Medical Systems, Inc., Tucson, AZ (US)

(72) Inventors: Aoune Barhoumi, Oro Valley, AZ (US); Rui Hong, Oro Valley, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 226 days.

(21) Appl. No.: 16/438,088

(22) Filed: Jun. 11, 2019

(65) Prior Publication Data

US 2020/0095577 A1    Mar. 26, 2020

Related U.S. Application Data

(63) Continuation of application No. PCT/US2017/066976, filed on Dec. 18, 2017.

(60) Provisional application No. 62/436,189, filed on Dec. 19, 2016.

(51) Int. Cl.
| | |
|---|---|
| *C07H 21/04* | (2006.01) |
| *C12N 15/11* | (2006.01) |
| *C07K 2/00* | (2006.01) |
| *C07K 14/00* | (2006.01) |
| *C07K 16/28* | (2006.01) |
| *G01N 33/53* | (2006.01) |
| *G01N 33/58* | (2006.01) |
| *G01N 33/68* | (2006.01) |

(52) U.S. Cl.
CPC .............. *C12N 15/111* (2013.01); *C07K 2/00* (2013.01); *C07K 14/003* (2013.01); *C07K 16/28* (2013.01); *G01N 33/5308* (2013.01); *G01N 33/582* (2013.01); *G01N 33/6857* (2013.01); *C12N 2310/113* (2013.01); *C12N 2310/3511* (2013.01); *C12N 2310/3513* (2013.01); *C12N 2310/3517* (2013.01); *C12N 2310/52* (2013.01)

(58) Field of Classification Search
CPC ..................... C12N 15/113; C07K 14/003
See application file for complete search history.

(56) References Cited

U.S. PATENT DOCUMENTS

| | | | |
|---|---|---|---|
| 5,527,675 A | 6/1996 | Coull et al. | |
| 5,539,082 A | 7/1996 | Nielsen et al. | |
| 5,623,049 A | 4/1997 | Löbberding et al. | |
| 5,650,327 A | 7/1997 | Copeland et al. | |
| 5,654,200 A | 8/1997 | Copeland et al. | |
| 5,714,331 A | 2/1998 | Buchardt et al. | |
| 5,736,336 A | 4/1998 | Buchardt et al. | |
| 5,773,571 A | 6/1998 | Nielsen et al. | |
| 5,786,571 A | 7/1998 | Bethel et al. | |
| 6,133,438 A | 10/2000 | Engstrom et al. | |
| 6,296,809 B1 | 10/2001 | Richards et al. | |
| 6,352,861 B1 | 3/2002 | Copeland et al. | |
| 6,670,113 B2 | 12/2003 | Hainfeld | |
| 6,827,901 B2 | 12/2004 | Copeland et al. | |
| 6,943,029 B2 | 9/2005 | Copeland et al. | |
| 8,592,219 B2 | 11/2013 | Kange et al. | |
| 2003/0211630 A1 | 11/2003 | Richards et al. | |
| 2004/0052685 A1 | 3/2004 | Richards et al. | |
| 2004/0265922 A1 | 12/2004 | Bieniarz et al. | |
| 2005/0003777 A1 | 1/2005 | Demir et al. | |
| 2006/0192283 A1 | 8/2006 | Benson | |
| 2006/0246524 A1 | 11/2006 | Bauer et al. | |
| 2007/0010014 A1 | 1/2007 | Wood et al. | |
| 2007/0241061 A1 | 10/2007 | Engstrom et al. | |
| 2008/0227742 A1 | 9/2008 | Dmochowski et al. | |
| 2010/0105030 A1 | 4/2010 | Lohse et al. | |
| 2011/0116972 A1 | 5/2011 | Holmquist et al. | |
| 2011/0195524 A1 | 8/2011 | Inganas et al. | |
| 2013/0260379 A1 | 10/2013 | Alexander et al. | |
| 2014/0178169 A1 | 6/2014 | Hebert et al. | |

FOREIGN PATENT DOCUMENTS

| | | | |
|---|---|---|---|
| CN | 104031129 A | 9/2014 | |
| CN | 106163570 A | 11/2016 | |
| CN | 107429247 A | 12/2017 | |
| JP | 2011505549 A | 2/2011 | |
| WO | 1999041273 A2 | 8/1999 | |
| WO | WO 99/41273 | * 8/1999 | ........... C12N 15/113 |
| WO | 2006022639 A1 | 3/2006 | |
| WO | 2007015168 A2 | 2/2007 | |
| WO | 2009067009 A1 | 5/2009 | |
| WO | 2011049608 A2 | 4/2011 | |
| WO | 2014200767 A1 | 12/2014 | |
| WO | 2015112438 A1 | 7/2015 | |
| WO | 2016172346 A1 | 10/2016 | |

OTHER PUBLICATIONS

Leonidova et al. (Chem. Sci., 2015, 6, 5601-5616).*
Liu et al. (Eur J Nucl Med Mol Imaging, 2009, 36, 1296-1307).*
Adamczyk, M. et al., Bioconjugate Chem. 1999, 10, 1032-1037.
Jeanson, et al., Journal of Immunological Methods, 111 (1988), 261-270.
Vira, S, et al., Analytical Biochemistry 402 (2010), 146-150.
Pearson, J.E., et al., Journal of Immunological Methods 221 (1998), 87-94.
Leonidova_Chem Sci pp. 5601-5616 In vivo demonstration of an active tumor pretargeting approach with peptide nucleic acid bioconjugates as complementary system Chem. Sci. Leonidova, A. et al. vol. 6, No. 10 (2015) Non-Patent Reference.
Liu et al., Eur J Nucl med Mol Imaging, 2009, 36, pp. 1296-1307 Noninvasive imaging of tumor integrin expression using 18F-labeled RDG dimer peptide with PEG4 linkers Eur J Nucl Med Mol Imaging Liu, Zhaofei et al. 36 2009 Non-Patent Reference.

(Continued)

*Primary Examiner* — Amy H Bowman
(74) *Attorney, Agent, or Firm* — Charney IP Law LLC; Thomas M. Finetti

(57) ABSTRACT

The disclosure is directed to conjugates, e.g. PNA conjugates, as well as methods of employing the conjugates for detecting one or more targets in a biological sample, e.g. a tissue sample.

12 Claims, 32 Drawing Sheets
(19 of 32 Drawing Sheet(s) Filed in Color)
Specification includes a Sequence Listing.

(56) References Cited

OTHER PUBLICATIONS

Sahu_Journal of Organic Chemistry pp. 5614-5627 Synthesis and Characterization of Conformationally Preorganized, (R)-Diethylene Glycol-Containing γ-Peptide Nucleic Acids with Superior Hybridization Properties and Water Solubility J Org Chem Sahu, B, et al. vol. 76 Issue 14 (2011) Non-Patent Reference.

A simple and effective cleavable linker for chemical proteomics applications, Mol Cell Proteomics, Jan. 2013; 12 (1):237-44. doi: 10.1074/mcp.M112.021014. Epub Oct. 1, 2012.

"Peptide nucleic acid characterization by MALDI-TOF mass spectrometry," Anal Chem. Sep. 15, 1996;68(18):3283-7.

Molecular Probes Handbook—A Guide to Fluorescent Probes and Labeling Technologies, Molecular Probes, Eugene, OR, TheroFisher Scientific, 11th Edition.

Sambrook et al., Molecular Cloning: A Laboratory Manual, Cold Spring Harbor Laboratory Press (1989) and Ausubel el al., Current Protocols in Molecular Biology, Greene Publishing Associates and Wiley-Intersciences (1987), the disclosures of which are incorporated herein by reference.

Adamczyk M, et al., 1999, Bioconjug Chem; Jeanson A, et al., 1988, J Immunol Methods; Vira S, et al., 2010, Anal Biochem; Pearson JE et al., 1998, J Immunol Methods.

Sadu, Synthesis and Characterization of Conformationally Preorganized, (R)-Diethylene Glycol-Containing γ-Peptide Nucleic Acids with Superior Hybridization Properties and Water Solubility, J. Org. Chem. 2011, 76, 5614-5627.

Cao, Quantum dots high fluorescent signal amplification immunoassay using branched DNA and peptide nucleic acid conjugated antibody, Electronic Supplementary Material (ESI) for Analyst, The Royal Society of Chemistry 2011.

Dickgiesser, Self-Assembled Hybrid Aptamer-Fc Conjugates for Targeted Delivery: A Modular Chemoenzymatic Approach, ACS Chem. Biol. 2015, 10, 2158-2165.

Englund, gamma-Substituted Peptide Nucleic Acids Constructed from l-Lysine are a Versatile Scaffold for Multifunctional Display, Angew. Chem. Int. Ed. 2007, 46, 1414-1418.

Kazane, Self-Assembled Antibody Multimers through Peptide Nucleic Acid Conjugation, J. Am. Chem. Soc. 2013, 135, 340-346.

Sadu, Detection of miRNA in Live Cells by Using Templated Ru II-Catalyzed Unmasking of a Fluorophore, Chem. Eur. J. 2013, 19, 8182-8189.

Rozners, "Recent Advances in ChemicalModification of Peptide Nucleic Acids," Hindawi Publishing Corporation Journal of Nucleic Acids, vol. 2012, Article ID 518162, 8 pages, doi:10.1155/2012/518162.

\* cited by examiner

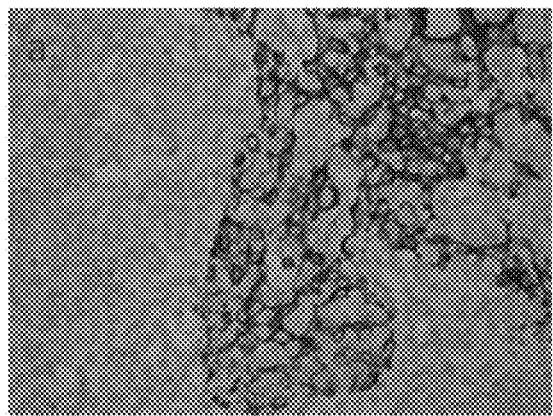
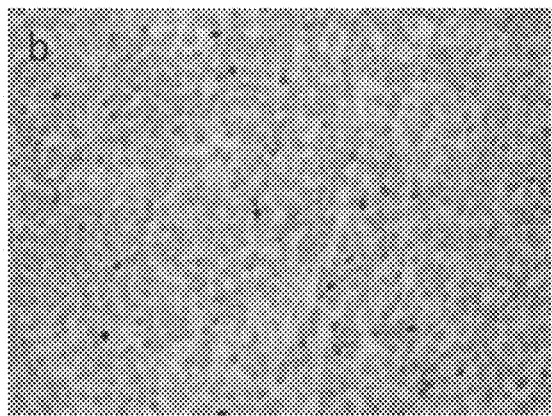
FIG. 4A                 FIG. 4B
FIG. 5A                 FIG. 5B
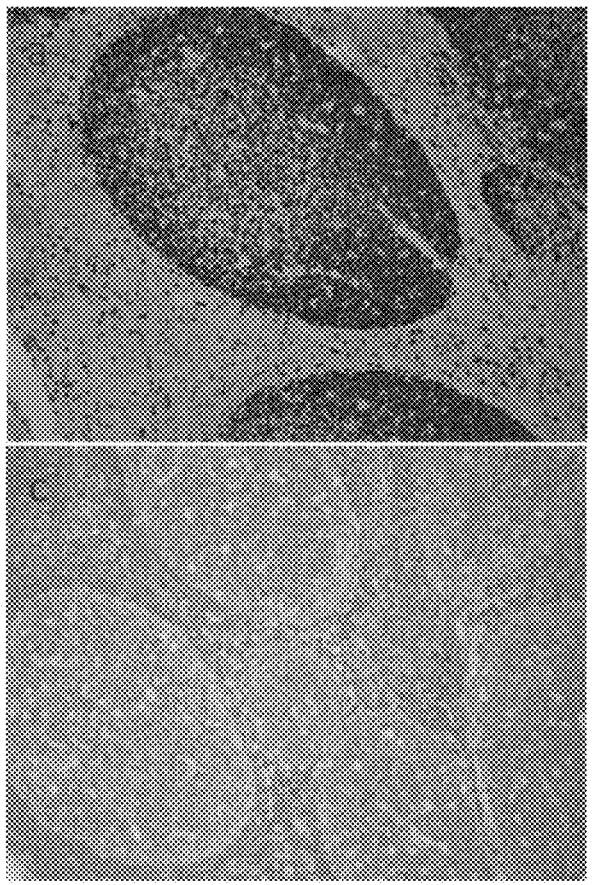
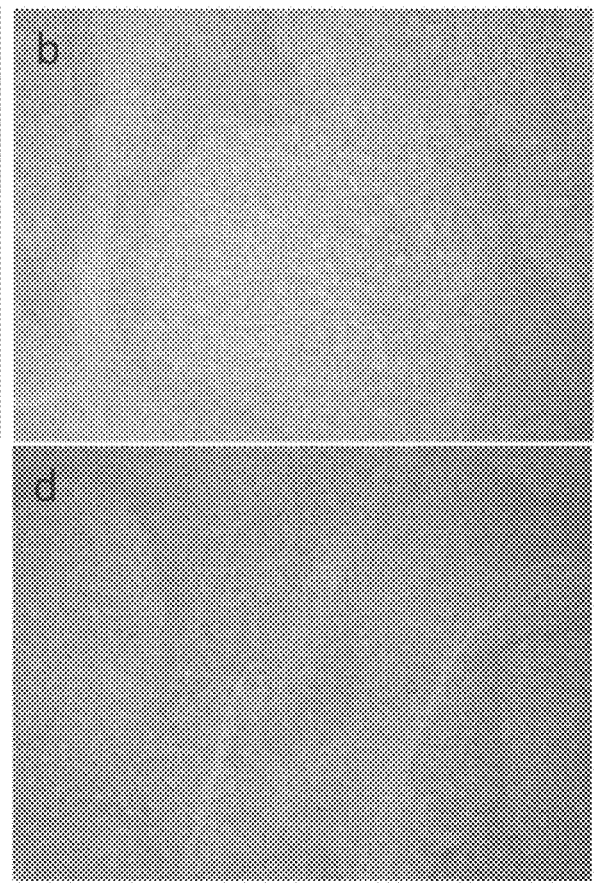
FIG. 5C                 FIG. 5D

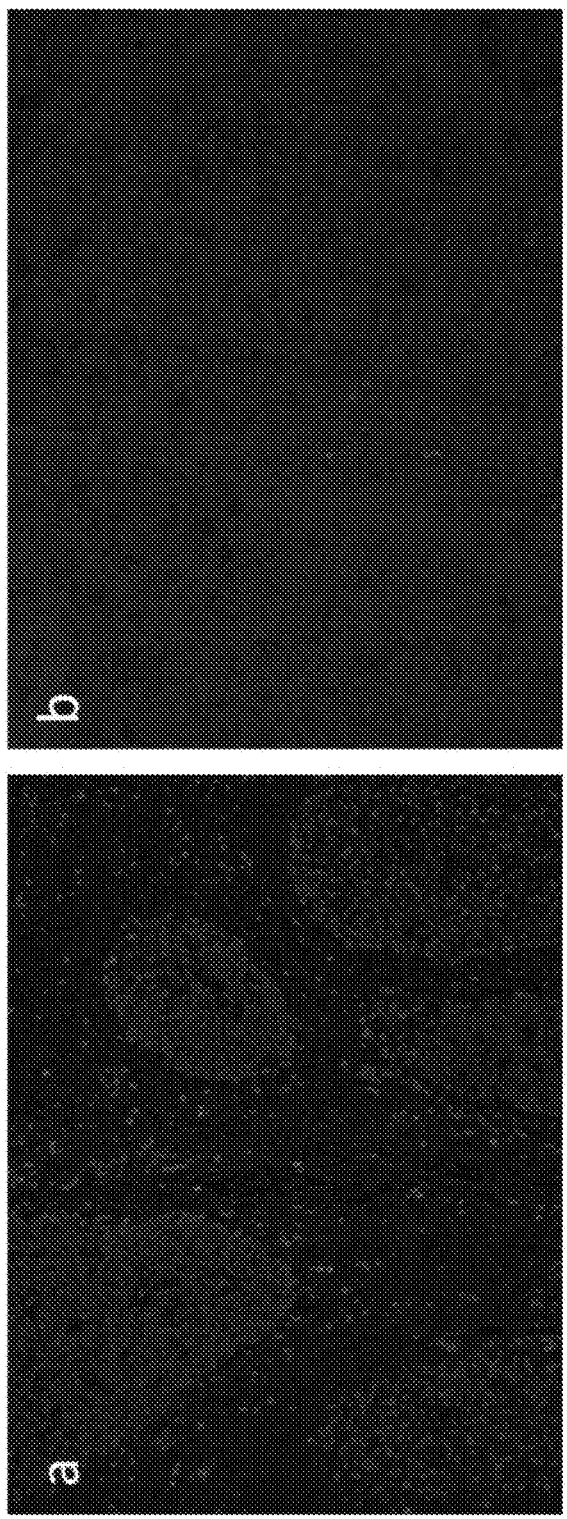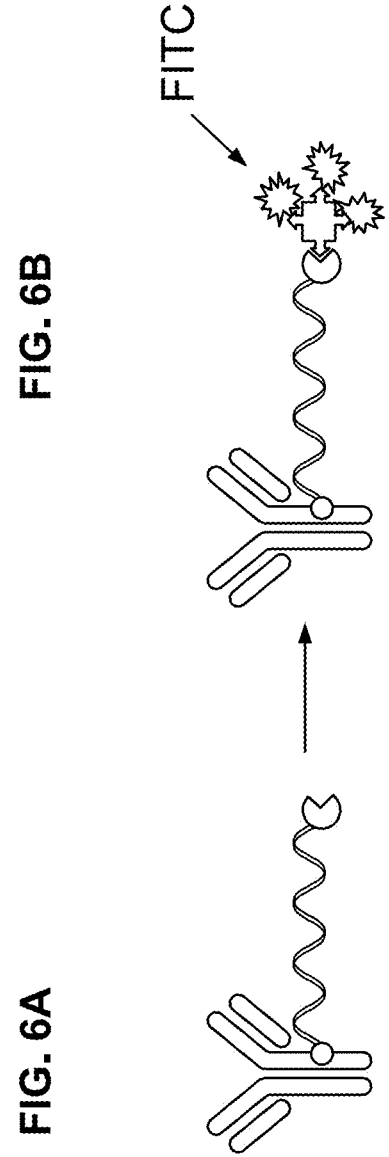
FIG. 6A  FIG. 6B  FIG. 6C

FIG. 8A FIG. 8B
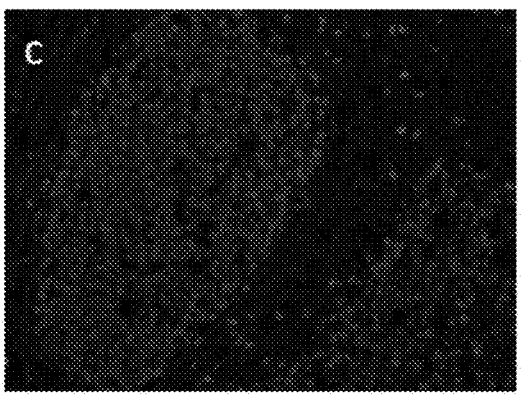
FIG. 8C FIG. 8D
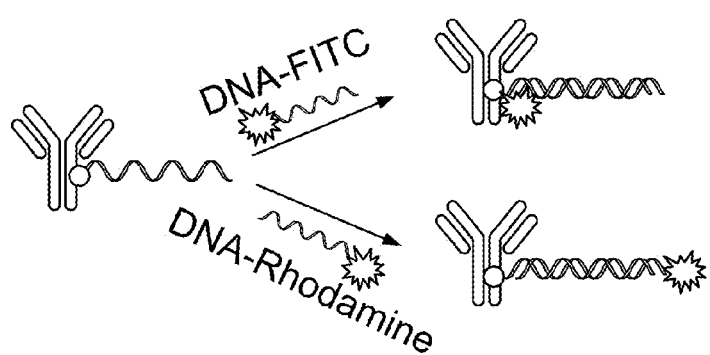
FIG. 8E

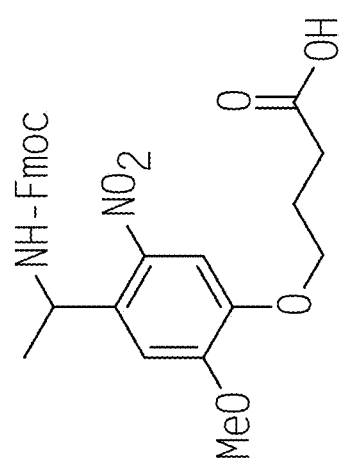
FIG. 11
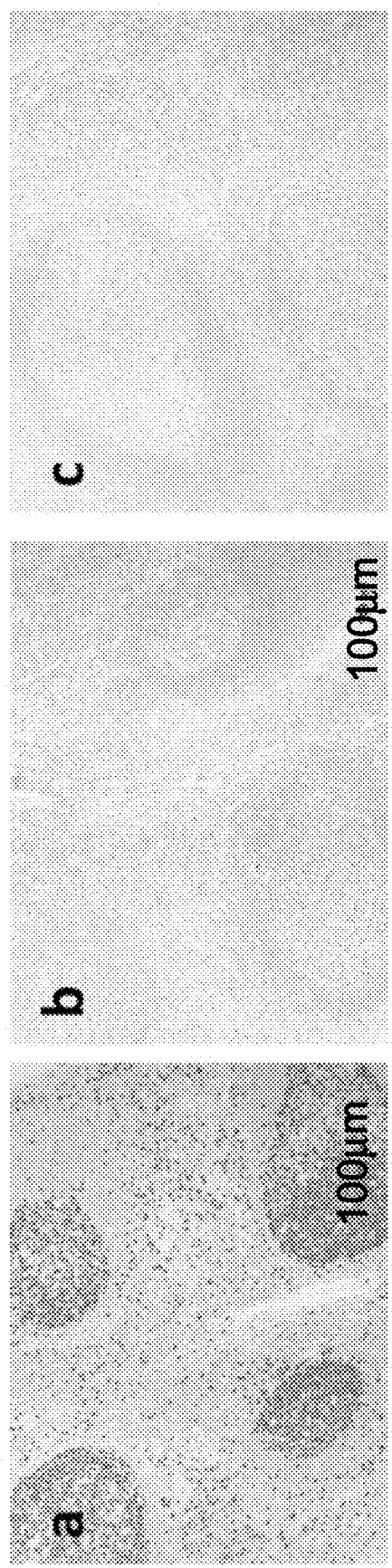
FIG. 12A 0 Min
FIG. 12B 5 Min
FIG. 12C 10 Min

Tonsil/CD45/GAM-PNA/SA-HRP

Tonsil/Ki67/GAR-PNA/SA-HRP

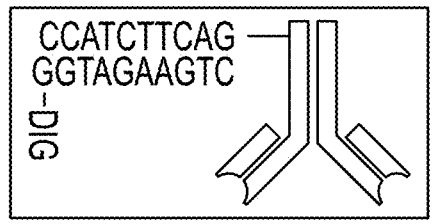
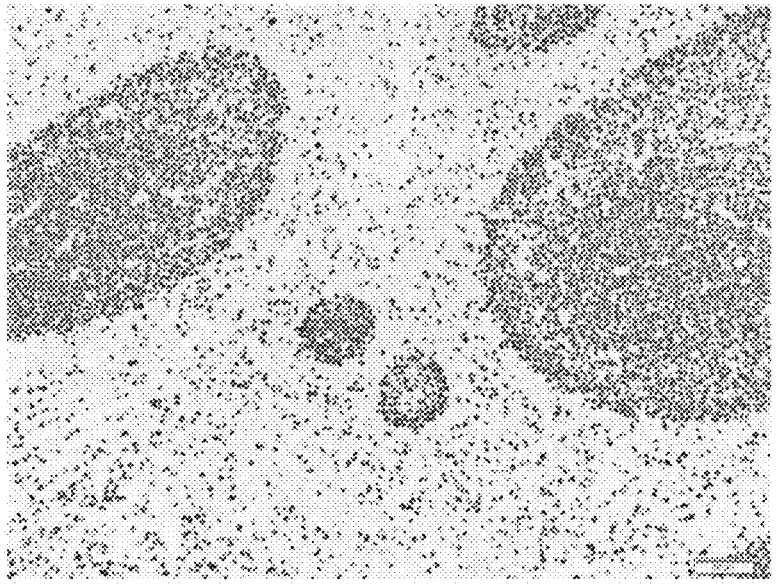
Tonsil_Ki67_GAR-sPNA_AB14_xDIG-HRP
5 uM
FIG. 25A
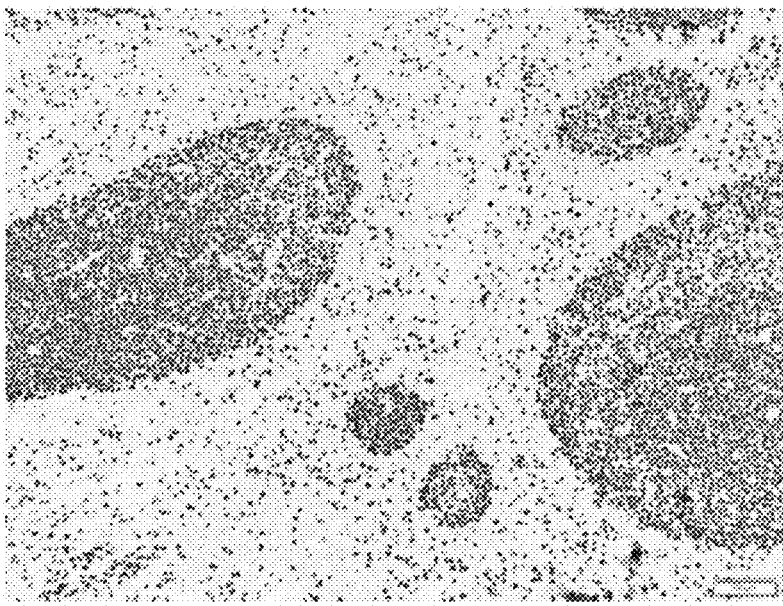
Tonsil_Ki67_GAR-sPNA_AB14_xDIG-HRP
10 uM
FIG. 25B

PEPTIDE NUCLEIC ACID CONJUGATES

CROSS REFERENCE TO RELATED APPLICATIONS

MOO II The present application is a continuation of International Application No. PCT/US2017/066976 filed on Dec. 18, 2017, which application claims the benefit of the filing date of U.S. Provisional Patent Application 62/436,189 filed Dec. 19, 2016, the disclosure of which are hereby incorporated by reference herein in their entireties.

FIELD OF THE SUBJECT DISCLOSURE

The present disclosure provides conjugates including a PNA sequence, an uncharged DNA sequence, or a DNA sequence comprising charged and uncharged bases.

STATEMENT OF INDUSTRIAL APPLICABILITY

The present disclosure has industrial applicability in the field of medicine and diagnostics.

BACKGROUND OF THE DISCLOSURE

Cell staining methods, including immunohistochemistry (IHC) and in situ hybridization analysis (ISH), are useful tools in histological diagnosis and the study of tissue morphology. IHC employs specific binding agents or moieties, such as antibodies, to detect an antigen of interest that may be present in a tissue sample. IHC is widely used in clinical and diagnostic applications, such as to diagnose particular disease states or conditions. For example, particular cancer types can be diagnosed based on the presence of a particular marker molecule in a sample obtained from a subject. IHC is also widely used in basic research to understand biomarker distribution and localization in different tissues. Biological samples also can be examined using in situ hybridization techniques, such as silver in situ hybridization (SISH), chromogenic in situ hybridization (CISH) and fluorescence in situ hybridization (FISH), collectively referred to as ISH. ISH is distinct from IHC in that ISH detects nucleic acids in tissue whereas IHC detects proteins in tissue.

Characterization and quantitation of the multitude of proteins expressed by an organism's genome are the focus of proteomics. Multiplex immunohistochemistry (MIHC) represents a major unmet technological need to detect and analyze multivariate protein targets in paraffin-embedded formalin-fixed tissues with broad applications in research and diagnostics. Multiplex immunohistochemistry (MIHC) techniques are attempting to address the need for detecting and analyzing multivariate protein targets in formalin-fixed, paraffin-embedded tissues. Effective MIHC techniques have broad applications in research and diagnostics. However, there are few, if any, efficient and reproducible methods that allow simultaneous and quantitative detection of multiple protein targets in tissues.

A key constraint of translational research within a clinical trial setting is that there is often a limited amount of tissue from which to carry out biomarker analyses. Further, this tissue is frequently archived and stored in formalin-fixed paraffin embedded (FFPE) blocks. Traditional methods of gene expression analysis have limitations for clinical application. For example, RT-PCR measures the expression of one gene at a time, whereas multiplex expression profiling techniques such as microarrays, covering many thousands of transcripts, are often expensive and lack flexibility and reproducibility when evaluating low-quality RNA samples such as those from FFPE. The evaluation of these assays is semi-quantitative and inherently subjective. This has led to an increase focus on developing quantitative and highly multiplexed assays that enable profiling of multiple markers with a single assay. Platforms that enable multiplexed analysis of biomarkers from limited amounts of poor-quality material are therefore very attractive.

NanoString nCounter technology, which enables direct automated detection of nucleic acids (DNA and/or RNA) is a relatively new technology that has been employed in various clinical and research applications. Commonly, the target nucleic acid (DNA or RNA) is hybridized to a biotinylated DNA strand (capture strand,) enabling the immobilization of the nucleic acid to a streptavidin surface inside the nCounter cartridge and a fluorescently labeled DNA strand (reporter strand, 7 Kb of which about 50 bases are complementary to the target nucleic acid). The automated digital readout of the fluorescently labeled reporter strand is believed to allow for the non-amplified measurement of up to 800 nucleic acid targets within one sample.

DNA antibody barcoding consists of labeling an antibody with a DNA strand that can be used as a unique molecular tag. Combining DNA antibody barcoding with the NanoString nCounter technology expanded the NanoString nCounter technology to encompass applications involving multiplexed protein analysis.

Synthetic molecules that can bind with high sequence specificity to a chosen target in a gene sequence are of interest in medicinal and biotechnological contexts. They show promise for the development of gene therapeutic agents, diagnostic devices for genetic analysis, and as molecular tools for nucleic acid manipulations. Peptide nucleic acid (PNA) is a nucleic acid analog in which the sugar phosphate backbone of natural nucleic acid has been replaced by a synthetic peptide backbone usually formed from N-(2-amino-ethyl)-glycine units, resulting in an achiral and uncharged mimic. It is believed to be chemically stable and resistant to hydrolytic (enzymatic) cleavage and thus not expected to be degraded inside a living cell. PNA is capable of sequence-specific recognition of DNA and RNA obeying the Watson-Crick hydrogen bonding scheme, and the hybrid complexes exhibit extraordinary thermal stability and unique ionic strength effects. Since PNA contains no charges, the binding hybridization between PNA and DNA is stronger than that between DNA and DNA for the same sequence.

BRIEF SUMMARY OF THE DISCLOSURE

In one aspect of the present disclosure is a conjugate having the structure of Formula (I):

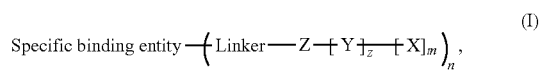

(I)

wherein
'Specific binding entity' is selected from the group consisting of an antibody (e.g. a primary antibody or a secondary antibody), an antibody fragment, a drug/antibody complex, and a nucleic acid;
'Linker' is a branched or unbranched, linear or cyclic, substituted or unsubstituted, saturated or unsaturated, group having between 2 and 80 carbon atoms, and optionally having one or more heteroatoms selected from O, N, or S;

Z is selected from the group consisting of a PNA sequence, an uncharged DNA sequence, and a DNA sequence comprising charged and uncharged bases;

X is a label;

Y is a branched or unbranched, linear or cyclic, substituted or unsubstituted, saturated or unsaturated group having between 1 and 12 carbon atoms and optionally having one or more O, N, or S heteroatoms;

m is 0 or an integer ranging from 1 to 6;

z is 0 or 1; and n is an integer ranging from 1 to 12.

In some embodiments, X is biotin, an enzyme, a chromogen, a fluorophore, a hapten, and a mass spectrometry tag.

In some embodiments, the 'Specific Binding Entity' is a primary antibody. In some embodiments, the 'Specific Binding Entity' is a secondary antibody.

In some embodiments, Z comprises a DNA sequence comprising only uncharged DNA bases. In some embodiments, Z comprises a DNA sequence comprising a mixture of charged and uncharged bases. In some embodiments, Z comprises a DNA sequence in which at least 50% of the bases in the DNA sequence are uncharged.

In some embodiments, Z comprises a PNA sequence. In some embodiments, the PNA sequence comprises between about 5 and 20 bases. In some embodiments, the PNA sequence comprises between about 5 and 15 bases. In some embodiments, the PNA sequence comprises between about 5 and 10 bases. In some embodiments, the PNA sequence comprises between about 8 and 12 bases. In some embodiments, the PNA sequence comprises about 15 bases. In some embodiments, the PNA sequence comprises about 10 bases.

In some embodiments, the 'Specific Binding Entity' is a primary antibody and Z is a PNA sequence. In some embodiments, the 'Specific Binding Entity' is a primary antibody and Z is a PNA sequence having 10 nucleotides.

In some embodiments, the 'Linker' comprises a group which is capable of being cleaved. In some embodiments, the 'Linker' comprises one or more PEG groups as disclosed herein.

In another aspect of the present disclosure is a conjugate having the structure of Formula (IC):

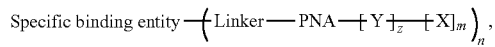

wherein

'Specific binding entity' is selected from the group consisting of an antibody, an antibody fragment, a drug/antibody complex, and a nucleic acid;

'Linker' is a branched or unbranched, linear or cyclic, substituted or unsubstituted, saturated or unsaturated, group having between 2 and 80 carbon atoms, and optionally having one or more heteroatoms selected from O, N, or S;

'PNA' is a PNA sequence;

X is a label;

Y is a branched or unbranched, linear or cyclic, substituted or unsubstituted, saturated or unsaturated group having between 1 and 12 carbon atoms and optionally having one or more O, N, or S heteroatoms;

m is 0 or an integer ranging from 1 to 6;

z is 0 or 1; and n is an integer ranging from 1 to 12.

In some embodiments, X is biotin, an enzyme, a chromogen, a fluorophore, a hapten, and a mass spectrometry tag.

In some embodiments, the PNA sequence comprises between about 5 and 20 bases.

In some embodiments, the PNA sequence comprises between about 5 and 15 bases. In some embodiments, the PNA sequence comprises between about 5 and 10 bases. In some embodiments, the PNA sequence comprises about 15 bases. In some embodiments, the PNA sequence comprises about 10 bases.

In some embodiments, the 'Specific binding entity' is a primary antibody. In some embodiments, the 'Specific binding entity' is a secondary antibody. In some embodiments, X is biotin. In some embodiments, m is 0, z is 0, and n is greater than 1. In some embodiments, n is an integer ranging from between 2 and 6. In some embodiments, 'Linker' comprises at least one PEG group.

In some embodiments, the 'Specific Binding Entity' is a primary antibody and the PNA sequence comprises 10 nucleotides.

In some embodiments, 'Linker' has the structure depicted in Formula (IIIa):

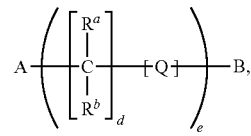

wherein d and e are integers each independently ranging from 2 to 20;

Q is a bond, O, S, or $N(R^c)(R^d)$;

$R^a$ and $R^b$ are independently H, a $C_1$-$C_4$ alkyl group, F, Cl, or $N(R^c)(R^d)$;

$R^c$ and $R^d$ are independently CH3 or H; and

A and B are independently a branched or unbranched, linear or cyclic, substituted or unsubstituted, saturated or unsaturated group having between 1 and 12 carbon atoms and optionally having one or more O, N, or S heteroatoms.

In some embodiments, d and e are integers ranging from 2 to 6. In some embodiments, at least one of A or B comprises a cleavable moiety. In some embodiments, the cleavable moiety is a photocleavable group. In some embodiments, the cleavable moiety is a chemically cleavable group. In some embodiments, 'Specific binding entity' is an antibody, 'Linker' comprises at least one PEG group, m is 0, z is 0, and n is greater than 1. In some embodiments, 'Specific binding entity' is an antibody, 'Linker' comprises at least one PEG group, and n is greater than 1. In some embodiments, 'Linker' further comprises at least one cleavable group. In some embodiments, X is a hapten.

In another aspect of the present disclosure is an oligomer having the structure of Formula (IB):

wherein

T is a group having between 1 and 4 carbon atoms and optionally substituted with O, N, or S and having a terminal reactive moiety;

'Linker' is a branched or unbranched, linear or cyclic, substituted or unsubstituted, saturated or unsaturated, group having between 2 and 80 carbon atoms, and optionally having one or more heteroatoms selected from O, N, or S;

'PNA' is a PNA sequence;

X is a label;

Y is a branched or unbranched, linear or cyclic, substituted or unsubstituted, saturated or unsaturated group having between 1 and 12 carbon atoms and optionally having one or more O, N, or S heteroatoms;

m is 0 or an integer ranging from 1 to 6; and z is 0 or 1.

In some embodiments, X is biotin, an enzyme, a chromogen, a fluorophore, a hapten, and a mass spectrometry tag.

In some embodiments, X is biotin.

In some embodiments, the PNA sequence comprises between about 5 and 20 bases.

In some embodiments, the PNA sequence comprises between about 5 and 15 bases. In some embodiments, the PNA sequence comprises between about 5 and 10 bases. In some embodiments, the PNA sequence comprises between about 8 and 12 bases. In some embodiments, the PNA sequence comprises about 15 bases. In some embodiments, the PNA sequence comprises about 10 bases.

In some embodiments, the 'Specific Binding Entity' is a primary antibody and the PNA sequence comprises 10 nucleotides.

In some embodiments, m is 0, z is 0, and n is greater than 1.

In some embodiments, n is an integer ranging from between 2 and 6. In some embodiments, 'Linker' comprises at least one PEG group. In some embodiments, 'Linker' has the structure depicted in Formula (IIIa):

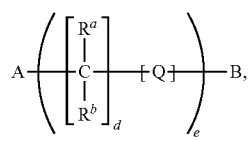

wherein d and e are integers each independently ranging from 2 to 20;

Q is a bond, O, S, or $N(R^c)(R^d)$;

$R^a$ and $R^b$ are independently H, a $C_1$-$C_4$ alkyl group, F, Cl, or $N(R^c)(R^d)$;

$R^c$ and $R^d$ are independently $CH_3$ or H; and

A and B are independently a branched or unbranched, linear or cyclic, substituted or unsubstituted, saturated or unsaturated group having between 1 and 12 carbon atoms and optionally having one or more O, N, or S heteroatoms.

In some embodiments, d and e are integers ranging from 2 to 6. In some embodiments, at least one of A or B comprises a cleavable moiety. In some embodiments, the cleavable moiety is a photocleavable group. In some embodiments, the cleavable moiety is a chemically cleavable group.

In another aspect of the present disclosure is a method of detecting a target in a sample, comprising:

(a) contacting the sample with a first conjugate, the first conjugate having the structure of Formula (I):

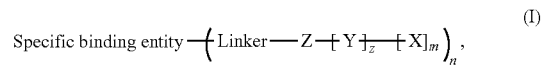

wherein

'Specific binding entity' is selected from the group consisting of an antibody, an antibody fragment, a drug/antibody complex, and a nucleic acid;

'Linker' is a branched or unbranched, linear or cyclic, substituted or unsubstituted, saturated or unsaturated, group having between 2 and 80 carbon atoms, and optionally having one or more heteroatoms selected from O, N, or S;

Z is selected from the group consisting of a PNA sequence, an uncharged DNA sequence, and a DNA sequence comprising charged and uncharged bases;

X is a label;

Y is a branched or unbranched, linear or cyclic, substituted or unsubstituted, saturated or unsaturated group having between 1 and 12 carbon atoms and optionally having one or more O, N, or S heteroatoms;

m is 0 or an integer ranging from 1 to 6;

z is 0 or 1; and n is an integer ranging from 1 to 12; and (b) contacting the sample with first detection reagents to facilitate detection of the PNA conjugate.

In some embodiments, X is selected from the group consisting of biotin, an enzyme, a chromogen, a fluorophore, a hapten, and a mass spectrometry tag.

In some embodiments, the 'Specific Binding Entity' is a primary antibody and Z is a PNA sequence. In some embodiments, the 'Specific Binding Entity' is a primary antibody and Z is a PNA sequence having 10 nucleotides.

In some embodiments, Z comprises a DNA sequence comprising only uncharged DNA bases. In some embodiments, Z comprises a DNA sequence comprising a mixture of charged and uncharged bases. In some embodiments, Z comprises a DNA sequence in which at least 50% of the bases in the DNA sequence are uncharged. In some embodiments, the PNA sequence comprises between about 5 and 20 bases. In some embodiments, the PNA sequence comprises between about 5 and 15 bases. In some embodiments, the PNA sequence comprises between about 5 and 10 bases. In some embodiments, the PNA sequence comprises about 15 bases. In some embodiments, the PNA sequence comprises about 10 bases.

In another aspect of the present disclosure is a method of detecting a target in a sample, comprising:

(a) contacting the sample with a first conjugate, the first conjugate having the structure of Formula (IC):

wherein

'Specific binding entity' is selected from the group consisting of an antibody, an antibody fragment, a drug/antibody complex, and a nucleic acid;

'Linker' is a branched or unbranched, linear or cyclic, substituted or unsubstituted, saturated or unsaturated, group having between 2 and 80 carbon atoms, and optionally having one or more heteroatoms selected from O, N, or S;

'PNA' is a PNA sequence;

X is a label;

Y is a branched or unbranched, linear or cyclic, substituted or unsubstituted, saturated or unsaturated group having between 1 and 12 carbon atoms and optionally having one or more O, N, or S heteroatoms;

m is 0 or an integer ranging from 1 to 6;

z is 0 or 1; and n is an integer ranging from 1 to 12; and (b) contacting the sample with first detection reagents to facilitate detection of the PNA conjugate.

In some embodiments, X is selected from the group consisting of biotin, an enzyme, a chromogen, a fluorophore, a hapten, and a mass spectrometry tag.

In some embodiments, the PNA sequence comprises between about 5 and 20 bases.

In some embodiments, the PNA sequence comprises between about 5 and 15 bases. In some embodiments, the PNA sequence comprises between about 5 and 10 bases.

In some embodiments, the PNA sequence comprises about 15 bases. In some embodiments, the PNA sequence comprises about 10 bases.

In some embodiments, the 'Specific binding entity' is a primary antibody and wherein the primary antibody is specific to a first target. In some embodiments, the 'Specific binding entity' is a secondary antibody, and wherein the method further comprises the step of contacting the sample with a primary antibody specific for a first target prior to contacting the sample with the first conjugate, and wherein the first conjugate is specific to the first primary antibody. In some embodiments, the first detection reagents are anti-label antibodies specific to a label of the conjugate. In some embodiments, the label is a hapten and the anti-label antibodies are anti-hapten antibodies. In some embodiments, the detection reagents comprise a PNA or DNA sequence complementary to a PNA sequence of the first conjugate, the complementary PNA or DNA sequence conjugated to a reporter moiety. In some embodiments, the reporter moiety is a fluorophore. In some embodiments, the reporter moiety is a chromogen. In some embodiments, the reporter moiety is an enzyme. In some embodiments, the reporter moiety is a hapten, and where the method further comprises contacting the sample with anti-hapten antibodies specific to the hapten of the complementary PNA or DNA sequence.

In another aspect of the present disclosure is a method of detecting a target in a sample, comprising: (a) contacting the sample with a first conjugate, the first conjugate having the structure of Formula (IC):

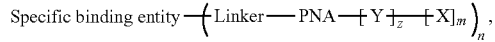

(IC)

wherein

'Specific binding entity' is selected from the group consisting of an antibody (e.g. a primary antibody or a secondary antibody), an antibody fragment, a drug/antibody complex, and a nucleic acid;

'Linker' is a branched or unbranched, linear or cyclic, substituted or unsubstituted, saturated or unsaturated, group having between 2 and 80 carbon atoms, and optionally having one or more heteroatoms selected from O, N, or S; the 'Linker' further comprising a cleavable group;

'PNA' is a PNA sequence;

X is a label;

Y is a branched or unbranched, linear or cyclic, substituted or unsubstituted, saturated or unsaturated group having between 1 and 12 carbon atoms and optionally having one or more O, N, or S heteroatoms;

m is 0;

z is 0; and n is an integer ranging from 1 to 12; and (b) contacting the sample with a reagent (or a light source, depending on the cleavable group selected) to cleave the cleavable group on the 'Linker;' and (c) quantifying the amount of the cleaved 'PNA' sequence.

The skilled artisan will appreciate that the above-identified steps may be repeated any number of times with different conjugates to provide a multiplex assay.

In some embodiments, the 'Specific Binding Entity' is a primary antibody.

In some embodiments, the cleavable group is selected from the group consisting of a photocleavable group, a chemically cleavable group, or an enzymatically cleavable group. In some embodiments, the cleavable group is a disulfide bond.

In some embodiments, X is selected from the group consisting of biotin, an enzyme, a chromogen, a fluorophore, a hapten, and a mass spectrometry tag. In some embodiments, X is biotin.

In some embodiments, the quantification of the amount of the PNA sequence is performed using NanoString nCounter technology. In some embodiments, the quantification of the amount of the PNA sequence is performed using Gyrolab technology (available from Gyros), such as described herein.

In some embodiments, after PNA cleavage, the antibody-bound tissue section is re-stained with a conventional method such as IHC or IF to allow visualization of the spatial distribution of the marker encoded by the PNA tag.

In some embodiments, the method further comprises introducing a single stranded DNA sequence which is complementary to the PNA sequence of the conjugate of Formula (IC). In some embodiments, the complementary single stranded DNA sequence is conjugated to a reporter moiety. In some embodiments, the complementary single stranded DNA sequence is conjugated to a hapten. In some embodiments, the complementary single stranded DNA sequence is conjugated to digoxigenin.

In some embodiments, the 'Specific Binding Entity' is a primary antibody, and wherein the method further comprises introducing a secondary antibody specific for the primary antibody. In some embodiments, the secondary antibody is conjugated to a reporter moiety.

In some embodiments, the PNA sequence comprises between about 5 and 20 bases.

In some embodiments, the PNA sequence comprises between about 5 and 15 bases. In some embodiments, the PNA sequence comprises between about 5 and 10 bases. In some embodiments, the PNA sequence comprises about 15 bases. In some embodiments, the PNA sequence comprises about 10 bases.

It is believed that since PNA contains no charges, unlike DNA, the binding between PNA and DNA is stronger than that between DNA and DNA, allowing the use of comparatively shorter PNA sequences to label antibodies while achieving binding affinity and specificity not possible with DNA-conjugates. It is also anticipated that the shorter PNA sequence may help minimize its interference with antibody-antigen binding and tissue non-specific binding. Therefore, the PNA-antibody conjugates disclosed herein are expected to maintain the binding specificity of the antibody while the PNA oligomer functions as a unique molecular tag that can be either visualized in situ on slides (IF or IHC) through hybridization with a signal generating molecule, or quantified off the slides by a high-throughput technology such as NanoString technology, Gryos technology, or mass spectrometry (see FIG. 1). In addition, virtually unlimited unique sequence/tags can be readily generated and detected under almost identical conditions, eliminating the need to optimize individual conjugates. Importantly, a cleavable linker (either photo or chemical cleavable) can be placed between the PNA oligomer and the antibody (see FIG. 1), allowing facile sample collection for off-slide protein profiling (multiplexed quantification).

BRIEF DESCRIPTION OF THE FIGURES

The patent or application file contains at least one drawing executed in color. Copies of this patent or patent application publication with color drawings will be provided to the Office upon request and the payment of the necessary fee.

FIG. 4A illustrates IHC detection of a biotinylated PNA as a membrane marker. Tonsil slides were treated with "haptenated" primary antibodies (an antibody labeled with a hapten) followed by treatment with a corresponding PNA-conjugate against the respective hapten. Biotin in the PNA conjugates was then detected with SA-HRP and DAB deposition.

FIG. 4B illustrates IHC detection of a biotinylated PNA as a nuclear marker. Tonsil slides were treated with "haptenated" primary antibodies (an antibody labeled with a hapten) followed by treatment with a corresponding PNA-conjugate against the respective hapten. Biotin in the PNA conjugates was then detected with SA-HRP and DAB deposition.

FIG. 5A illustrates the chemical cleavage of the PNA tag. Tonsil slides were treated with mouse anti-Ki67 followed by PNA-conjugated GAM. The slide was further treated with SA-HRP and DAB deposition.

FIG. 5B illustrates the chemical cleavage of the PNA tag. Tonsil slides were treated with mouse anti-Ki67 followed by PNA-conjugated GAM. The slide was further treated with about 20 mM TCEP before SA-HRP incubation and DAB deposition.

FIG. 5C illustrates the chemical cleavage of the PNA tag. Tonsil slides were treated with rabbit anti-CD45 followed by PNA-conjugated GAR. The slide was further treated with SA-HRP and DAB deposition.

FIG. 5D illustrates the chemical cleavage of the PNA tag. Tonsil slides were treated with rabbit anti-CD45 followed by PNA-conjugated GAR. The slide was further treated with about 20 mM TCEP before SA-HRP incubation and DAB deposition.

FIG. 6A illustrates fluorescence detection of the biotinylated PNA. Tonsil slides were treated with mouse anti-Ki67 and (b) no primary antibody followed by PNA-conjugated GAM. The slides were further incubated with SA-FITC.

FIG. 6B illustrates fluorescence detection of the biotinylated PNA. Tonsil slides were treated with no primary antibody followed by PNA-conjugated GAM. The slides were further incubated with SA-FITC.

FIG. 6C provides a scheme illustrating a fluorescent-based detection scheme.

FIG. 8A illustrates PNA detection with fluorescently labeled complement DNA. Tonsil slides treated with rabbit anti-Ki67 followed by PNA-conjugated GAR. The slides were then incubated with fluorescently labeled DNA sequences that are complement to the PNA tag. FITC labeled DNA sequences were utilized.

FIG. 8B illustrates PNA detection with fluorescently labeled complement DNA. Negative controls with no primary antibody added with otherwise identical conditions to that depicted in FIG. 8A.

FIG. 8C illustrates PNA detection with fluorescently labeled complement DNA. Tonsil slides treated with rabbit anti-Ki67 followed by PNA-conjugated GAR. The slides were then incubated with fluorescently labeled DNA sequences that are complement to the PNA tag. Rhodamine labeled DNA sequences were utilized.

FIG. 8D illustrates PNA detection with fluorescently labeled complement DNA. Negative controls with no primary antibody added with otherwise identical conditions to that depicted in FIG. 8C.

FIG. 8E illustrates a schematic illustrating FITC or Rhodamine labeling.

FIG. 11 illustrates the chemical structure of the photolabile linker used to synthesize photocleavable PNA.

FIG. 12A illustrates the photocleavage of PNA. Slides were treated with Ki67, then GAR-PL-PNA. Slides were irradiated with a hand-held UV lamp for 0 minutes.

FIG. 12B illustrates the photocleavage of PNA. Slides were treated with Ki67, then GAR-PL-PNA. Slides were irradiated with a hand-held UV lamp for 5 minutes.

FIG. 12C illustrates the photocleavage of PNA. Slides were treated with Ki67, then GAR-PL-PNA. Slides were irradiated with a hand-held UV lamp for 10 minutes.

FIGS. 25A and 25B illustrates tonsil tissue incubated to anti-Ki67 and GAR-short PNA followed by DNA-DIG (DNA sequence complementary to the short PNA tag called AB14 that has a DIG on its end). antiDIG-HRP antibody was added for detection. In this case, DNA was detected that was complementary to the PNA tag. Two different concentrations of the complementary DNA-DIG are shown. FIG. 25A illustrates a concentration of about 5 micromolar. FIG. 25B illustrates a concentration of about 10 micromolar.

SEQUENCE LISTING

The nucleic and amino acid sequences provided herein are shown using standard letter abbreviations for nucleotide bases, and three letter code for amino acids, as defined in 37 C.F.R. 1.822. The sequence listing is submitted as an ASCII text file, named "2017-12-18 Ventana-074WO_P34032WO_ST25.txt" created on Dec. 18, 2017, 6 KB, which is incorporated by reference herein.

DETAILED DESCRIPTION

Figure 1:
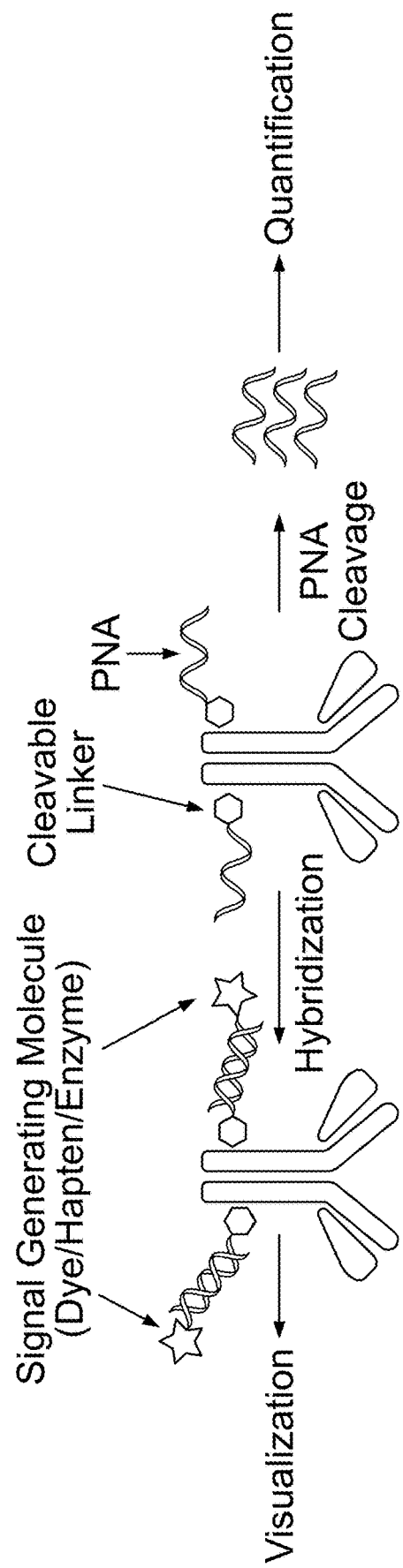
FIG. 1 provides an overview of the structure of a PNA conjugate and their use in both visualization of targets within a sample (qualitative) and quantitative assessment of the PNA tags cleaved from the bound antibody.

In general, the present disclosure is directed to conjugates, e.g. PNA conjugates, as well as methods of employing the conjugates for detecting one or more targets in a biological sample, e.g. a tissue sample. Without wishing to be bound by any particular theory, it is believed that the conjugates, when used in an assay, allow for qualitative and quantitative evaluation of a high numbers of targets, including protein targets, simultaneously (see FIG. 1).

As used herein, the singular terms "a," "an," and "the" include plural referents unless the context clearly indicates otherwise. Similarly, the word "or" is intended to include "and" unless the context clearly indicates otherwise.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of." "Consisting essentially of," when used in the claims, shall have its ordinary meaning as used in the field of patent law.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the term "alkyl" refers to a straight or branched hydrocarbon chain that comprises a fully saturated (no double or triple bonds) hydrocarbon group. The alkyl group may be substituted or unsubstituted.

As used herein, the term "antibody," refers to immunoglobulins or immunoglobulin-like molecules, including by way of example and without limitation, IgA, IgD, IgE, IgG and IgM, combinations thereof, and similar molecules produced during an immune response in any vertebrate, (e.g., in mammals such as humans, goats, rabbits and mice) and antibody fragments (such as F(ab')2 fragments, Fab' fragments, Fab'-SH fragments and Fab fragments as are known in the art, recombinant antibody fragments (such as sFv fragments, dsFv fragments, bispecific sFv fragments, bispecific dsFv fragments, F(ab)'2 fragments, single chain Fv proteins ("scFv"), disulfide stabilized Fv proteins ("dsFv"), diabodies, and triabodies (as are known in the art), and camelid antibodies) that specifically bind to a molecule of interest (or a group of highly similar molecules of interest) to the substantial exclusion of binding to other molecules. Antibody further refers to a polypeptide ligand comprising at least a light chain or heavy chain immunoglobulin variable region which specifically recognizes and binds an epitope of an antigen. Antibodies may be composed of a heavy and a light chain, each of which has a variable region, termed the variable heavy (VH) region and the variable light (VL) region. Together, the VH region and the VL region are responsible for binding the antigen recognized by the antibody. The term antibody also includes intact immunoglobulins and the variants and portions of them well known in the art.

As used herein, the term "antigen" refers to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, nucleic acids and proteins.

As used herein, the terms "biological sample" or "tissue sample" are any solid or fluid sample obtained from, excreted by or secreted by any living organism, including without limitation, single celled organisms, such as bacteria, yeast, protozoans, and amoebas among others, multicellular organisms (such as plants or animals, including samples from a healthy or apparently healthy human subject or a human patient affected by a condition or disease to be diagnosed or investigated, such as cancer). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease). A biological sample can also be a sample obtained from any organ or tissue (including a biopsy or autopsy specimen, such as a tumor biopsy) or can include a cell (whether a primary cell or cultured cell) or medium conditioned by any cell, tissue or organ. The samples may be tumor samples, including those from melanoma, renal cell carcinoma, and non-small-cell lung cancers. In some embodiments, the samples are analyzed for disease states such as cancer by detecting targets, including biomarkers (e.g. proteins or nucleic acid sequences), within the tissue sample. The described embodiments of the disclosed method can also be applied to samples that do not have abnormalities, diseases, disorders, etc., referred to as "normal" samples or "control" samples. For example, it may be useful to test a subject for cancer by taking tissue samples from multiple locations, and these samples may be used as controls and compared to later samples to determine whether a particular cancer has spread beyond its primary origin. In some embodiments, the sample may be a protein that has been extracted and purified from a cell lysate, a tissue, or from a whole organism through the conventional protein extraction methods. In the context of the present disclosure, the extracted proteins can then be mixed with PNA-conjugated antibodies where the antibodies become bound to the specific proteins. The PNA is then released and counted to quantify the protein.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl or aryl group, or the total number of carbon atoms and heteroatoms in a heteroalkyl, heterocyclyl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$ and $(CH_3)_3C-$. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, "conjugate" refers to two or more molecules (and/or materials such as nanoparticles) that are covalently linked into a larger construct.

As used herein, the term "couple" or "coupling" refers to the joining, bonding (e.g. covalent bonding), or linking of one molecule or atom to another molecule or atom.

As used herein, the term "detection probes" include nucleic acid probes or primary antibodies which bind to specific targets (e.g. nucleic acid sequences, proteins, etc.). The detection probes may include a label for direct detection, such as radioactive isotopes, enzyme substrates, cofactors, ligands, chemiluminescent or fluorescent agents, haptens (including, but not limited to, DNP), and enzymes. Alternatively, the detection probes may contain no label or tag and may be detected indirectly (e.g. with a secondary antibody that is specific for the detection probe).

As used herein, the term "haptens" are small molecules that can combine specifically with an antibody, but typically are substantially incapable of being immunogenic except in combination with a carrier molecule. In some embodiments, haptens include, but are not limited to, pyrazoles (e.g. nitropyrazoles); nitrophenyl compounds; benzofurazans; triterpenes; ureas (e.g. phenyl ureas); thioureas (e.g. phenyl thioureas); rotenone and rotenone derivatives; oxazole (e.g. oxazole sulfonamides); thiazoles (e.g. thiazole sulfonamides); coumarin and coumarin derivatives; and cyclolignans. Additional non-limiting examples of haptens include thiazoles; nitroaryls; benzofurans; triperpenes; and cyclolignans. Specific examples of haptens include di-nitrophenyl, biotin, digoxigenin, and fluorescein, and any derivatives or analogs thereof. Other haptens are described in U.S. Pat. Nos. 8,846,320; 8,618,265; 7,695,929; 8,481,270; and 9,017,954, the disclosures of which are incorporated herein by reference in their entirety. The haptens themselves may be suitable for direct detection, i.e. they may give off a suitable signal for detection.

As used herein, the terms "halogen atom" or "halogen" mean any one of the radio-stable atoms of column 7 of the Periodic Table of the Elements, such as, fluorine, chlorine, bromine and iodine.

As used herein, the term "immunohistochemistry" refers to a method of determining the presence or distribution of an antigen in a sample by detecting interaction of the antigen with a specific binding agent, such as an antibody. A sample is contacted with an antibody under conditions permitting antibody-antigen binding. Antibody-antigen binding can be detected by means of a detectable label conjugated to the antibody (direct detection) or by means of a detectable label conjugated to a secondary antibody, which binds specifically to the primary antibody (indirect detection).

As used herein, the terms "multiplex," "multiplexed," or "multiplexing" refer to detecting multiple targets in a sample concurrently, substantially simultaneously, or sequentially. Multiplexing can include identifying and/or quantifying multiple distinct nucleic acids (e.g., DNA, RNA, mRNA, miRNA) and polypeptides (e.g., proteins) both individually and in any and all combinations.

As used herein, the term "oligonucleotides," "polynucleotides" and "nucleic acids" are used here to encompass all forms of nucleic acid molecules. Without limitation, this category includes ribonucleic acids (RNA), deoxyribonucleic acid (DNA), peptide nucleic acids (PNA), and their derivatives, with and without modifications, respectively.

As used herein, the term "primary antibody" refers to an antibody which binds specifically to a target protein antigen in a tissue sample. A primary antibody is generally the first antibody used in an immunohistochemical procedure. Primary antibodies may thus serve as "detection probes" for detecting a target within a tissue sample.

As used herein, the term "peptide nucleic acids" or "PNAs" are oligonucleotide analogues in which the sugar-phosphate backbone has been replaced by a pseudopeptide skeleton. PNAs bind DNA and RNA with high specificity and selectivity, leading to PNA-RNA and PNA-DNA hybrids which are believed to be more stable than the corresponding nucleic acid complexes. The binding affinity and selectivity of PNAs for nucleic acids can be modified by the introduction of stereogenic centers (such as D-Lys-based units) into the PNA backbone. PNA can be an oligomer, linked polymer or chimeric oligomer. Methods for the chemical synthesis and assembly of PNAs are described in U.S. Pat. Nos. 5,539,082, 5,527,675, 5,623,049, 5,714,331, 5,736,336, 5,773,571, and 5,786,571, the disclosure of which are hereby incorporated by reference herein in their entireties.

As used herein, the terms "reactive group" "reactive groups" as used throughout mean any of a variety of groups (e.g. functional groups) suitable for coupling a first unit to a second unit as described herein. For example, the reactive group might be an amine-reactive group, such as an isothiocyanate, an isocyanate, an acyl azide, an NHS ester, an acid chloride, such as sulfonyl chloride, aldehydes and glycols, epoxides and oxiranes, carbonates, arylating agents, imidoesters, carbodiimides, anhydrides, and combinations thereof. Suitable thiol-reactive functional groups include haloacetyl and alkyl halides, maleimides, aziridines, acryloyl derivatives, arylating agents, thiol-disulfide exchange reagents, such as pyridyl disulfides, TNB-thiol, and disulfide reductants, and combinations thereof. Suitable carboxylate-reactive functional groups include diazoalkanes, diazoacetyl compounds, carbonyldiimidazole compounds, and carbondiimides. Suitable hydroxyl-reactive functional groups include epoxides and oxiranes, carbonyldiimidazole, N,N'-disuccinimidyl carbonates or N-hydroxysuccinimidyl chloroformates, periodate oxidizing compounds, enzymatic oxidation, alkyl halogens, and isocyanates. Aldehyde and ketone-reactive functional groups include hydrazines, Schiff bases, reductive amination products, Mannich condensation products, and combinations thereof. Active hydrogen-reactive compounds include diazonium derivatives, Mannich condensation products, iodination reaction products, and combinations thereof. Photoreactive chemical functional groups include aryl azides, halogenated aryl azides, benzophonones, diazo compounds, diazirine derivatives, and combinations thereof.

As used herein, the phrase "reporter moiety" refers to a molecule or material that can produce a detectable (such as visually, electronically or otherwise) signal that indicates the presence (i.e. qualitative analysis) and/or concentration (i.e. quantitative analysis) of the conjugate, including PNA conjugate, in a sample. A detectable signal can be generated by any known or yet to be discovered mechanism including absorption, emission and/or scattering of a photon (including radio frequency, microwave frequency, infrared frequency, visible frequency and ultra-violet frequency photons).

As used herein, the term "secondary antibody" herein refers to an antibody which binds specifically to a detection probe or portion thereof (e.g. a hapten or a primary antibody), thereby forming a bridge between the detection probe and a subsequent reagent (e.g. a label, an enzyme, etc.), if any. A secondary antibody may be used to indirectly detect the detection probes, e.g. primary antibodies. Examples of secondary antibodies include anti-tag antibodies, anti-species antibodies, and anti-label antibodies, each described herein.

As used herein the term "specific binding entity" refers to a member of a specific-binding pair. Specific binding pairs are pairs of molecules that are characterized in that they bind each other to the substantial exclusion of binding to other molecules (for example, specific binding pairs can have a binding constant that is at least $10^3$ $M^{-1}$ greater, $10^4$ $M^{-1}$ greater or $10^5$ $M^{-1}$ greater than a binding constant for either of the two members of the binding pair with other molecules in a biological sample). Examples of specific binding moieties include specific binding proteins (for example, antibodies, lectins, avidins such as streptavidins, and protein A). Specific binding moieties can also include the molecules (or portions thereof) that are specifically bound by such specific binding proteins. Specific binding entities include primary antibodies, described above, or nucleic acid probes.

As used herein, the terms "stain," "staining," or the like as used herein generally refers to any treatment of a biological specimen that detects and/or differentiates the presence, location, and/or amount (such as concentration) of a particular molecule (such as a lipid, protein or nucleic acid) or particular structure (such as a normal or malignant cell, cytosol, nucleus, Golgi apparatus, or cytoskeleton) in the biological specimen. For example, staining can provide contrast between a particular molecule or a particular cellular structure and surrounding portions of a biological specimen, and the intensity of the staining can provide a measure of the amount of a particular molecule in the specimen. Staining can be used to aid in the viewing of molecules, cellular structures and organisms not only with bright-field microscopes, but also with other viewing tools, such as phase contrast microscopes, electron microscopes, and fluorescence microscopes. Some staining performed by the system 2 can be used to visualize an outline of a cell. Other staining performed by the system 2 may rely on certain cell components (such as molecules or structures) being stained without or with relatively little staining other cell components. Examples of types of staining methods performed by the system 2 include, without limitation, histochemical methods, immunohistochemical methods, and other methods based on reactions between molecules (including non-covalent binding interactions), such as hybridization reactions between nucleic acid molecules. Particular staining methods include, but are not limited to, primary staining methods (e.g., H&E staining, Pap staining, etc.), enzyme-linked immunohistochemical methods, and in situ RNA and DNA hybridization methods, such as fluorescence in situ hybridization (FISH).

Whenever a group or moiety is described as being "substituted" or "optionally substituted" (or "optionally having" or "optionally comprising") that group may be unsubstituted or substituted with one or more of the indicated substituents. Likewise, when a group is described as being "substituted or unsubstituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, cyanate, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, ether, amino (e.g. a monosubstituted amino group or a di-substituted amino group), and protected derivatives thereof. Any of the above groups may include one or more heteroatoms, including O, N, or S. For example, where a moiety is substituted with an alkyl group, that alkyl group may comprise a heteroatom selected from O, N, or S (e.g. —$CH_2$—$CH_2$—O—$CH_2$—$CH_2$—).

As used herein, the term "substantially" means the qualitative condition of exhibiting total or near-total extent or degree of a characteristic or property of interest. In some embodiments, "substantially" means within about 20%. In some embodiments, "substantially" means within about 15%. In some embodiments, "substantially" means within about 10%. In some embodiments, "substantially" means within about 5%.

As used herein, the term "target" means any molecule for which the presence, location and/or concentration is or can be determined. Examples of targets include nucleic acid sequences and proteins, such as those disclosed herein.

Oligomers and Conjugates

One aspect of the present disclosure is directed to conjugates of a specific binding entity and an oligomer. In some embodiments, the conjugates are PNA conjugates, i.e. a conjugate of a specific binding entity and an oligomer comprising a PNA sequence. In some embodiments, the specific binding entity and the oligomer are coupled via a linker, including linkers that comprise a cleavable group. In some embodiments, the oligomer comprises a PNA sequence, an uncharged DNA sequence, or a DNA sequence comprising charged and uncharged bases. In some embodiments, the oligomer comprises a PNA sequence. In some embodiments, the specific binding entity is an antibody and the oligomer comprises a PNA.

In general, the conjugates disclosed herein are suitable for use in immunohistochemical assays or in situ hybridization assays, including multiplex assays, and thereby may be used as detection probes such that targets within a tissue sample may be detected. The conjugates can be hybridized to a complimentary PNA, DNA or RNA or like sequence that can be (i) directly detected; (ii) carry a specific entity that can be directly detected such as fluorophore, enzyme (HRP); or (iii) indirectly through the binding of other antibodies such as hapten. The conjugates disclosed herein may also function as molecular "bar codes" which may be used in quantitative analyses.

In some embodiments, a conjugate of the present disclosure has the general structure of Formula (I):

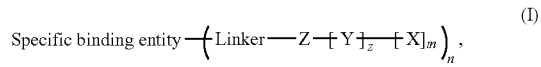

(I)

wherein

'Specific binding entity' is selected from the group consisting of an antibody, an antibody fragment, a drug/antibody complex, and a nucleic acid;

'Linker' is a branched or unbranched, linear or cyclic, substituted or unsubstituted, saturated or unsaturated, group having between 2 and 80 carbon atoms, and optionally having one or more heteroatoms selected from O, N, or S;

Z is selected from the group consisting of a PNA sequence, an uncharged DNA sequence, and a DNA sequence comprising charged and uncharged bases;

X is a label;

Y is a spacer;

m is 0 or an integer ranging from 1 to 6;

z is 0 or 1; and n is an integer ranging from 1 to 12.

In some embodiments, Z comprises a DNA sequence having only uncharged bases. In other embodiments, Z comprises a DNA sequence having both charged and uncharged bases. In yet other embodiments, Z comprises a DNA sequence wherein at least 50% of the bases of the DNA sequence are uncharged. In yet other embodiments, Z comprises a PNA sequence.

In some embodiments, the conjugate is a PNA conjugate having the general structure of Formula (IA):

Specific binding entity-PNA Oligomer    (IA), wherein

'Specific binding entity' is selected from the group consisting of an antibody, an antibody fragment, a drug/antibody complex, and a nucleic acid; and 'PNA Oligomer' comprises at least one PNA sequence.

The 'PNA Oligomer' may also comprise a linker, spacer, or other group, such as a group designed to facilitate the coupling of a PNA sequence to a specific binding entity. In other embodiments, the PNA oligomer may comprise a group which increases the water solubility of the conjugate.

In general, the 'PNA' may have any sequence, without limitation. In some embodiments, the PNA sequence is homogenous, i.e. comprising a single nucleotide. In other embodiments, the PNA sequence is heterogeneous, i.e. comprising multiple nucleotides, and the nucleotides may be organized randomly or within repeat groups. In yet other embodiments, the sequence can be designed to encode particular information, such as a bar code, as opposed to functioning solely as a carrier.

In some embodiments, 'PNA' comprises a sequencing having from 2 to 60 bases. In other embodiments, 'PNA' comprises a sequence having from 2 to 50 bases. In yet other embodiments, 'PNA' comprises a sequencing having from 2 to 40 bases. In further embodiments, 'PNA' comprises a sequencing having from 2 to 40 bases. In yet further embodiments, 'PNA' comprises a sequence having between 1 and 30 bases. In even further embodiments, 'PNA' comprises a sequence having between 1 and 20 bases. In other embodiments, 'PNA' comprises a sequence having between 20 and 40 bases. In yet other embodiments, 'PNA' comprises a sequence having between 20 and 30 bases. In yet other embodiments, 'PNA' comprises a sequence having between 30 and 40 bases. In yet other embodiments, 'PNA' comprises a sequence of between 5 and 20 bases. In yet other embodiments, 'PNA' comprises a sequence of between 5 and 15 bases. In yet other embodiments, 'PNA' comprises a sequence of between 8 and 12 bases. In yet other embodiments, 'PNA' comprises a sequence of between 12 and 18 bases. In further embodiments, 'PNA' comprises about 10 bases. In further embodiments, 'PNA' comprises about 15 bases. In further embodiments, 'PNA' comprises at least 10 bases. In further embodiments, 'PNA' comprises at least 150 bases.

Non-limiting examples of PNA sequences are provided below. In one embodiment, PNA may have the sequence GTCAACCATCTTCAG (SEQ ID NO: 1). In another embodiment, PNA may have the sequence TTAGTCCAACTGGCA (SEQ ID NO: 2). In another embodiment, PNA may have the sequence CATTCAAATCCCCGA (SEQ ID NO: 3). In another embodiment, PNA may have the sequence CCATCTTCAG (SEQ ID NO: 4). In another embodiment, PNA may have the sequence TTAGTCCAAC (SEQ ID NO: 5). In another embodiment, PNA may have the sequence GGTAGAAGTC (SEQ ID NO: 6). In another embodiment, PNA may have the sequence AATCAGGTTG (SEQ ID NO: 7). Since the PNA bases are not charged (like DNA bases) the PNA is believed to be comparatively more hydrophobic than DNA. It is also believed that the PNA hydrophobicity is proportional to the number of bases making that PNA sequence. As such, the more bases a PNA sequence has the higher the hydrophobicity will be. Consequently, a 15 base PNA sequence, for example, is more hydrophobic than a 10 base PNA sequence. It is also believed that since hydrophobic PNA sequences are not easily dissolved in aqueous solutions they are harder to conjugate to antibodies. Moreover, the conjugation of hydrophobic PNA sequences on antibodies causes missbehavior of the conjugate manifested as non-specific binding of the conjugate on the tissue. Reducing the number of bases of the PNA sequences (for example, from 10 bases from 15 bases) results in higher PNA loading and more stable conjugates.

In some embodiments, PNA Oligomer has the structure of Formula (TB):

wherein
T is a group having a terminal reactive moiety;
'Linker' is a branched or unbranched, linear or cyclic, substituted or unsubstituted, saturated or unsaturated, group having between 2 and 80 carbon atoms, and optionally having one or more heteroatoms selected from O, N, or S;
'PNA' is a PNA sequence;
X is a label;
Y is a spacer;
m is 0 or an integer ranging from 1 to 6; and
z is 0 or 1.

In some embodiments, T is a reactive group capable of forming direct a bond with a functional group of a specific binding entity, e.g. an amino group of an antibody or indirect bond through a linker, e.g. azide on the PNA sequence bound to the thiol group of the antibody via a DBCO-maleimide bifunctional linker. In some embodiments, T is a NHS ester, thiol, maleimide or azide group.

In some embodiments, the PNA conjugates have the structure of Formula (IC):

wherein
'Specific binding entity' is selected from the group consisting of an antibody, an antibody fragment, a drug/antibody complex, and a nucleic acid;
'Linker' is a branched or unbranched, linear or cyclic, substituted or unsubstituted, saturated or unsaturated, group having between 2 and 80 carbon atoms, and optionally having one or more heteroatoms selected from O, N, or S;
'PNA' is a PNA sequence;
X is a label;
Y is a spacer;
m is 0 or an integer ranging from 1 to 6;
z is 0 or 1; and
n is an integer ranging from 1 to 12.

In some embodiments, a single PNA oligomer is coupled to a specific binding entity. In other embodiments, a plurality of PNA oligomers, including those of any of Formula (TB) are coupled to a specific binding entity. In this context, in some embodiments, n presents the number of PNA oligomers (including linker, PNA sequence, and label as appropriate) coupled to the specific binding entity. In some embodiments, n is an integer ranging from 1 and 10. In other embodiments, n is an integer ranging from 1 and 8. In yet other embodiments, n is an integer ranging from 1 and 6. In yet other embodiments, n is an integer ranging from 2 and 6. In yet other embodiments, n is an integer ranging from 1 and 4. In yet other embodiments, n is an integer ranging from 2 and 4.

In some embodiments, the PNA sequence comprises between about 5 and 60 bases. In some embodiments, the PNA sequence comprises between about 5 and 30 bases. In some embodiments, the PNA sequence comprises between about 5 and 20 bases. In some embodiments, the PNA sequence comprises between about 5 and 15 bases. In some embodiments, the PNA sequence comprises between about 5 and 10 bases. In some embodiments, the PNA sequence comprises about 15 bases. In some embodiments, the PNA sequence comprises about 10 bases.

In some embodiments, the 'Specific Binding Entity" is a primary antibody and the PNA sequence comprises about 10 bases. In other embodiments, the 'Specific Binding Entity" is a secondary antibody and the PNA sequence comprises about 15 bases.

In some embodiments, the PNA conjugates of Formula (IC) have the structure of Formula (ID):

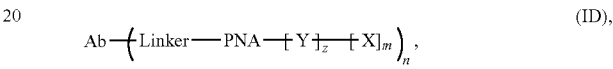

wherein
'Ab' is selected from the group consisting of a primary antibody or a secondary antibody);
'Linker' is a branched or unbranched, linear or cyclic, substituted or unsubstituted, saturated or unsaturated, group having between 2 and 80 carbon atoms, and optionally having one or more heteroatoms selected from O, N, or S;
'PNA' is a PNA sequence;
X is a label;
Y is a spacer;
m is 0 or an integer ranging from 1 to 6;
z is 0 or 1; and
n is an integer ranging from 1 to 12.

In some embodiments, one or more PNA oligomers are coupled to a primary or secondary antibody to form a PNA-antibody conjugate. In some embodiments, at least one PNA oligomer is coupled to a primary antibody. In some embodiments, at least one PNA oligomer is coupled to a secondary antibody. In this context, in some embodiments, n presents the number of PNA oligomers (including linker, PNA sequence, and label as appropriate) coupled to the antibody (either primary or secondary). In some embodiments, n is an integer ranging from 1 and 10. In other embodiments, n is an integer ranging from 1 and 8. In yet other embodiments, n is an integer ranging from 1 and 6. In yet other embodiments, n is an integer ranging from 2 and 6. In yet other embodiments, n is an integer ranging from 1 and 4. In yet other embodiments, n is an integer ranging from 2 and 4.

The number of PNA oligomers which may be coupled to any particular primary or secondary antibody depends, of course, on the particular antibody selected and its physical and/or chemical properties. In some embodiments, a degree of labeling of the number of oligomers per antibody ranges from between about 2 and about 10. In other embodiments, the degree of labeling is greater than about 1. In other embodiments, the degree of labeling ranges from about 2 to about 6. In yet other embodiments, the degree of labeling is about 4. Without wishing to be bound by any particular theory, it is believed that a relatively low degree of labeling prevents or mitigates any deleterious effects on antibody functionality (e.g. antigen binding or long-term stability of the labeled antibody). Again, without wishing to be bound by any particular theory, it is believed that antibody stability is largely dependent on the antibody itself. Thus, the number of PNA conjugates per antibody may depend on the ability of antibody to tolerate functionalization. Indeed, it is even possible to include PNA conjugates comprising multiple labels. For example, you can have a fluorophore and hapten, whereby, in some embodiments, the hapten can be used for detection whereas the fluorophore can be used to monitor the binding of the PNA to the antibody.

The PNA oligomers may be coupled to any portion of the antibody. Three functional groups in antibodies are the sites for covalent modifications: amines (—NH2), thiol groups (—SH) and carbohydrate residues (Shrestha D, et al, 2012). As such, any of the PNA oligomers disclosed herein may be coupled to amine residues, thiol residues, and carbohydrate residues or any combination thereof. In some embodiments, the PNA oligomers are coupled to Fc portions of the antibody. In other embodiments, the PNA oligomers are coupled to the hinge regions of the antibody. In some embodiments, the PNA oligomers are coupled to one or more of the Fc regions of the antibody and one or more of the hinge regions of the antibody. Indeed, any combination is contemplated by the present disclosure.

Amino group are generally favored primarily because of the abundance of these moieties in the antibody. However, the randomness of amino groups poses a risk that the antibody may become deactivated. (Adamczyk M, et al, 1999, Bioconjug Chem; Jeanson A, et al, 1988, J Immunol Methods; Vira S, et al, 2010, Anal Biochem; Pearson J E et al, 1998, J Immunol Methods). In some embodiments, one or more PNA oligomers are coupled to amino groups of an antibody.

On the other hand, and under appropriate reaction conditions, sulfhydryl labeling offers high specificity targeting of the disulfide bonds between the two heavy chains of the antibody in the hinge region. Since the hinge region is distant from the antigen binding site, this modification is believed to better preserve antibody's binding affinity. In some embodiments, one or more PNA oligomers are coupled to thiol groups of an antibody.

Conjugations at the carbohydrate moieties present in the Fc part of the antibody are similar to that of thiol group, such that modification occurs at a —CHO group distant from the antigen binding site. Again, without wishing to be bound by any particular theory, it is believed that conjugation at the carbohydrate offers less of a negative impact on an antibody's binding affinity. The degree of labeling varies depending on the glycosylation status of a specific antibody. However, loss in antibody affinity was still reported by Jeanson A, et al, 1988, J Immunol Methods. In some embodiments, one or more PNA oligomers are coupled to carbohydrate groups of an antibody.

In another aspect of the present disclosure are conjugates having the structure of Formula (II):

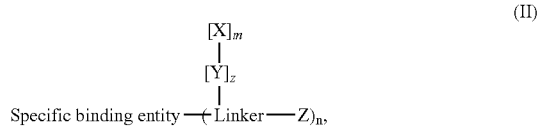

(II)

wherein

'Specific binding entity' is selected from the group consisting of an antibody, an antibody fragment, a drug/antibody complex, and a nucleic acid;

'Linker' is a branched or unbranched, linear or cyclic, substituted or unsubstituted, saturated or unsaturated, group having between 2 and 80 carbon atoms, and optionally having one or more heteroatoms selected from O, N, or S;

Z is selected from the group consisting of a PNA sequence, an uncharged DNA sequence, and a DNA sequence comprising charged and uncharged bases;

X is a label;

Y is a spacer;

m is 0 or an integer ranging from 1 to 6;

z is 0 or 1; and n is an integer ranging from 1 to 12.

In some embodiments, Z comprises a DNA sequence comprising only uncharged DNA bases. In some embodiments, Z comprises a DNA sequence comprising a mixture of charged and uncharged bases. In some embodiments, Z comprises a DNA sequence in which at least 50% of the bases in the DNA sequence are uncharged.

In some embodiments, the PNA sequence comprises between about 5 and 60 bases. In some embodiments, the PNA sequence comprises between about 5 and 30 bases. In some embodiments, the PNA sequence comprises between about 5 and 20 bases. In some embodiments, the PNA sequence comprises between about 5 and 15 bases. In some embodiments, the PNA sequence comprises between about 5 and 10 bases. In some embodiments, the PNA sequence comprises about 15 bases. In some embodiments, the PNA sequence comprises about 10 bases.

In some embodiments, the PNA conjugates comprise a linker, e.g. a multi-functional linker, designed to couple the specific binding moiety to a PNA oligomer. In some embodiments, the multi-functional linker is a hetero-bifunctional linker, i.e. one comprising at least two different reactive functional groups (see, for example, the groups A and B defined herein). For example, a hetero-bifunctional linker may comprise a carboxylic acid group and an amine group, where one of the carboxylic acid group or the amine group is capable of forming a bond with one of the specific binding entity or the PNA sequence, and wherein the other of the carboxylic acid group or amine group is capable of forming a bond with another of the specific binding entity or the PNA sequence. In some embodiments, the "Linker" comprises one or more cleavable groups.

In some embodiments, the PNA can be designed to be coupled directly to the antibody. In other embodiments, the linker may be used to not only conjugate the PNA to the antibody but also to introduce novel functionality, such as chemical cleavage sites, as described further herein. In some embodiments, a mixture of direct conjugation (non-cleavable) and indirect (through a linker, cleavable) of different or the same PNA sequences can be applied on an antibody.

In general, and as noted above, 'Linker' is a branched or unbranched, linear or cyclic, substituted or unsubstituted, saturated or unsaturated, group having between 2 and 80 carbon atoms, and optionally having one or more heteroatoms selected from O, N, or S. While Linkers, including cleavable linkers, will be described in more detail herein, in general the Linkers contemplated herein have a molecular weight ranging from about 1 g/mol to about 3000 g/mol. In other embodiments, the Linkers has a molecular weight ranging from about 20 g/mol to about 200 g/mol. In some embodiments, the Linkers comprises a length ranging from between about 0.5 nm to about 20 nm. In other embodiments, the Linkers comprises a length which is less than about 15 nm. In yet other embodiments, the Linkers comprises a length which is less than about 10 nm.

In some embodiments, the 'Linker' has the structure depicted in Formula (IIIa):

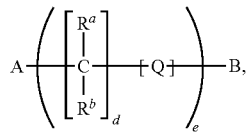 (IIIa)

wherein d and e are integers each independently ranging from 2 to 20; Q is a bond, O, S, or $N(R^c)(R^d)$; $R^a$ and $R^b$ are independently H, a $C_1$-$C_4$ alkyl group, F, Cl, or $N(R^c)(R^d)$; and $R^d$ are independently $CH_3$ or H; and A and B are independently a branched or unbranched, linear or cyclic, substituted or unsubstituted, saturated or unsaturated group having between 1 and 12 carbon atoms and optionally having one or more O, N, or S heteroatoms. In some embodiments, d and e are integers ranging from 2 to 6. In some embodiments, and as described in further detail herein, at least one of A or B comprises a cleavable moiety.

In some embodiments, the 'Linker' has the structure depicted in Formula (IIIb):

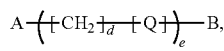 (IIIb)

wherein
d and e are integers each independently ranging from 2 to 20;
Q is a bond, O, S, or $N(R^c)(R^d)$;
$R^c$ and $R^d$ are independently $CH_3$ or H; and
A and B are independently a branched or unbranched, linear or cyclic, substituted or unsubstituted, saturated or unsaturated group having between 1 and 12 carbon atoms and optionally having one or more O, N, or S heteroatoms.

In some embodiments, the "Linker" has the structure depicted in Formula (IIIc):

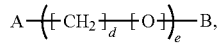 (IIIc)

wherein
d and e are integers each independently ranging from 2 to 20;
A and B are independently a branched or unbranched, linear or cyclic, substituted or unsubstituted, saturated or unsaturated group having between 1 and 12 carbon atoms and optionally having one or more O, N, or S heteroatoms. In other embodiments, d and e are integers ranging from 2 to 15. In other embodiments, d and e are integers ranging from 2 to 10. In yet other embodiments, d and e are integers ranging from 2 to 6.

In some embodiments, the 'Linker' comprises solubilizing groups, such as polyethylene glycol (PEG) groups, to increase the water solubility of the PNA conjugates. In some embodiments, the Linkers comprises between about 2 and about 24 PEG groups. In some embodiments, the Linkers comprises between about 2 and about 18 PEG groups. In other embodiments, the Linkers comprises between about 2 and about 12 PEG groups. In yet other embodiments, the Linkers comprises between about 2 and about 6 PEG groups. In yet other embodiments, the Linkers comprises 4 PEG groups. In yet other embodiments, the linker comprises 8 PEG groups. In yet other embodiments, the Linkers comprises 12 PEG groups. In yet other embodiments, the Linkers comprises 16 PEG groups. In yet other embodiments, the Linkers comprises 24 PEG groups. Without wishing to be bound by any particular theory, it is believed that the incorporation of such alkylene oxide linkers is believed to increase the hydrophilicity of the PNA conjugate. A person of ordinary skill in the art will appreciate that as the number alkylene oxide repeat units in the linker increases, the hydrophilicity of the PNA conjugate also may increase. Additional heterobifunctional polyalkyleneglycol linkers useful for practicing certain disclosed embodiments of the present disclosure are described in assignee's co-pending applications, including "Nanoparticle Conjugates," U.S. patent application Ser. No. 11/413,778, filed Apr. 28, 2006; "Antibody Conjugates," and U.S. application Ser. No. 11/413,415, filed Apr. 27, 2006.

In some embodiments, A and B include groups that are capable of forming bonds with a group of the specific binding entity or a group of the PNA sequence. In some embodiments, one or both of A or B is a carbonyl-reactive group. Suitable carbonyl-reactive groups include hydrazine, hydrazine derivatives, and amine. In other embodiments, one or both of A or B is an amine-reactive group. Suitable amine-reactive groups include active esters, such as NHS or sulfo-NHS, isothiocyanates, isocyanates, acyl azides, sulfonyl chlorides, aldehydes, glyoxals, epoxides, oxiranes, carbonates, aryl halides, imidoesters, anhydrides and the like. In yet embodiments, one or both of A or B is a thiol-reactive group. Suitable thiol-reactive groups include non-polymerizable Michael acceptors, haloacetyl groups (such as iodoacetyl), alkyl halides, SPDP (succinimidyl 3-(2-pyridyldithio)propionate), maleimides, aziridines, acryloyl groups, vinyl sulfones, benzoquinones, aromatic groups that can undergo nucleophilic substitution such as fluorobenzene groups (such as tetra and pentafluorobenzene groups), and disulfide groups such as pyridyl disulfide groups and thiols activated with Ellman's reagent.

In some embodiments, A and/or B include UV or visible light photocleavable groups. In some embodiments, the UV or visible light photocleavable is selected from the group consisting of Arylcarbonylmethyl Groups (including 4-acetyl-2-nitrobenzyl, Dimethylphenacyl (DMP), 2-(Alkoxymethyl)-5-methyl-a-chloroacetophenones, 2,5-Dimethylbenzoyl Oxiranes, and Benzoin groups: 3',5'-dimethoxybenzoin (DMB)), O-Nitrobenzyl Groups (including 1-(2-nitrophenyl)ethyl (NPE), 1-(Methoxymethyl)-2-nitrobenzene, 4,5-dimethoxy-2-nitrobenzyl (DMNB); α-carboxynitrobenzyl (α-CNB), o-Nitro-2-phenethyloxycarbonyl Groups, including 1-(2-nitrophenyl)ethyloxycarbonyl and 2-Nitro-2-Phenethyl Derivatives, and o-Nitroanilides such as Acylated 5-Bromo-7-Nitroindolines); Coumarin-4-ylmethyl Groups (including 7-Methoxycoumarin Derivatives); and Arylmethyl Groups (including o-Hydroxyarylmethyl Groups).

In other embodiments, A and/or B include near-infrared photocleavable groups. Suitable near-infrared photocleavable groups include cyanine groups, including C4-dialkylamine-substituted heptamethine cyanines. Without wishing to be bound by any particular theory, it is believed that the incorporation of a photocleavable linker allows spatial control over the PNA release and ultimately a quantitative measurement of the marker expression.

In yet other embodiments, A and/or B include chemically cleavable groups that may be cleaved by different chemical reactants, including reducing agents or by induced changes in pH. Suitable chemically cleavable groups include disulfide-based groups; diazobenzene groups (including 2-(2-alkoxy-4-hydroxy-phenylazo) benzoic acid scaffolds, sensitive to sodium dithionite); ester bond-based groups (high pH); and acidic sensitive linkers (such as dialkoxydiphenylsilane linker or acylhydrazone). A vicinal diol cleavable linker may be cleaved by $NaIO_4$, such as described in "A simple and effective cleavable linker for chemical proteomics applications," Mol Cell Proteomics, 2013 January; 12(1):237-44. doi: 10.1074/mcp.M112.021014. Epub 2012 Oct. 1. In yet further embodiments, A and/or B include enzymatically cleavable linkers. Suitable enzymatically cleavable groups include trypsin cleavable groups and V8 protease cleavable groups.

In some embodiments, the multi-functional linker is selected from one which may be orthogonally protected and deprotected, allowing the skilled artisan to conjugate one of the specific binding entity or PNA moiety at a time to the multi-functional linker, thus preventing unwanted side reactions or side products.

In some embodiments, Y is a branched or unbranched, linear or cyclic, substituted or unsubstituted, saturated or unsaturated group having between 1 and 12 carbon atoms and optionally having one or more O, N, or S heteroatoms. In some embodiments, Y comprises a cleavable group, such as those described above with regard to 'Linkers.'

In some embodiments, X is selected from haptens, fluorophores, chromogens, enzymes, ligands, phosphorescent or chemiluminescent agents, quantum dots, mass spectrometry tags or any other suitable entity. The type of label selected depends on the PNA oligomer or PNA conjugate being synthesized and the PNA conjugate's ultimate role after conjugation to an appropriate specific binding entity. For example, in some embodiments labels may be chosen such that when the PNA oligomers are conjugated to an antibody, the labels may be directly detected (e.g. fluoresceins or fluorescein derivatives or analogs). In other embodiments, labels may be selected such that when the PNA oligomers are conjugated to an antibody, the labels may be indirectly detected (e.g. detection of a hapten label by using a secondary antibody specific for the hapten, where the secondary antibody is conjugated to a detectable moiety). Guidance in the choice of labels appropriate for various purposes are discussed, for example, in Sambrook et al., Molecular Cloning: A Laboratory Manual, Cold Spring Harbor Laboratory Press (1989) and Ausubel et al., Current Protocols in Molecular Biology, Greene Publishing Associates and Wiley-Intersciences (1987), the disclosures of which are incorporated herein by reference.

Fluorophores belong to several common chemical classes including coumarins, fluoresceins (or fluorescein derivatives and analogs), rhodamines, resorufins, luminophores and cyanines. Additional examples of fluorescent molecules can be found in The Handbook—A Guide to Fluorescent Probes and Labeling Technologies, Molecular Probes, Eugene, Oreg.

Where the label includes an enzyme a detectable substrate (i.e. a substrate of the enzyme) such as a chromogenic moiety, a fluorogenic compound, or a luminogenic compound can be used in combination with the enzyme to generate a detectable signal (a wide variety of such compounds are commercially available, for example, from Invitrogen Corporation, Eugene Oreg.). Particular examples of chromogenic compounds/substrates include diaminobenzidine (DAB), 4-nitrophenylphospate (pNPP), fast red, bromochloroindolyl phosphate (BCIP), nitro blue tetrazolium (NBT), BCIP/NBT, fast red, AP Orange, AP blue, tetramethylbenzidine (TMB), 2,2'-azino-di-[3-ethylbenzothiazoline sulphonate] (ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue and tetrazolium violet.

Alternatively, an enzyme can be used in a metallographic detection scheme. Metallographic detection methods include using an enzyme such as alkaline phosphatase in combination with a water-soluble metal ion and a redox-inactive substrate of the enzyme. In some embodiments, the substrate is converted to a redox-active agent by the enzyme, and the redox-active agent reduces the metal ion, causing it to form a detectable precipitate. (see, for example, U.S. patent application Ser. No. 11/015,646, filed Dec. 20, 2004, PCT Publication No. 2005/003777 and U.S. Patent Application Publication No. 2004/0265922; each of which is incorporated by reference herein). Metallographic detection methods include using an oxido-reductase enzyme (such as horseradish peroxidase) along with a water-soluble metal ion, an oxidizing agent and a reducing agent, again to for form a detectable precipitate. (See, for example, U.S. Pat. No. 6,670,113, which is incorporated by reference herein).

Examples of haptens are disclosed herein. An example of using mass spectrometry to analyze PNA sequences is described in "Peptide nucleic acid characterization by MALDI-TOF mass spectrometry," Anal Chem. 1996 Sep. 15; 68(18):3283-7.

In some embodiments, the X is selected from the group consisting of di-nitrophenyl, biotin, digoxigenin, fluorescein, rhodamine, or combinations thereof. In other embodiments, the X is selected from the group consisting of oxazoles, pyrazoles, thiazoles, nitroaryls, benzofurans, triterpenes, ureas, thioureas, rotenoids, coumarins, cyclolignans, or combinations thereof. In yet other embodiments, the X is selected from the group consisting of 5-nitro-3-pyrazole carbamide, 2-(3,4-dimethoxyphenyl)quinoline-4-carboxylic acid), 3-hydroxy-2-quinoxalinecarbamide, 2,1,3-benzoxadiazole-5-carbamide, and 2-acetamido-4-methyl-5-thiazolesulfonamide. In yet other embodiments, X may be selected from any of the haptens, chromophores, fluorophores, and enzymes which are described further herein (see, e.g. those listed as "reporter moieties" herein).

Of course, in some embodiments, the PNA conjugates do not comprise any label, i.e. the PNA oligomer portion of the PNA conjugate terminates in a nucleotide.

Synthesis of PNA Conjugates

Figure 19:
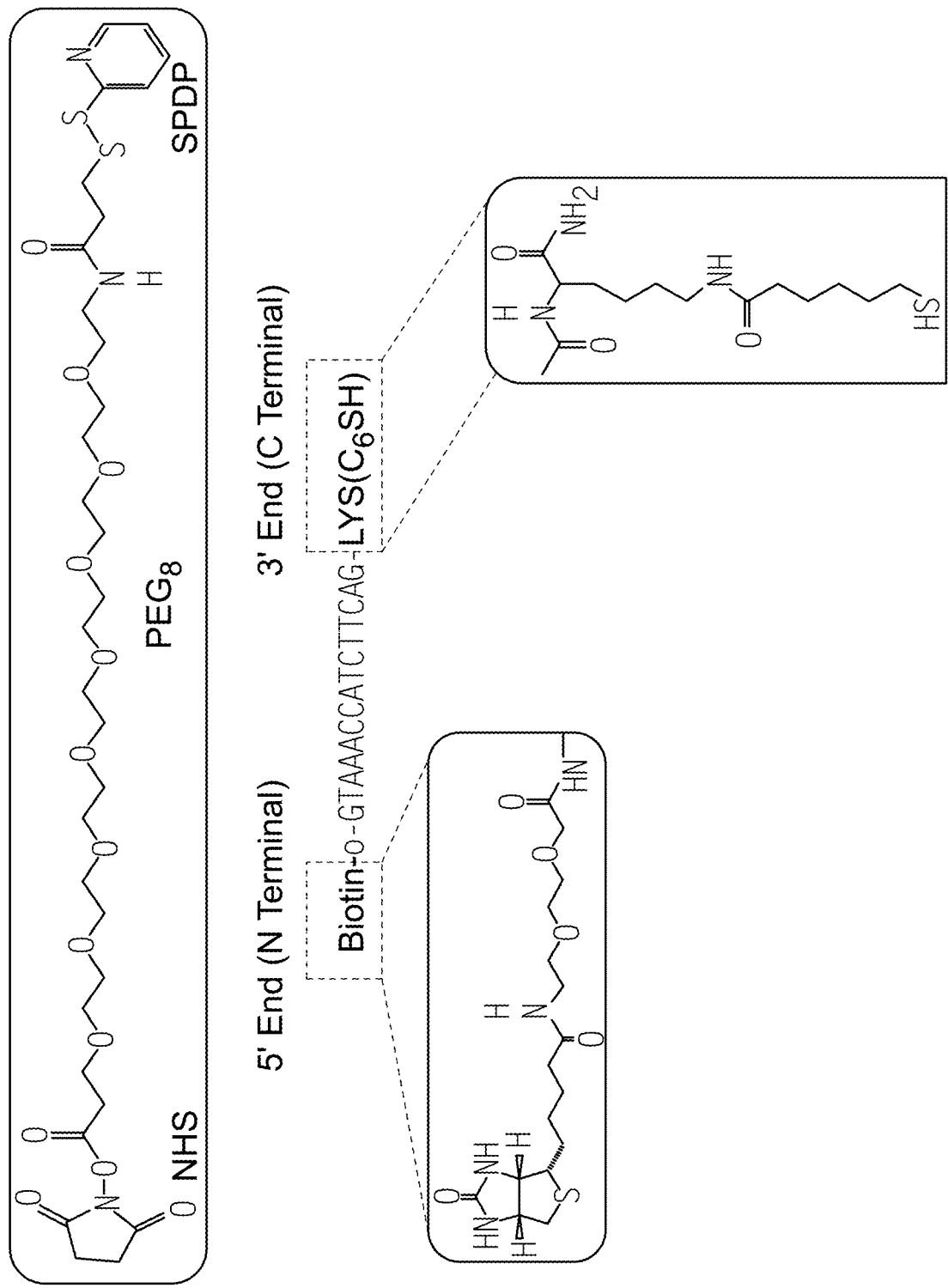
FIG. 19 provides the chemical structure of the heterobifunctional cross-linker and PNA sequence.
Figure 20:
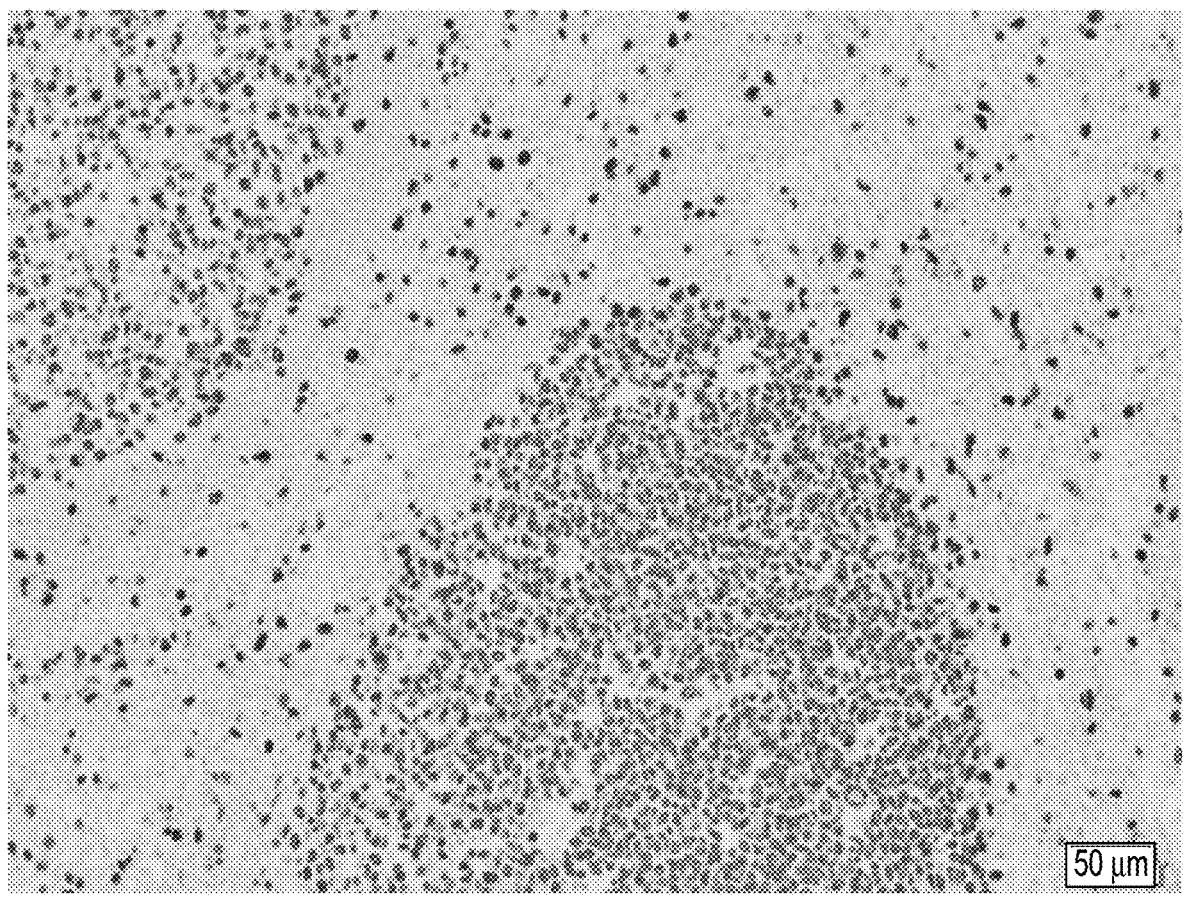
FIG. 20 illustrates tonsil tissue incubated with anti-Ki67 then a GAR-short PNA (sequence shown in previous slide) and detected with SA-HRP. Detection of the biotin on the short PNA sequence. The images show that short PNA is successfully conjugated on the Ab.
Figure 21:
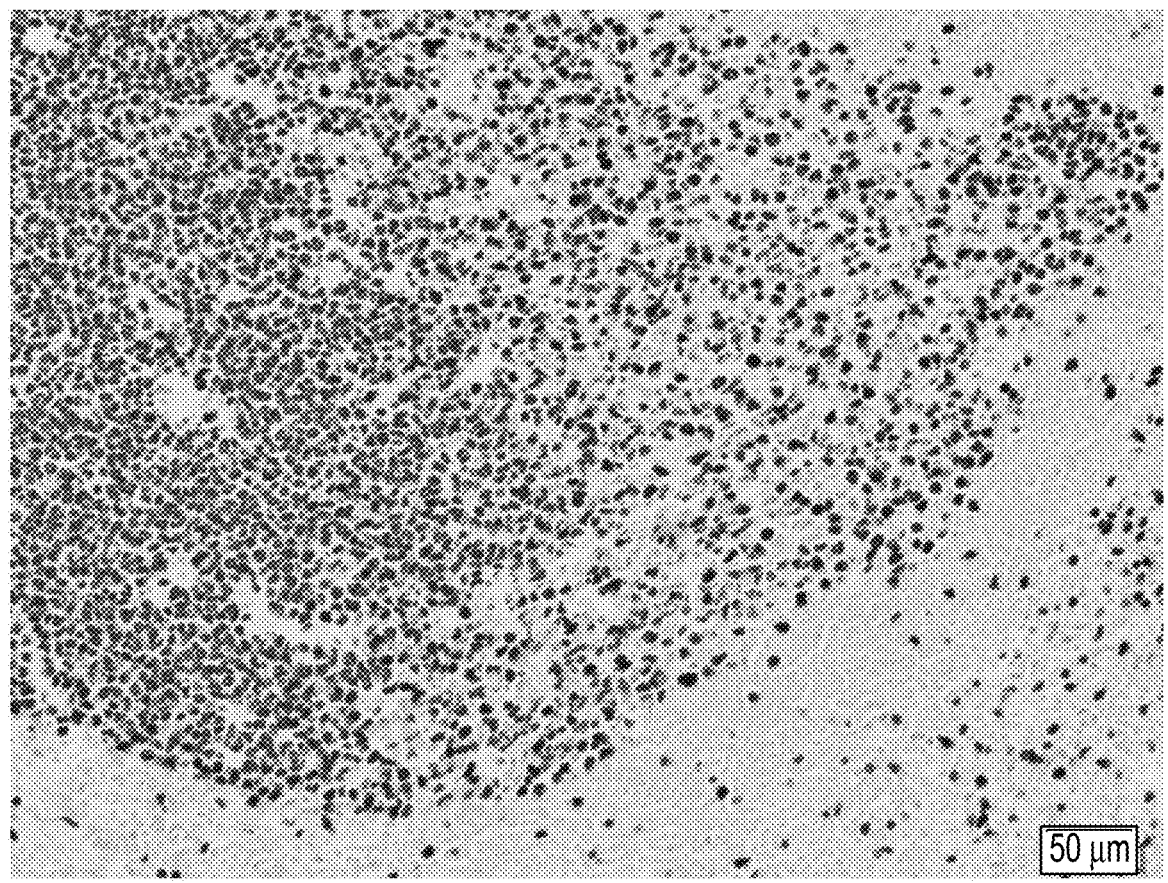
FIG. 21 illustrates tonsil tissue incubated with anti-Ki67 then GAR-HRP. The images show that short PNA is successfully conjugated on the Ab. This is used to compare standard detection (21) to GAR-short PNA based detection
Figure 22A:
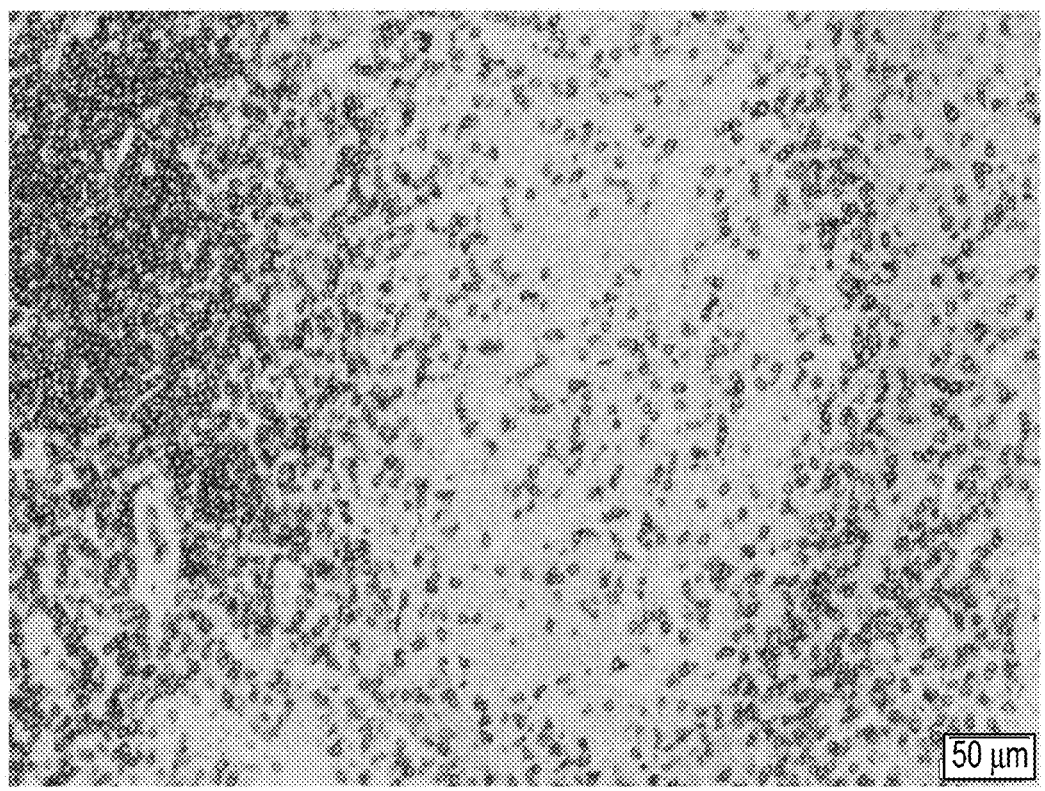
FIG. 22A illustrates tonsil incubated with CD3-shortPNA and detected with SA-HRP. IHC of short PNA conjugated with primary antibody. The concentration of the Ab-short PNA conjugate used was 5 ug/mL (PNA sequence: Biotin-o-CCATCTTCAG-MAL sequence (SEQ ID NO: 19)).
Figure 22B:
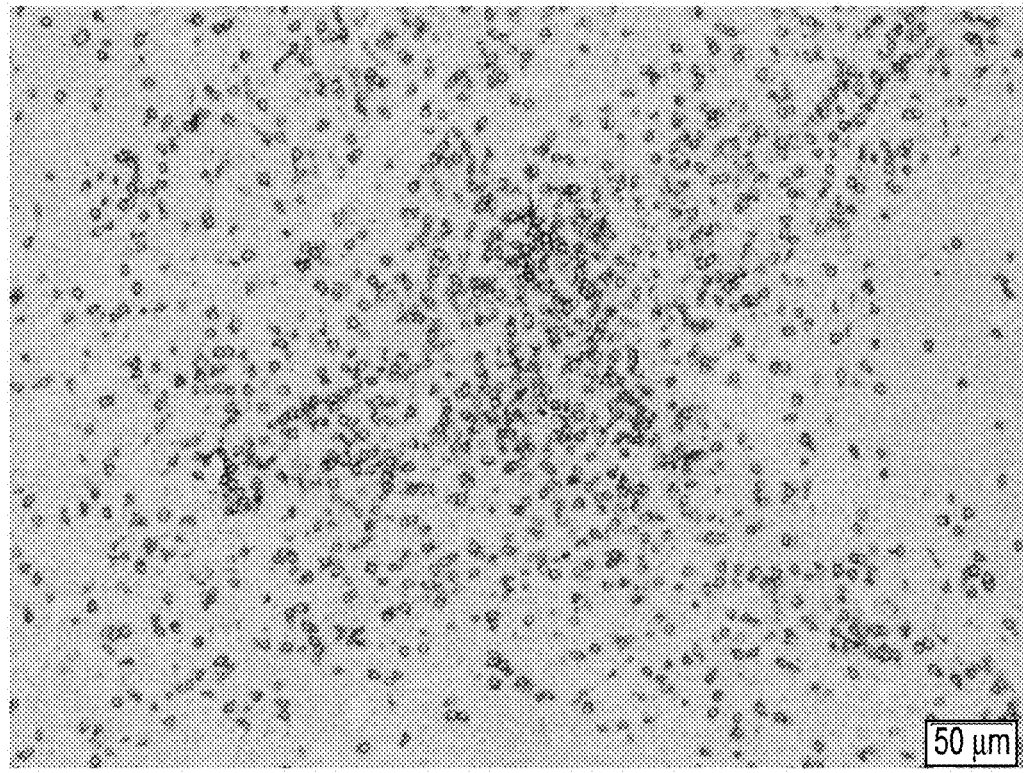
FIG. 22B provides a second example of a primary antibody-short PNA conjugate (CD8-shortPNA).
Figure 22C:
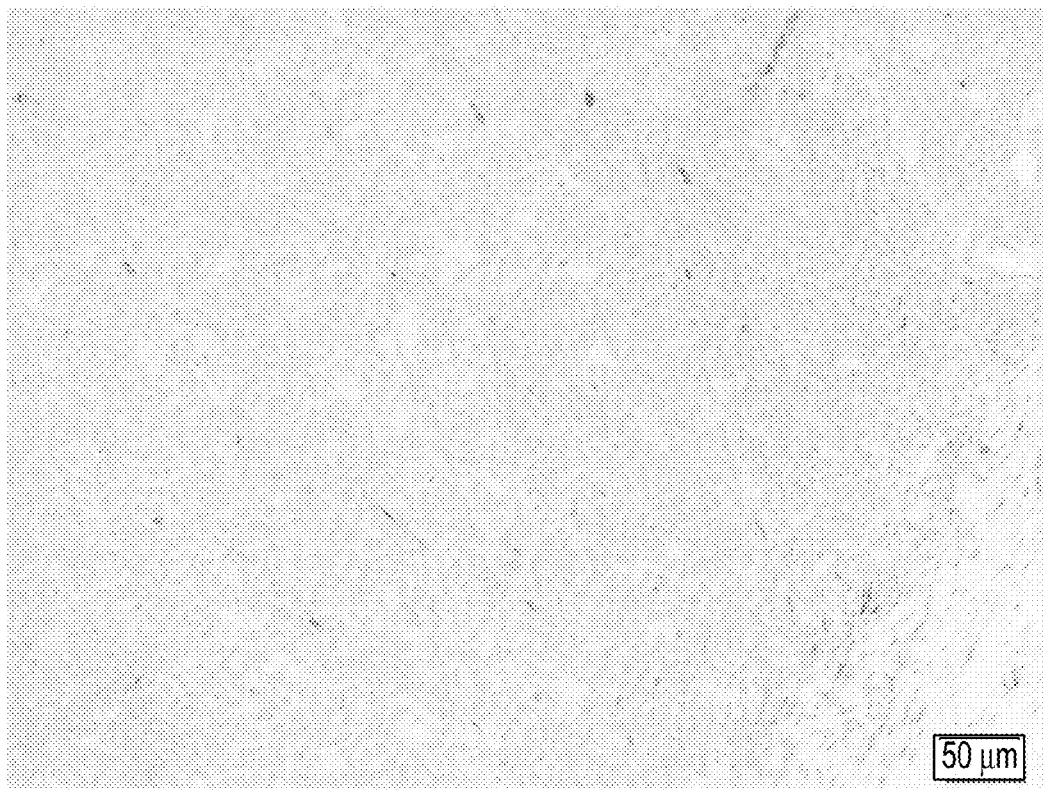
FIG. 22C provides a third example of a primary antibody-short PNA conjugate (CD34-shortPNA).
Figure 22D:
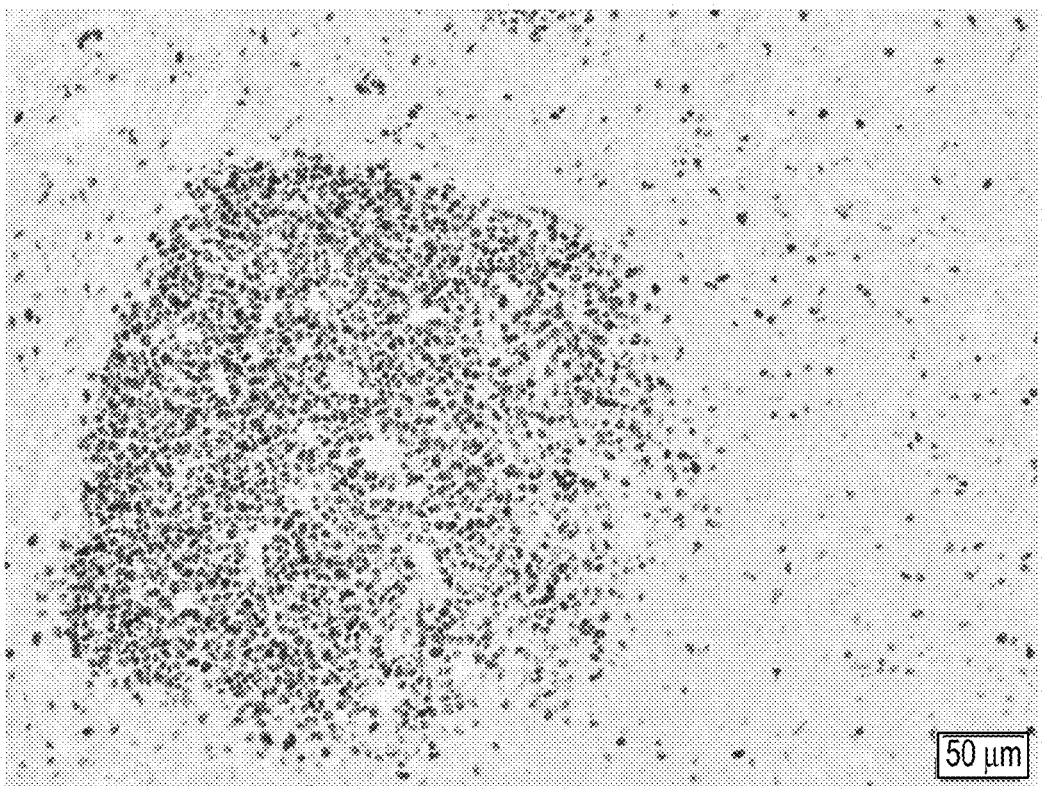
FIG. 22D provides a fourth example of a primary antibody-short PNA conjugate (Ki67-shortPNA).
Figure 23:
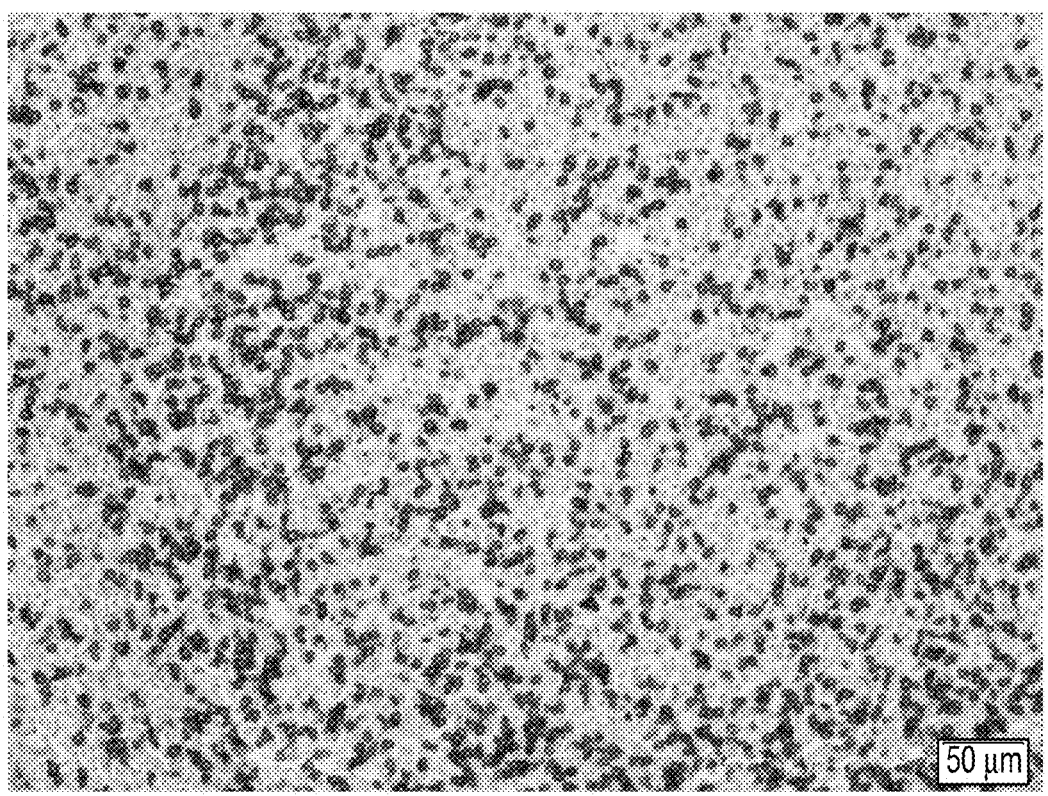
FIG. 23 illustrates a CD3-short PNA2 having the sequence: Biotin-o-TTAGTCCAAC-Lys(SMCC) (SEQ ID NO: 20).
Figure 24:
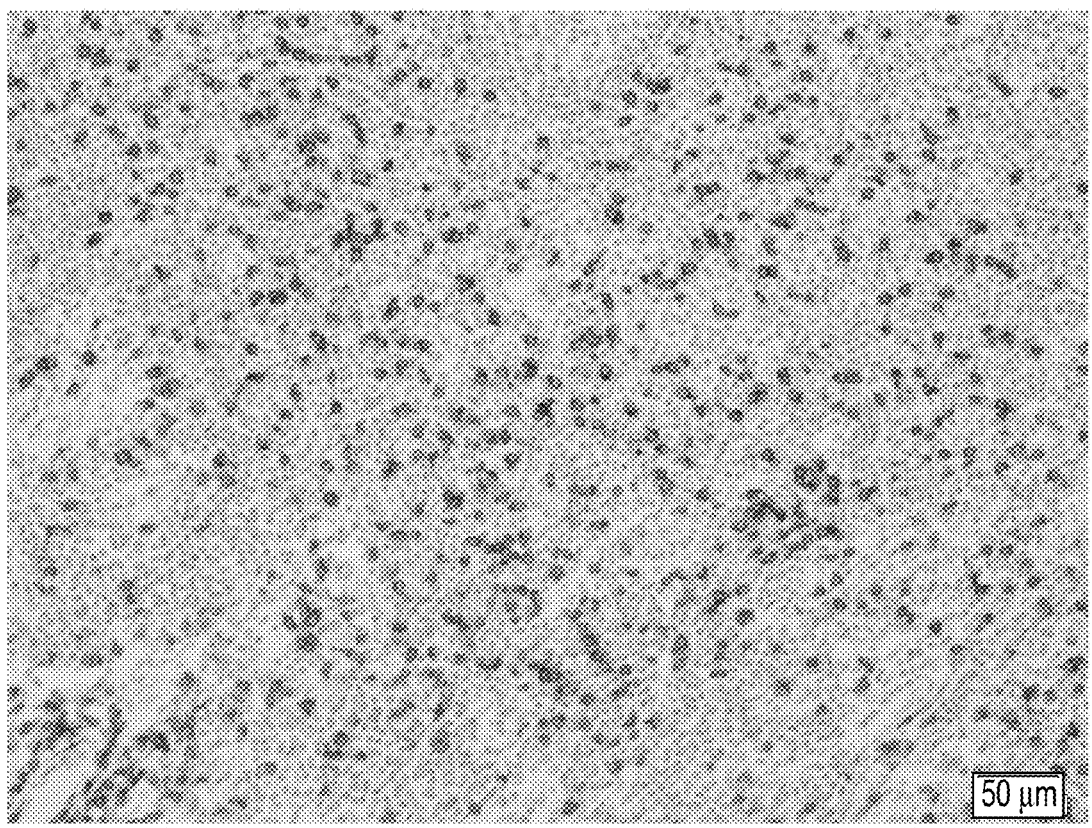
FIG. 24 illustrates CD8 conjugated to sPNA2, where the PNA sequence was Biotin-o-TTAGTCCAAC-Lys(SMCC) (SEQ ID NO: 20).
Figure 26:
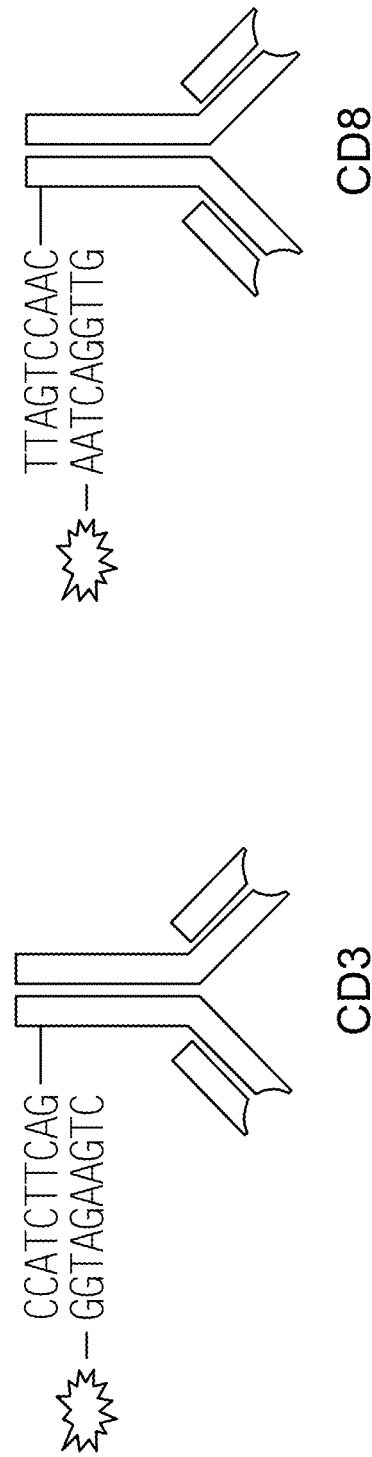
FIG. 26 illustrates fluorescent duplexing via DNA conjugation. The figure further illustrates detection through hybridization but this time through florescence. The complementary DNA includes one or more fluorescent tags. Two primary antibodies CD3 and CD8, are conjugated, respectively, to two different short PNA tags. Each of the two complementary DNA sequences have a fluorophore.
Figure 27A:
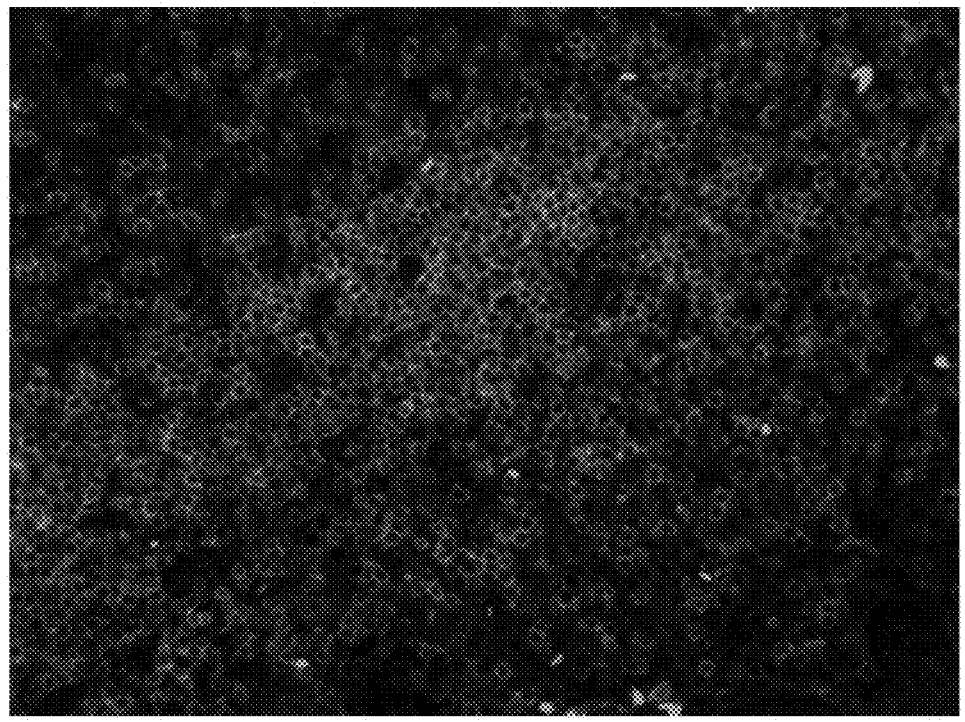
FIGS. 27A, 27B, and 27C illustrate tonsil tissue slide incubated with a mixture of anti-CD3-shortPNA1 and anti-CD8-shortPNA2 (anti-CD3 and antiCD-8 conjugated to short PNA1 and short PNA2 respectively) followed by incubation with 2 DNA sequences Tonsil_CD3-sPNA1+CD8-sPNA2 AB15+AB19, where the mixture of DNA 15 and DNA 19 (DNA15 AB15 is complementary to sPNA1 and has AlexaFluo 488 on its end, while AB19 is complementary to sPNA2 and has a AlexaFluo 647 on its end). The fluorescently stained tissue is imaged with a fluorescent microscope. The green channel (FIG. 27A) shows AlexaFluo 488 on the CD3 labeled antibody. The Red channel (FIG. 27B) shows the AlexaFluo 647 on the CD8 labeled Ab at the same field of view. A merge of the two images (FIG. 27C) shows that all color red cells (CD8) are also green (CD3) because all the cells that express CD8 do express CD3. Some green cells are not red because not all CD3 cells are CD8. CD8 is s subpopulation of CD3.
Figure 27B:
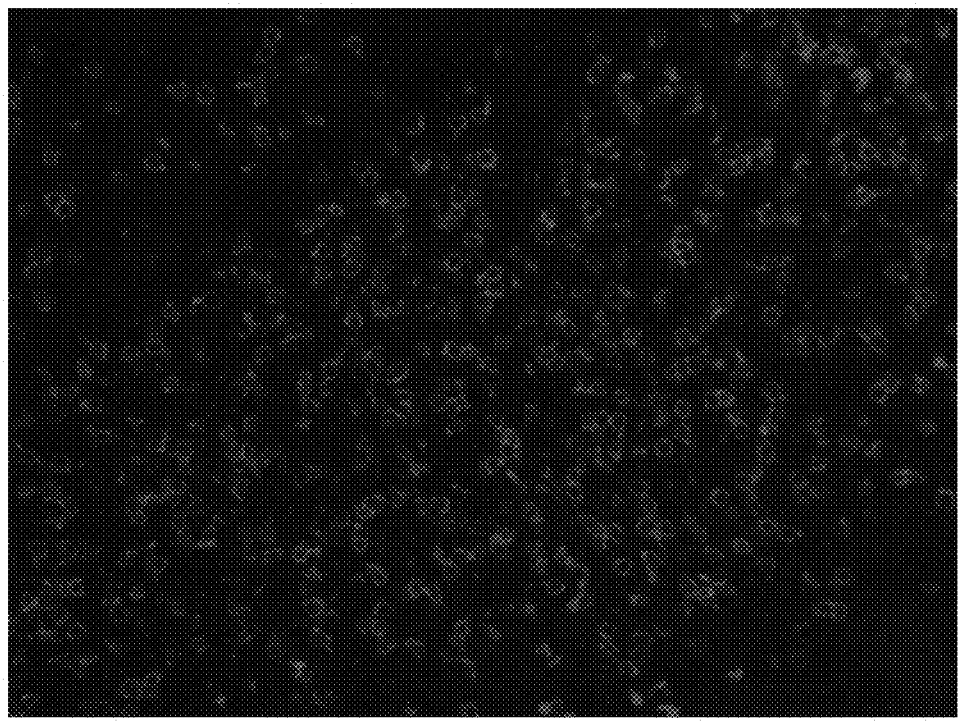
Figure 27C:
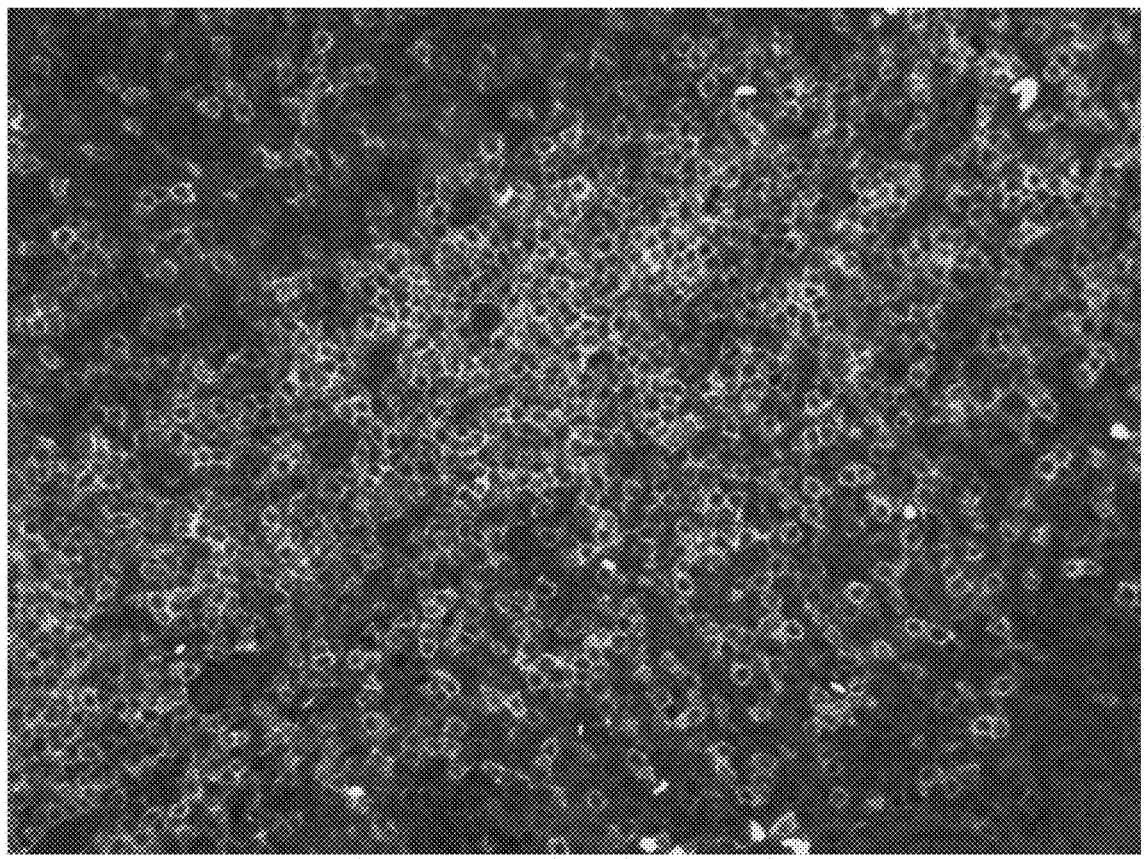
Figure 28:
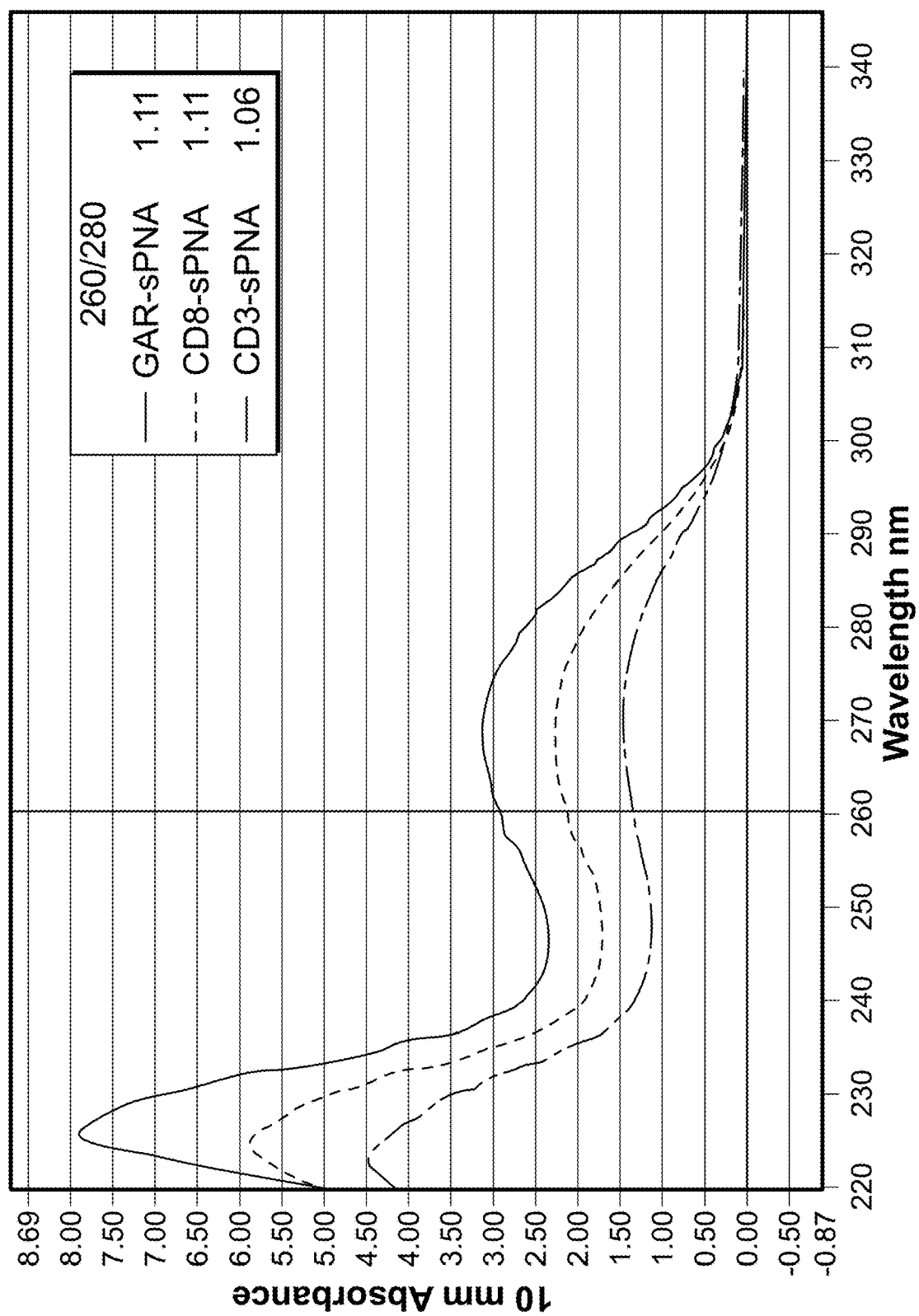
FIG. 28 illustrates the UV absorbance of GAR, CD3 and CD8-shortPNA conjugates with 260/280 ratios. It is shown that the 260 nm/280 nm ratio increases as PNA is conjugated to the antibody.

The PNA conjugates may be synthesized by any means known to know of ordinary skill in the art. In some embodiments, a PNA oligomer is coupled to a specific binding entity through a heterobifunctional cross-linker, such as a cross-linker bearing a NHS ester group (e.g. SPDP-PEGS-NHS) as illustrated in FIG. 19. Examples of heterobifunctional cross-linkers include DBCO-PEGn-maleimide illustrated in FIG. 16, DBCO-PEGn-NHS, N3-PEGn-NHS, or N3-PEGn-maleimide (where n ranges from 0 to 20). Non-limiting examples of PNA sequences suitable for conjugation include the following:

SEQ ID NO: 8:
5'-Biotin-o-GTCAACCATCTTCAG-Lys(C6SH)-3'

SEQ ID NO: 9:
5'-Biotin-o- TTAGTCCAACTGGCA-Lys(C6SH)-3'

SEQ ID NO: 10:
5'-Biotin-o-CATTCAAATCCCCGA-PL-Lys(C6SH)-3'

SEQ ID NO: 11:
5'-Biotin-o-CTGAAGATGGTTTAC-Lys(C6SH)-3'

SEQ ID NO: 12:
5'-Alexa488-o-CATCCTGCCGCTATG-Lys(C6SH)-3'

SEQ ID NO: 13:
5'-Biotin-o-GTCAACCATCTTCAG-Arg-o-Cys-3'

While the size PNA sequences identified above each have 15 bases, the skilled artisan will appreciate that PNA sequences that are similarly functionalized may comprise any number of bases, e.g. 10 bases. For example, the PNA sequence may be: sPNA4: Biotin-o-CCATCTTCAG-Lys (C6SH) (SEQ ID NO: 21).

In some embodiments, a NHS side of a cross-linker is used to bind to an amine group of an antibody to form an amide bond; whereas a (succinimidyl 3-(2-pyridyldithio) propionate) ("SPDP") side of the cross-linker reacts with a sulfhydryl group at the 3' end (C terminal) of a PNA sequence forming a disulfide bond. In some embodiments, the disulfide bond can then be chemically cleaved with a reducing agent.

Figure 10:
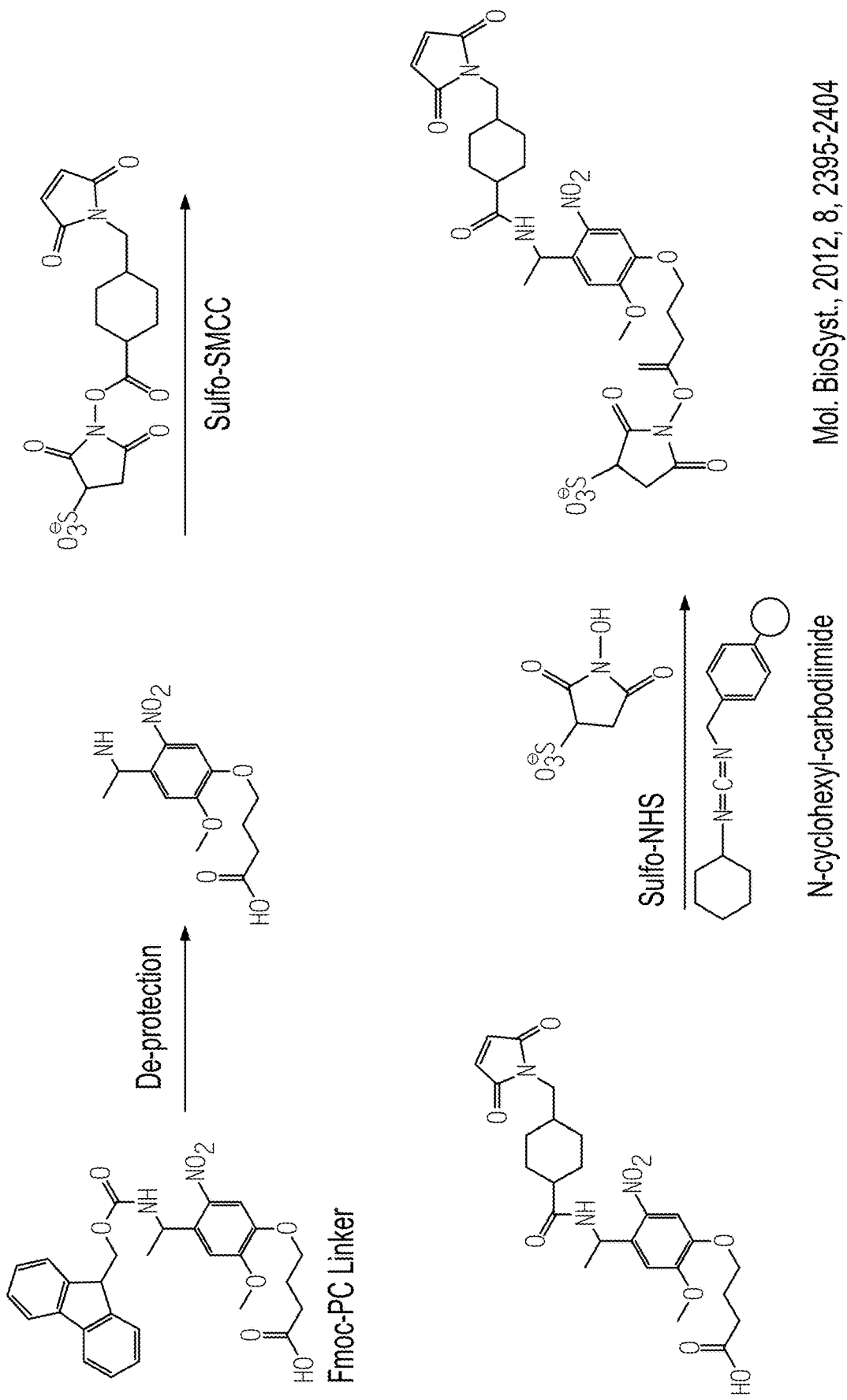
FIG. 10 illustrates a possible synthetic scheme of the photocleavable heterobifunctional cross-linker.

As described herein, in some embodiments, the cleaved PNA sequence may be detected and measured with the NanoString nCounter platform. For example, the PNA sequence may include a biotin on the 5' end (N terminal) to enable direct immobilization on the streptavidin surface without the need of a capture strand (FIG. 19). This modification is expected to enable the use of much shorter PNA sequence (about 15 bases) to be hybridized directly to the reporter strand and further analyzed by the nCounter platform. In some embodiments, a PNA sequence having about 15 bases provides enough binding affinity and specificity to the reporter sequence during the detection. Without wishing to be bound by any particular theory, it is believed that the Tm of a 15-mer PNA-DNA complex is similar to 50-mer DNA-DNA complex. Examples of suitable PNA sequences for coupling are provided below:

In some embodiments, a photocleavable (PC) linker can be incorporated between PNA sequence and the specific binding entity (e.g. an antibody) (see the groups identified as A or B defined herein) to allow light-triggered release of the PNA. In some embodiments, the PNA sequence can be synthesized with the PC linker: Biotin-o-CATT-CAAATCCCCGA-PC-Lys(C6H) (SEQ ID NO: 22). Following light irradiation, the PNA sequence may be released intact and may be measured using any of the techniques described herein. Alternatively, a PC bifunctional linker can be synthesized (FIG. 10) and used to link the PNA to the antibody. Multiple PNA oligomers (same sequences or different sequences) can be conjugated to an antibody via different linkers such as certain PNA sequence is cleavable and certain sequence is not or part of the same PNA sequence is cleavable and the other part is not.

The approach of incorporating the photocleavable liker within the PNA during the synthesis of the PNA conjugate is advantageous as it is more time and cost effective and ensures that the photocleavable linker is incorporated in all the PNA oligomers. Alternatively, a photocleavable bifunctional linker can be synthesized (FIG. 10) and used to link PNA sequences to an antibody. This approach is advantageous as the photocleavable bifunctional linker may be used to link any PNA sequence to an antibody even if the PNA was not designed to be photocleavable. Without wishing to be bound by any particular theory, this approach may provide some flexibility in terms of using the same PNA sequence as normal (not photocleavable) and photocleavable antibody tag. In some embodiments, the disulfide bond is still present in the synthesized photocleavable PNA allowing both light and chemical cleavage. In some embodiments, the biotin moiety is also retained to allow SA-HRP and DAB detection on slides, as noted further herein.

Figure 16:
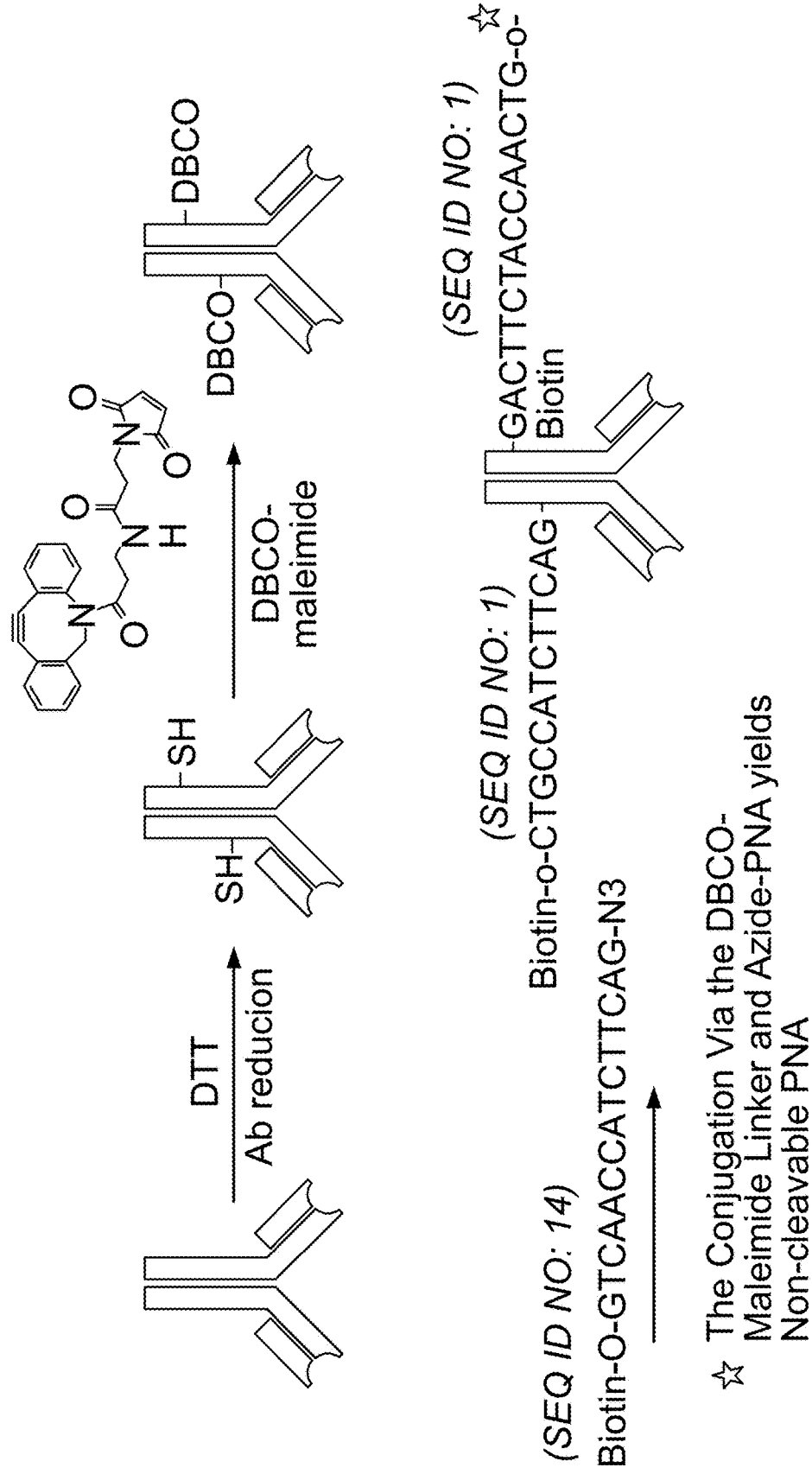
FIG. 16 is a schematic illustrating the conjugation of an antibody to a PNA oligomer, the coupling utilizing "click chemistry." Here, a reduced antibody is functionalized with a DBCO group and then coupled to a PNA oligomer comprising an azide group.

In some embodiments, a PNA sequence may be introduced to the specific binding moiety and/or linker using "click chemistry," such as illustrated in FIG. 16. A non-limiting example of a PNA sequence having a reactive group (e.g. an azide) capable of undergoing a "click" reaction is presented below:

SEQ ID NO: 14:
5'-Biotin-O-GTCAACCATCTTCAG-Lys(eg3-N3)-3'

The skilled artisan will appreciate that a PNA sequence comprising an appropriate reactive group may form a click adduct with another molecule that is also appropriately functionalized to undergo the "click" reaction. Indeed, the skilled artisan will recognize that for one member of a pair of click conjugates to react with another member of the pair of click conjugates, and thus form a covalent bond, the two members of the pair of click conjugates must have reactive functional groups capable of reacting with each other. The table which follows exemplifies different pairs of reactive functional groups that will react with each other to form a covalent bond.

| Reactive Functional Group on a First Member of a Pair of Click Conjugates | Reactive Functional Group on a Second Member of a Pair of Click Conjugates |
|---|---|
| DBCO | Azide |
| Alkene | Tetrazine |
| TCO | Tetrazine |
| Maleimide | Thiol |
| DBCO | 1,3-Nitrone |
| Aldehyde or ketone | Hydrazine |
| Aldehyde or ketone | Hydroxylamine |
| Azide | DBCO |
| Tetrazine | TCO |
| Thiol | Maleimide |
| 1,3-Nitrone | DBCO |
| Hydrazine | Aldehyde or ketone |
| Hydroxylamine | Aldehyde or ketone |
| Tetrazine | Alkene |

Figure 18:
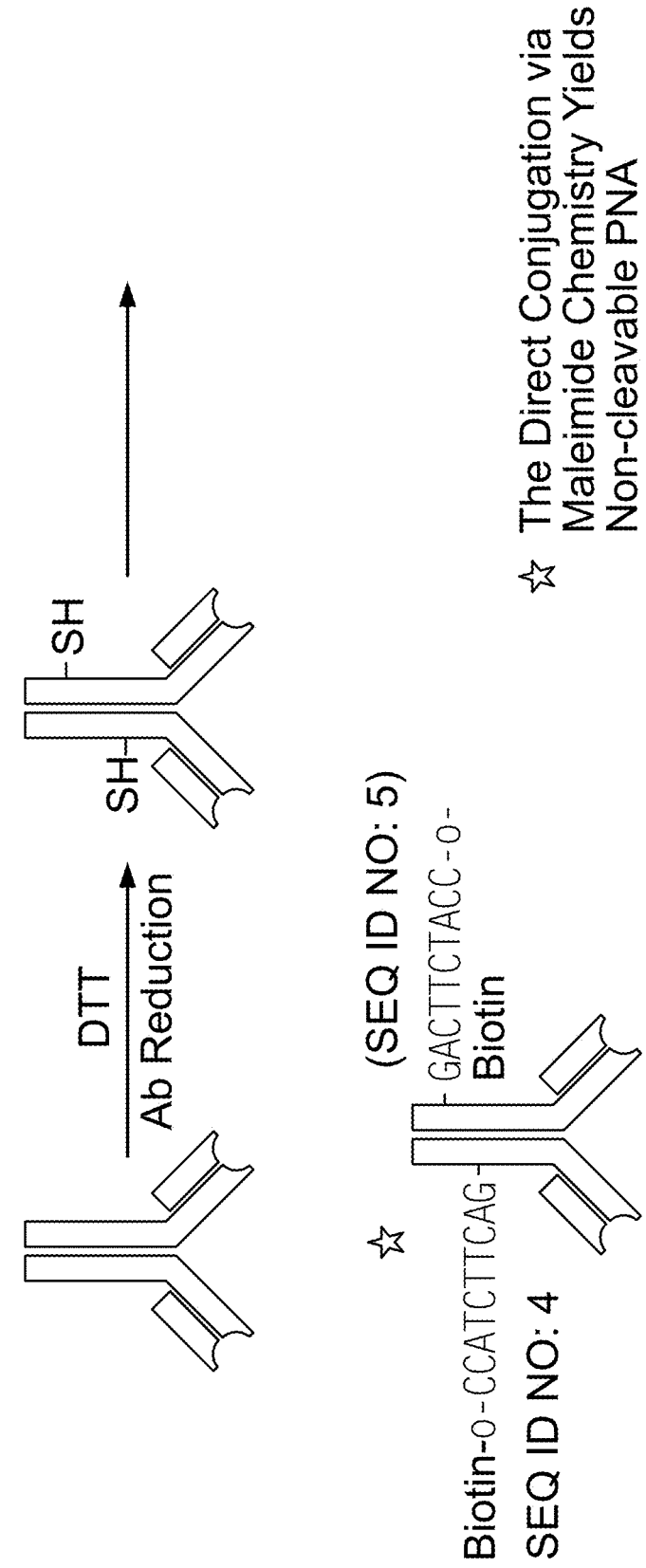
FIG. 18 is a schematic illustrating the conjugation of an antibody to a PNA oligomer via maleimide moiety.

In some embodiments, groups present on an antibody (e.g. a primary or secondary antibody) are reduced in the presence of dithiothreitol ("DTT") so as to provide an antibody having one or more thiol groups. The thiol groups may be reacted with a first member of a pair of click members, the first member bearing a reactive functional group capable of participating in the "click chemistry" reaction (e.g. a DBCO group). The first member of the pair of click conjugates may also comprise a second functional group capable of reacting with the thiolated antibody (e.g. a maleimide). The second functional group on the first member of the pair of click conjugates is one which is not capable of reacting in the click chemistry reaction. As illustrated in FIG. 16, this step allows the antibody to become functionalized with a first reactive functional group capable of participating in the "click chemistry" coupling. A second member of the pair of click members is then introduced, such as a PNA molecule including a second reactive functional group capable of participating in the "click chemistry" reaction (e.g. an azide group). The second member of the pair of click members may also comprise a label or reporter moiety. In the embodiment depicted in FIG. 16, the DBCO group-bearing antibody is able to couple to with the azide group of the second member of the pair of click members, such that the PNA conjugate becomes coupled to the antibody. The PNA conjugated in this procedure is not chemical cleavable or photo-cleavable In some embodiments, a PNA sequence may be introduced to the specific binding moiety and/or linker using "maleimide" chemistry (see FIG. 18). In some embodiments, the PNA conjugated in this procedure is not chemical cleavable or photo-cleavable A non-limiting example of a PNA sequence having a SMCC group is presented below:

```
SEQ ID NO: 15:
5'-Biotin-O-GTCAACCATCTTCAG-Lys(SMCC)-3'
```

Without wishing to be bound by any particular theory, it is believed that the use of click chemistry or maleimide chemistry permits the introduction of shorter PNA sequences, e.g. sequences having 10 or less bases.

Detection of Conjugates

In some embodiments, the conjugate of any of Formulas (I), (IA), (IC), (ID), and (II), may comprise a label that facilitates the direct detection of the conjugate. For example, if the label of the conjugate comprises a fluorophore or a chromophore, the fluorophore or chromophore may be directly detected according to methods known to those of ordinary skill in the art.

In other embodiments, specific reagents are utilized to enable detection of any the conjugates of Formulas (I), (IA), (IC), (ID), and (II), and hence the targets in a tissue sample. In some embodiments, detection reagents are utilized which are specific to the particular label of the conjugate or that are complementary to the nucleotide sequence (e.g. a PNA sequence) of the conjugate, as noted further herein. In some embodiments, the detection reagents comprise a secondary antibody which is specific for the label of the conjugate, i.e. the secondary antibody is an anti-label antibody including, for example, an anti-hapten antibody where the label is a hapten.

In some embodiments, the secondary antibody or anti-label antibody may be conjugated to a "reporter moiety" to effectuate detection of the conjugate of Formulas (I), (IA), (IC), (ID), and (II). In some embodiments, the reporter moiety of the secondary antibody includes chromogenic, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected through antibody-hapten binding interactions using additional detectably labeled antibody conjugates, and paramagnetic and magnetic molecules or materials. Of course, the reporter moieties can themselves also be detected indirectly, e.g. if the reporter moiety is a hapten, then yet another antibody specific to that reporter moiety may be utilized in the detection of the reporter moiety, as known to those of ordinary skill in the art.

In some embodiments, the anti-label antibody includes a reporter moiety selected from the group consisting of DAB; AEC; CN; BCIP/NBT; fast red; fast blue; fuchsin; NBT; ALK GOLD; Cascade Blue acetyl azide; Dapoxylsulfonic acid/carboxylic acid succinimidyl ester; DY-405; Alexa Fluor 405 succinimidyl ester; Cascade Yellow succinimidyl ester; pyridyloxazole succinimidyl ester (PyMPO); Pacific Blue succinimidyl ester; DY-415; 7-hydroxycoumarin-3-carboxylic acid succinimidyl ester; DYQ-425; 6-FAM phosphoramidite; Lucifer Yellow; iodoacetamide; Alexa Fluor 430 succinimidyl ester; Dabcyl succinimidyl ester; NBD chloride/fluoride; QSY 35 succinimidyl ester; DY-485XL; Cy2 succinimidyl ester; DY-490; Oregon Green 488 carboxylic acid succinimidyl ester; Alexa Fluor 488 succinimidyl ester; BODIPY 493/503 C3 succinimidyl ester; DY-480XL; BODIPY FL C3 succinimidyl ester; BODIPY FL C5 succinimidyl ester; BODIPY FL-X succinimidyl ester; DYQ-505; Oregon Green 514 carboxylic acid succinimidyl ester; DY-510XL; DY-481XL; 6-carboxy-4',5'-dichloro-2',7'-dimethoxyfluorescein succinimidyl ester (JOE); DY-520XL; DY-521XL; BODIPY R6G C3 succinimidyl ester; erythrosin isothiocyanate; 5-carboxy-2',4',5',7'-tetrabromosulfonefluorescein succinimidyl ester; Alexa Fluor 532 succinimidyl ester; 6-carboxy-2',4,4',5'7,7'-hexachlorofluorescein succinimidyl ester (HEX); BODIPY 530/550 C3 succinimidyl ester; DY-530; BODIPY TMR-X succinimidyl ester; DY-555; DYQ-1; DY-556; Cy3 succinimidyl ester; DY-547; DY-549; DY-550; Alexa Fluor 555 succinimidyl ester; Alexa Fluor 546 succinimidyl ester; DY-548; BODIPY 558/568 C3 succinimidyl ester; Rhodamine red-X succinimidyl ester; QSY 7 succinimidyl ester; BODIPY 564/570 C3 succinimidyl ester; BODIPY 576/589 C3 succinimidyl ester; carboxy-X-rhodamine (ROX); succinimidyl ester; Alexa Fluor 568 succinimidyl ester; DY-590; BODIPY 581/591 C3 succinimidyl ester; DY-591; BODIPY TR-X succinimidyl ester; Alexa Fluor 594 succinimidyl ester; DY-594; carboxynaphthofluorescein succinimidyl ester; DY-605; DY-610; Alexa Fluor 610 succinimidyl ester; DY-615; BODIPY 630/650-X succinimidyl ester; erioglaucine; Alexa Fluor 633 succinimidyl ester; Alexa Fluor 635 succinimidyl ester; DY-634; DY-630; DY-631; DY-632; DY-633; DYQ-2; DY-636; BODIPY 650/665-X succinimidyl ester; DY-635; Cy5 succinimidyl ester; Alexa Fluor 647 succinimidyl ester; DY-647; DY-648; DY-650; DY-654; DY-652; DY-649; DY-651; DYQ-660; DYQ-661; Alexa Fluor 660 succinimidyl ester; Cy5.5 succinimidyl ester; DY-677; DY-675; DY-676; DY-678; Alexa Fluor 680 succinimidyl ester; DY-679; DY-680; DY-682; DY-681; DYQ-3; DYQ-700; Alexa Fluor 700 succinimidyl ester; DY-703; DY-701; DY-704; DY-700; DY-730; DY-731; DY-732; DY-734; DY-750; Cy7 succinimidyl ester; DY-749; DYQ-4; and Cy7.5 succinimidyl ester.

Fluorophores belong to several common chemical classes including coumarins, fluoresceins (or fluorescein derivatives and analogs), rhodamines, resorufins, luminophores and cyanines. Additional examples of fluorescent molecules can be found in Molecular Probes Handbook—A Guide to Fluorescent Probes and Labeling Technologies, Molecular Probes, Eugene, Oreg., TheroFisher Scientific, 11th Edition. In other embodiments, the fluorophore is selected from xanthene derivatives, cyanine derivatives, squaraine derivatives, naphthalene derivatives, coumarin derivatives, oxadiazole derivatives, anthracene derivatives, pyrene derivatives, oxazine derivatives, acridine derivatives, arylmethine derivatives, and tetrapyrrole derivatives. In other embodiments, the fluorescent moiety is selected from a CF dye (available from Biotium), DRAQ and CyTRAK probes (available from BioStatus), BODIPY (available from Invitrogen), Alexa Fluor (available from Invitrogen), DyLight Fluor (e.g. DyLight 649) (available from Thermo Scientific, Pierce), Atto and Tracy (available from Sigma Aldrich), FluoProbes (available from Interchim), Abberior Dyes (available from Abberior), DY and MegaStokes Dyes (available from Dyomics), Sulfo Cy dyes (available from Cyandye), HiLyte Fluor (available from AnaSpec), Seta, SeTau and Square Dyes (available from SETA BioMedicals), Quasar and Cal Fluor dyes (available from Biosearch Technologies), SureLight Dyes (available from APC, RPEPerCP, Phycobilisomes)(Columbia Biosciences), and APC, APCXL, RPE, BPE (available from Phyco-Biotech, Greensea, Prozyme, Flogen).

In other embodiments, the anti-label antibody is conjugated to an enzyme. In some embodiments, suitable enzymes include, but are not limited to, horseradish peroxidase, alkaline phosphatase, acid phosphatase, glucose oxidase, β-galactosidase, β-glucuronidase or β-lactamase. In other embodiments, enzymes include oxidoreductases or peroxidases (e.g. HRP, AP). In these embodiments, the enzyme conjugated to the anti-label antibody catalyzes conversion of a chromogenic substrate to a reactive moiety which covalently binds to a sample proximal to or directly on the target. Particular non-limiting examples of chromogenic compounds/substrates include diaminobenzidine (DAB), 4-nitrophenylphospate (pNPP), fast red, bromochloroindolyl phosphate (BCIP), nitro blue tetrazolium (NBT), BCIP/NBT, fast red, AP Orange, AP blue, tetramethylbenzidine (TMB), 2,2'-azino-di-[3-ethylbenzothiazoline sulphonate] (ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue, tetrazolium violet, N,N'-biscarboxypentyl-5,5'-disulfonato-indo-dicarbocyanine (Cy5), 4-(dimethylamino) azobenzene-4'-sulfonamide (DABSYL), tetramethylrhodamine (DISCO Purple), and Rhodamine 110 (Rhodamine). DAB, which is oxidized in the presence of peroxidase and hydrogen peroxide, results in the deposition of a brown, alcohol-insoluble precipitate at the site of enzymatic activity.

In some embodiments, the chromogenic substrates are signaling conjugates which comprise a latent reactive moiety and a chromogenic moiety. In some embodiments, the latent reactive moiety of the signaling conjugate is configured to undergo catalytic activation to form a reactive species that can covalently bond with the sample or to other detection components. The catalytic activation is driven by one or more enzymes (e.g., oxidoreductase enzymes and peroxidase enzymes, like horseradish peroxidase) and results in the formation of a reactive species. These reactive species are capable of reacting with the chromogenic moiety proximal to their generation, i.e. near the enzyme. Specific examples of signaling conjugates are disclosed in US Patent Publication No. 2013/0260379, the disclosure of which is hereby incorporated by reference herein in its entirety.

In embodiments where the label is biotin, the PNA conjugate may be contacted with streptavidin coupled to an enzyme (e.g. alkaline phosphatase or horseradish peroxidase). Without wishing to be bound by any particular theory, it is believed that the streptavidin-AP or streptavidin-HRP conjugates bind specifically and irreversibly to the biotin-labeled PNA conjugates. The PNA-biotin-streptavidin conjugates may then be visualized using a chromogenic substrate for alkaline phosphatase or horseradish peroxidase (such as those noted above) to produce a detectable signal. Likewise, where the label is biotin, the PNA conjugate may alternatively be contacted with streptavidin coupled to a fluorophore (e.g. FTIC) and the signals for the fluorophore detected.

In embodiments where the PNA tag may be cleaved from the antibody conjugates (via a cleavable linker as noted herein) and then detected according to the methods described in "Peptide nucleic acid characterization by MALDI-TOF mass spectrometry," Anal Chem. 1996 Sep. 15; 68(18):3283-7, the disclosure of which are incorporated by reference herein in their entirety. Likewise, the PNA sequence of the PNA conjugate may similarly be detected by other mass spectrometry such as electrospray ionization (ESI) according methods known to those of ordinary skill in the art.

Detection of Conjugates Using Complementary Nucleotide Sequences, Including Complementary PNA or DNA Sequences In some embodiments, conjugates of Formulas (I), (IA), (IC), (ID), and (II) may be detected by hybridizing one of a PNA sequence or a DNA sequence to the nucleotide sequence of the conjugate, the PNA sequence or DNA sequence being complementary to the nucleotide sequence of the conjugate.

In some embodiments, the conjugate of Formulas (I), (IA), (IC), (ID), and (II) does not comprise a label. In some embodiments, PNA or DNA sequences complementary to the nucleotide sequence of the conjugate comprises a reporter moiety, such as those described herein. In some embodiments, the reporter moiety is a chromogen. In other embodiments, the reporter moiety is a fluorophore. In yet other embodiments, the reporter moiety is a hapten (e.g. digoxigenin). In further embodiments, the reporter moiety is an enzyme. In even further embodiments, the reporter moiety is a nanoparticle (e.g. a gold nanoparticle, which may be used in scanning electronic imaging or a quantum dot).

Of course, the skilled artisan will appreciate that the same conjugate of Formulas (I), (IA), (IC), (ID), and (II) may be used to provide multiple imaging modalities. For example, if a fluorescently labeled complimentary DNA or PNA sequence is provided, it can be used for fluorescence imaging. With the same conjugate of Formulas (I), (IA), (IC), (ID), and (II), a haptenated DNA or PNA sequence can also be used for effect chromogenic imaging.

Detection and/or Quantification of Conjugates Using a NanoString nCounter Platform In some embodiments, the conjugates of Formulas (I), (IA), (IC), (ID), and (II) comprise an oligomer having a nucleotide sequence that may serve as a molecular "bar code." For example, while two PNA conjugates may comprise similar PNA oligomer portions, the PNA oligomer portions differing in certain bases within the PNA sequence. In this manner, PNA conjugates having different PNA sequences may be detected and/or quantified, such as by using the Nanostring nCounter Platform. In some embodiments, the PNA conjugates comprise a reporter moiety, such as a biotin label.

In some embodiments, the conjugates of any of Formulas (I), (IA), (IC), (ID), and (II) comprise a cleavable linker. Following the introduction of the conjugate of any of Formulas (I), (IA), (IC), (ID), and (II) to the sample, chemical reagents, enzymes, and/or radiation are introduced to the sample to cleave a group of the cleavable linker, thus releasing the nucleotide sequence (e.g. a PNA-antibody sequence) of the conjugate. This may, of course, be repeated for different conjugates of any of Formulas (I), (IA), (IC), (ID), and (II). Once all of the nucleotide sequences (e.g. PNA sequences) have been released, they may be detected and quantified as noted herein. The skilled artisan will also appreciate that different conjugates may comprise different cleavable linkers, and thus the different nucleotide sequences may be released at different times following introduction of different reagents/radiation, thus allowing step-wise detection and/or quantification. In some embodiments, the conjugates of any of Formulas (I), (IA), (IC), (ID), and (II) are PNA conjugates, i.e. the conjugates comprise an oligomer including a PNA sequence.

By way of example, where PD-L1 and Ki67 markers both exist on the same tissue section, an anti-PD-L1/PNA1 conjugate and anti-Ki67 PNA 2 conjugate may be used to stain the tissue section. PNA1 and PNA2 oligomer portions may comprise two different PNA have two different PNA sequences, yet both are chemically cleavable. After incubating the tissue with the two conjugated antibodies and careful rinsing to remove unbound PNA-conjugated antibodies, the two PNAs are cleaved. The two PNAs can be counted on nCounter (NanoString Technology) and the number of cleaved PNAs determined. The difference between the number of PNA1 and PNA 2 reflect the difference in the level of protein expression of the PD-L1 and Ki67 markers.

In these embodiments, the PNA sequences of the PNA conjugates may be detected and/or quantified in a similar manner to DNA since the detection scheme is based the hybridization of a reporter strand to the target oligomer (can be DNA or PNA). The PNA conjugates, however, are shorter than the standard DNA targets typically detected by the NanoString nCounter platform (which are about 70-100 bases in length). However, the presence of the biotin on the 3'end of the PNA excludes the need to use a capture strand. Moreover, the higher binding affinity of PNA to DNA compared to DNA to DNA provides enough stability to the relatively short PNA/DNA reporter duplex. The PNA sequence will be mixed with the reporter strand that is designed to be the complement to the PNA sequence. After removing unbound PNA the PNA/reporter constructs are incubated on the streptavidin-coated cartridge then aligned using electric field. The nCounter will be used to read and count the reporter strand. The same procedure can be done with multiple PNA sequences.

Detection and/or Quantification of Conjugates Using Gyros

Gyros is an immunoassay platform using an affinity flow-through format with parallel processing and laser-induced fluorescence detection. The assay is performed in a compact disk (CD) containing over 100 nanoliter-scale channels which uses centrifugal force and capillary action for liquid delivery and movement.

Figure 29:
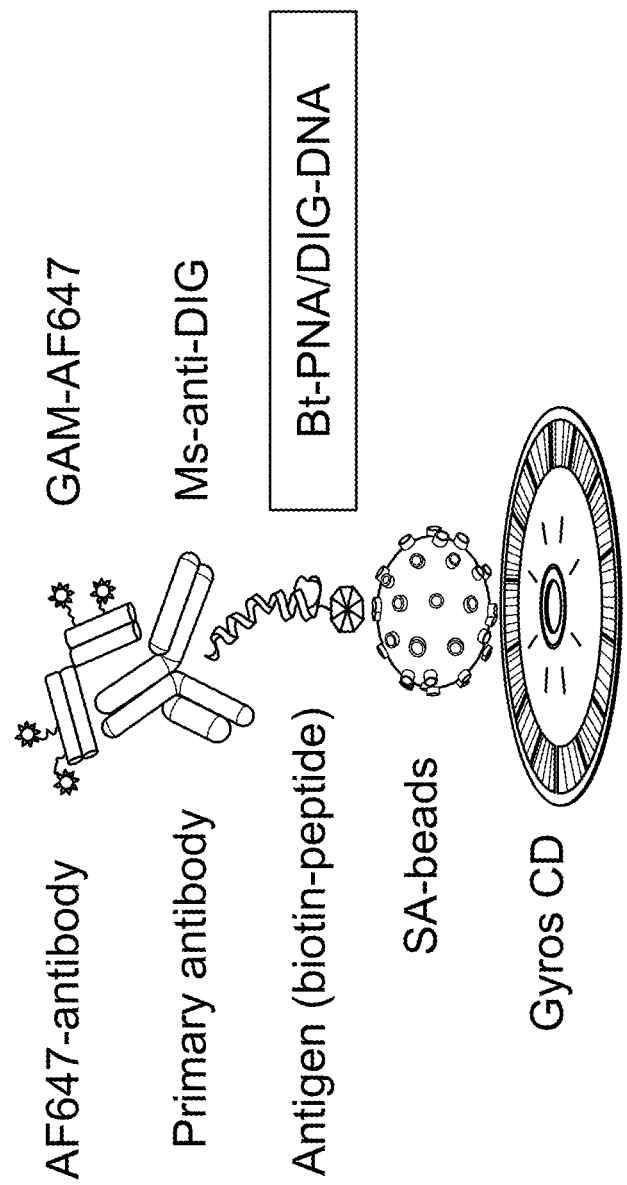
FIG. 29 illustrates the principle of using use of Gryos technology for the quantification of PNA.

In a typical non-limiting experiment, a biotinylated epitope peptide is first bound to a 15 nL affinity capture column consisting of streptavidin-coated beads. After rinsing, a primary antibody specific to the epitope peptide flows through the column and binds to the peptide. A fluorescent dye (e.g. Alexa Fluor 647) labeled secondary antibody then binds to the primary antibody which is then detected and quantified using laser-induced fluorescence. For the detection of the oligomers of the present disclosure, the biotinylated PNA oligomer is hybridized to a complementary single stranded DNA, which is conjugated to a reporter moiety (e.g. a hapten, including but not limited to digoxigenin). The biotin in the hybridized nucleic acid strands binds to the streptavidin-coated beads in the Gyros CD. The DIG label on the other end of the hybrid is then detected by Ms-anti-DIG antibody followed by Alexa Fluor 647 labeled goat-anti-mouse antibody (GAM), which facilitates quantitative measurement of the original oligomer. The principle of using Gyros technology for quantification is illustrated in FIG. 29. Additional information regarding Gyros Technology devices and their methods of use are described in U.S. Pat. Nos. 8,133,438 and 8,592,219, the disclosures of which are incorporated by reference herein in their entireties. Additional information pertaining to Gyros Technology devices and their methods of use are also described in US Patent Application Publication Nos. 2011/0116972, 2011/0195524, and 2007/0241061, the disclosures of which are hereby incorporated by reference herein in their entireties.

Any conjugate of Formulas (I), (IA), (IC), (ID), and (II) may be used for quantification using the Gyros platform, provided that the conjugate includes a linker capable of being cleaved (e.g. a linker including a disulfide group). Following the introduction of the conjugate of any of Formulas (I), (IA), (IC), (ID), and (II) to the sample, chemical reagents, enzymes, and/or radiation are introduced to the sample to cleave a group of the cleavable linker, thus releasing the nucleotide sequence (e.g. a PNA sequence) of the conjugate. Quantification may then proceed as noted above.

In some embodiments, the conjugates of any of Formulas (I), (IA), (IC), (ID), and (II) are PNA conjugates, i.e. the conjugates comprise an oligomer including a PNA sequence, the PNA conjugate comprising a primary antibody conjugated to a PNA oligomer as described herein. In some embodiments, the introduced single stranded DNA is complementary to and capable of hybridizing with the PNA sequence of the PNA conjugate. In some embodiments, the complementary single stranded DNA sequence is conjugated to a reporter moiety. In some embodiments, the complementary single stranded DNA sequence is conjugated to a hapten. In some embodiments, the complementary single stranded DNA sequence is conjugated to digoxigenin.

In some embodiments, multiple, different PNA conjugates may be introduced simultaneously or sequentially. The skilled artisan will also appreciate that the different PNA conjugates may comprise different cleavable linkers, and thus the different PNA sequences may be released at different times following introduction of different reagents/radiation, thus allowing step-wise quantification.

Figure 30:
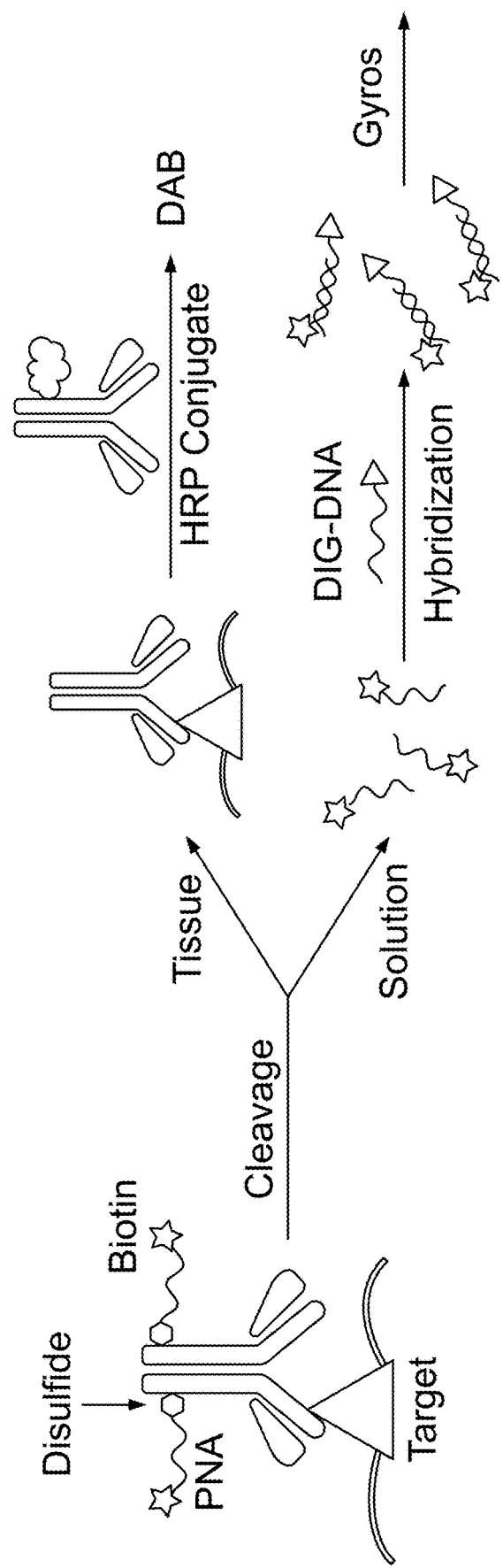
FIG. 30 provides a schematic illustrating the steps of quantification of cleaved PNA tag using Gryos technology and re-staining the slide by IHC to allow visualization of the same marker encoded by the PNA tag.

In some embodiments, following quantification with the Gyros platform, the tissue is stained according to methods commonly used in the art. For example, following cleavage of a PNA sequence from the PNA conjugate, the tissue in which the PNA conjugate was bound to may be stained by introducing an anti-primary antibody including a reporter moiety, such as illustrated in FIG. 30. In this way, quantification can be combined with visualization of a target in a biological sample.

Detection Kits Comprising PNA Conjugates and Detection Reagents for Detecting PNA Conjugates In some embodiments, the conjugates of Formulas (I), (IA), (IC), (ID), and (II) may be utilized as part of a "detection kit." In general, any detection kit may include one or more conjugates of Formulas (I), (IA), (IC), (ID), and (II) and detection reagents for detecting the one or more conjugates. In some embodiments, the kit includes one conjugate of any of Formulas (I), (IA), (IC), (ID), and (II) and an additional component (e.g. another antibody conjugate, a detection reagent, a wash reagent, a buffer, a counterstain, etc.). In other embodiments, the kit includes at least two conjugates of any of Formulas (I), (IA), (IC), (ID), and (II) and an optional additional component (e.g. another antibody conjugate, a detection reagent, a wash reagent, a buffer, a counterstain, etc.).

In some embodiments, the detection kits may include a first composition comprising a conjugate of any of Formulas (I), (IA), (IC), (ID), and (II), and a second composition comprising detection reagents specific to the first composition, such that the conjugate may be detected via the detection kit. In some embodiments, the detection kit includes a plurality of conjugates of Formulas (I), (IA), (IC), (ID), and (II) (such as those mixed together in a buffer, or those that are provided in individual shipping containers or compartments), where the detection kit also includes detection reagents specific for each of the plurality of conjugates.

By way of example, a kit may include a first PNA conjugate specific for a first target, the PNA conjugate having a first PNA oligomer portion, and a second PNA conjugate specific for a second target having a second PNA oligomer portion, wherein at least a portion of the first and second PNA oligomers are different. The kit may further comprise detection reagents specific for each of the different PNA conjugates.

By way of another example, a kit may include a first PNA conjugate having a first PNA oligomer portion (and one that does not comprise a label) and the kit may further include a PNA or DNA sequence that is complementary to the PNA sequence of the first PNA oligomer portion.

By way of yet another example, a kit may include a series of different PNA conjugates, each PNA conjugate specific to a different target and having a different PNA oligomer portion. Each different PNA conjugate of the kit may serve as a different molecular "bar code," which could be used in a qualitative and/or a quantitative analysis.

Of course, any kit may include other agents, including buffers; counterstaining agents; enzyme inactivation compositions; counterstains; deparraffinization solutions; etc. as needed for manual or automated target detection. The detection kits may also comprise other specific binding entities (e.g. nucleic acid probes for ISH; unmodified (native) antibodies, and antibody conjugates) and detection reagents to detect those other specific binding entities. For example, a kit may comprise one or more PNA conjugates; one or more anti-label antibodies for detecting the one or more PNA conjugates; at least one unmodified antibody (i.e. native antibody not coupled to a PNA sequence); and detection reagents for detecting the at least one unmodified antibody. In some embodiments, instructions are provided for using the PNA conjugates, and other components of the kit, for use in an assay, e.g. a MIHC assay.

Methods of Detecting Targets with the Conjugates of any of Formulas (I), (IA), (IC), (ID), and (II) and Detection Reagents The present disclosure also provides methods of detecting one or more targets within a tissue sample using any of the conjugates of Formulas (I), (IA), (IC), (ID), and (II) described herein. In some embodiments, a conjugate of any of Formulas (I), (IA), (IC), (ID), and (II) may be used in a simplex assay to directly or indirectly detect a particular target within the tissue sample (e.g. CD68, Ki67, CD20, etc.).

In some embodiments, the conjugates of any of Formulas (I), (IA), (IC), (ID), and (II) comprise a primary antibody (e.g. an antibody specific to CD68, Ki67, CD20, etc.). In these embodiments, the conjugates comprising a primary antibody may be used to directly "label" a target with a conjugate. In other embodiments, the conjugates of any of Formulas (I), (IA), (IC), (ID), and (II) comprise a secondary antibody. In these embodiments, and as discussed in more detail herein, a target (e.g. a protein target or a nucleic acid target) may be labeled with a primary antibody (for IHC) or a nucleic acid conjugate (e.g. a nucleic acid sequence coupled to a hapten, for ISH), and then the primary antibody or the nucleic acid conjugate may subsequently be "labeled" with a conjugate comprising a secondary antibody. These and other embodiments are described further herein.

In some embodiments, the PNA conjugates comprise a primary antibody where the PNA-primary antibody conjugate is specific to a target of interest, and where upon application of the PNA-primary antibody conjugate to the tissue sample, a target-PNA-primary antibody conjugate complex is formed (see, for example, FIGS. 22A-22D, and FIG. 26). Following application of the PNA-primary antibody conjugate, detection reagents (e.g. an anti-label antibody) may subsequently be applied such that the target-PNA-primary antibody conjugate complex may be detected. In some embodiments, the detection reagents comprise an anti-label antibody specific to the particular label of the PNA-primary antibody conjugate, where the anti-label antibody comprises a reporter moiety. The single target may then be visualized or otherwise detected.

In other embodiments, a tissue sample is first contacted with a primary antibody or a nucleic acid probe, forming either a target-primary antibody complex or a target-nucleic acid probe complex. Subsequently, a PNA conjugate comprising a secondary antibody is introduced to the tissue sample, the secondary antibody portion of the PNA conjugate being specific to either the (i) primary antibody, (ii) a label conjugated to the primary antibody, or (iii) a label conjugated to the nucleic acid probe. Application of the PNA-secondary antibody conjugate allows formation of a secondary complex, allowing the target to be "labeled." Following application of the PNA-secondary antibody conjugate and formation of the secondary complex, detection reagents (e.g. an anti-label antibody) may be applied such that the secondary complex may be detected. In some embodiments, the detection reagents comprise an anti-label antibody specific to the particular label of the PNA-secondary antibody conjugate, where the anti-label antibody comprises a reporter moiety. The target may then be visualized or otherwise detected.

In yet other embodiments, a tissue sample is first contacted with a PNA-primary antibody conjugate; or first contacted with a primary antibody followed by the introduction of a PNA-secondary antibody conjugate. Following introduction of the respective PNA conjugate, the sample may be contacted with a DNA or PNA sequence that is complementary to the PNA sequence of the PNA conjugate, the complementary DNA or PNA sequence comprising one or more reporter moieties (e.g. a chromogen, a fluorophore, an enzyme, or a hapten). In embodiments where the complimentary DNA or PNA sequence comprises a chromogen or a fluorophore, the "labeled" target complex may be directly detected. On the other hand, where the complementary DNA or PNA sequence comprises a hapten, an anti-hapten antibody conjugated to a reporter moiety must be introduced to facilitate eventual detection of the "labeled" target complex.

Of course, and as an alternative embodiment, DNA or PNA sequences of the conjugates of any of Formulas (I), (IA), (IC), (ID), and (II) may be quantified such as with the NanoString nCounter method or Gyros technology described herein, following cleavage of the DNA or PNA sequence from the conjugate. In some embodiments, the conjugates comprise a cleavable group and a biotin label. These methods would not require the use of any further detection reagents.

Figure 14A:
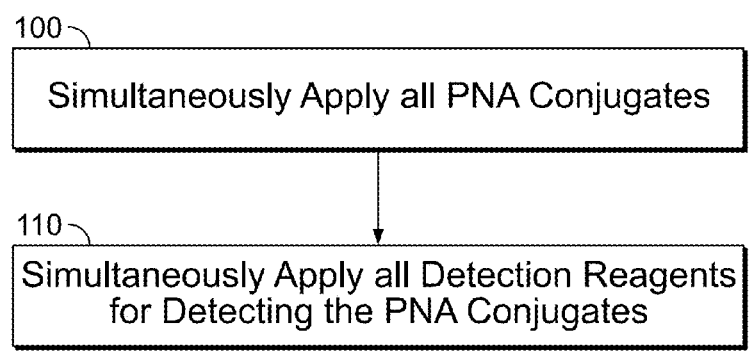
FIGS. 14A, 14B, and 14C set forth flowcharts outlining various methods of detecting targets in a sample using the PNA conjugates of the present disclosure.

In some aspects of the present disclosure are provided methods of multiplex detection, including automated multiplex detection. FIG. 14A provides a flowchart illustrating one method for the multiplex detection of targets where a tissue sample is contacted simultaneously with a plurality of PNA conjugates (step 100), where each PNA conjugate is specific for a particular target, and where each PNA conjugate comprises a different PNA oligomer (i.e. a PNA oligomer having a different PNA sequence and/or a different label). While FIG. 14A depicts the application of PNA conjugates, the skilled artisan will understand that PNA conjugates may comprise PNA-nucleic acid conjugates, PNA-primary antibody conjugates, and PNA-secondary antibody conjugates, depending on the target within the sample (e.g. a nucleic acid sequence, a protein target recognized by a primary antibody PNA conjugate, or a pre-deposited primary antibody recognized by a secondary antibody PNA conjugate). Of course, any of the PNA conjugates may have a PNA sequence having any number of nucleotides as described herein. The skilled artisan will further appreciate that the conjugates or PNA conjugates (or any other fluids or reagents) may be applied manually or with a specimen processing apparatus as described herein.

In some embodiments, the sample may be contacted with two PNA conjugates, where each PNA conjugate is specific for a particular target, and where each PNA conjugate comprises a different PNA oligomer portion. In other embodiments, the sample may be contacted with three PNA conjugates, where each PNA conjugate is specific for a particular target, and where each PNA conjugate comprises a different PNA oligomer portion.

The PNA conjugates may be supplied to the tissue sample as a "pool" or "cocktail" comprising each of the PNA conjugates needed for the particular assay. The pooling of PNA conjugates is believed to be possible since the PNA conjugates are believed not to be cross-reactive to each other, at least not to the extent where any cross-reactivity would interfere with staining performance. Each PNA conjugate will bind to their respective targets and form detectable target-PNA conjugate complexes. In some embodiments, and following application of the PNA conjugates, a blocking step is performed.

Following the simultaneous application of the PNA conjugates (step 100), a plurality of detection reagents is simultaneously applied to the tissue sample (step 110), where each detection reagent facilitates detection of one of the PNA conjugates initially applied (at step 100), and where each detection reagent comprises a different reporter moiety. In some embodiments, the detection reagents are streptavidin conjugated to a fluorophore, a chromophore, or a hapten. In other embodiments, the detection reagents are secondary antibodies specific for a label of the PNA conjugate (e.g. anti-hapten antibodies specific to a hapten of the PNA conjugate). In yet other embodiments, the detection reagents are DNA or PNA sequences that are complementary to a PNA sequence of the PNA oligomer portion of the PNA conjugate. In embodiments where anti-label antibodies are employed, the anti-label antibodies may be supplied to the tissue sample as a pool or cocktail comprising each of the anti-label antibodies necessary for detection of the target-PNA conjugate complexes. Following application of the detection reagents, in some embodiments the tissue sample may be stained with a counterstain. Signals from each of the labels and/or reporter moieties may be visualized or otherwise detected (e.g. simultaneously visualized or detected).

One example of a multiplex assay utilizing PNA conjugates is as follows. A first PNA-antibody conjugate comprising a first PNA oligomer and specific to a first target (e.g. specific to one of CD68, Ki67, CD20, etc.) is introduced to a tissue sample. In some embodiments, the first PNA-antibody conjugate forms a detectable first target-PNA-antibody conjugate complex. Simultaneously, a second PNA-antibody conjugate comprising a second PNA oligomer and specific to a second target (e.g. another of CD68, Ki67, CD20, etc.) is introduced to the sample to form a second target-PNA-antibody conjugate complex. Third, fourth, and nth additional PNA-antibody conjugates to other targets (forming "n" target-detection probe complexes) and having different PNA sequences and/or labels may be further introduced simultaneously with the first and second PNA-antibody conjugates.

After the PNA-antibody conjugates are deposited, they may be detected, either directly or indirectly depending, of course, on their configuration. In some embodiments, anti-label antibodies are introduced to enable detection of each of the target-PNA-antibody conjugate complex. In some embodiments, the anti-label antibodies are specific to the different labels of the PNA conjugates, and where the anti-label antibodies are each conjugated to a different reporter moiety. In some embodiments, the detectable reagents are anti-label antibodies each conjugated to a fluorophore. In some embodiments, first, second, and nth anti-label antibodies are simultaneously introduced, where each of the first, second, and nth detection reagents are specific to the different PNA-antibody conjugates, where each of the anti-label antibodies are conjugated to a fluorophore. In other embodiments, first, second, and nth anti-label antibodies are sequentially introduced, where each of the first, second, and nth detection reagents are specific to the different PNA-antibody conjugates, and wherein each of the anti-label antibodies are conjugated to an enzyme.

Alternatively, the PNA-antibody conjugates may be detected by introducing PNA or DNA sequences that are complementary to PNA sequences of the PNA oligomer portions of the introduced PNA conjugates. Each complementary PNA or DNA sequence may comprise a reporter moiety as detailed herein, including an enzyme, a fluorophore, a hapten, or a nanoparticle. If the complementary PNA or DNA sequence comprises a hapten, additional detection reagents (e.g. anti-hapten antibodies conjugated to an enzyme or fluorophore) may be introduced to facilitate detection of the complementary PNA or DNA sequences, and hence the targets within the sample.

As a further example of a multiplex assay according to the present disclosure, a first PNA-antibody conjugate specific to a first target (e.g. CD3, Ki67, PD-L1, or an immune cell marker) is introduced to a tissue sample, the first PNA-antibody conjugate having a first label. In some embodiments, the first PNA-antibody conjugate forms a detectable first target-PNA-antibody conjugate complex. Either simultaneously or subsequently, a second PNA-antibody conjugate specific to a second target (e.g. another of CD3, Ki67, PD-L1) is introduced to the sample to form a second target-PNA-antibody conjugate complex, the second PNA-antibody conjugate having a second label. Third, fourth, and nth additional PNA-antibody conjugates each specific to other targets (forming "n" target-PNA-antibody conjugate complexes) may be further introduced, again either sequentially or simultaneously with the first and/or second PNA-antibody conjugates, where the third, fourth and nth PNA-antibody conjugates each have yet different labels. After the PNA-antibody conjugates are deposited, they may be detected. In some embodiments, additional detection reagents are introduced to enable the detection of the targets and the additional detection reagents include those described herein (e.g. chromogenic detection reagents). In some embodiments, first, second, and nth detection reagents are sequentially introduced, where each of the first, second, and nth detection reagents comprise (i) a secondary antibody, namely an anti-label antibody, specific to each of the labels of the PNA-antibody conjugates, wherein the secondary antibody is conjugated to an enzyme; and (ii) a chromogenic substrate; wherein each of the first, second, and nth chromogenic substrates are different. In other embodiments, first, second, and nth detection reagents are sequentially introduced, where each of the first, second, and nth detection reagents comprise PNA or DNA sequences complementary to PNA sequences of the PNA oligomer portions of each of the PNA conjugates, each complementary PNA or DNA sequence comprising a reporter moiety.

As yet a further example of a multiplex assay according to the present disclosure, a first primary antibody specific to a first target (e.g. CD3, Ki67, PD-L1, or an immune cell marker) is introduced to a tissue sample (where the first primary antibody is not a conjugate of any of Formulas (I), (IA), (IC), (ID), and (II)). Subsequently, a first secondary antibody-PNA conjugate specific to the first primary antibody or a label conjugated to the first primary antibody is introduced, the first secondary-antibody PNA conjugate comprising a first PNA oligomer having a first PNA sequence. In some embodiments, the first secondary antibody-PNA-antibody conjugate forms a detectable first target-secondary antibody-PNA-antibody conjugate complex. Subsequently, the first PNA sequence of the secondary-antibody PNA conjugate is cleaved from the conjugate.

Subsequently, a second primary antibody specific to a second target (e.g. another of CD3, Ki67, PD-L1) is introduced to the sample. Subsequently, a second secondary antibody-PNA conjugate specific to the second primary antibody or a label conjugated to the second primary antibody is introduced, the second secondary-antibody PNA conjugate comprising a second PNA oligomer having a second PNA sequence. In some embodiments, the second secondary antibody-PNA-antibody conjugate forms a detectable second target-secondary antibody-PNA-antibody conjugate complex. Subsequently, the second PNA sequence of the secondary-antibody PNA conjugate is cleaved from the conjugate. The skilled artisan will appreciate that any number of primary antibodies and secondary antibody PNA-conjugates may be introduced sequentially, followed by cleavage of the PNA sequence from the PNA oligomer of the respective secondary antibody PNA-conjugate. Finally, all of the different PNA sequences may be measured, and the targets may be quantified.

In yet other embodiments, the multiplex detection method comprises the steps of (i) contacting a biological sample with a first PNA-antibody conjugate to form a first target antibody-PNA conjugate complex; (ii) contacting the biological sample with a first labeling conjugate wherein the first labeling conjugate comprises a first enzyme (where the first labeling conjugate is an anti-label antibody that specifically binds to the first PNA-antibody conjugate and is configured to label the target with an enzyme); (iii) contacting the biological sample with a first signaling conjugate comprising a first latent reactive moiety and a first chromogenic moiety (see, e.g. U.S. patent application Ser. No. 13/849,160, the disclosure of which is incorporated herein by reference for a description of signaling conjugates and their constituent components); (iv) inactivating the first enzyme, such as by contacting the sample with a first enzyme inactivation composition to substantially inactivate or completely inactivate the first enzyme contained in the biological sample.

After the first enzyme is inactivated (optional), the multiplex method further comprises the steps of (v) contacting a biological sample with a second PNA-antibody conjugate to form a second target-PNA-antibody conjugate complex; (vi) contacting the biological sample with a second labeling conjugate wherein the second labeling conjugate comprises a second enzyme (where the second labeling conjugate is an anti-label antibody that specifically binds to the second PNA-antibody conjugate and is configured to label the target with an enzyme); (vii) contacting the biological sample with a second signaling conjugate comprising a second latent reactive moiety and a second chromogenic moiety; (viii) inactivating the second enzyme, such as by contacting the sample with a first enzyme inactivation composition to substantially inactivate or completely inactivate the first enzyme contained in the biological sample.

After the second enzyme is inactivated, the method may be repeated such that additional PNA-antibody conjugates may be introduced, along with additional detection reagents, to effectuate detection of other targets. Following introduction of all of the PNA-antibody conjugates (and other detection probes) and respective detection reagents or kits, the method further comprises the step of counterstaining the sample and/or detecting signals (manually or via an automated method) from the first, second, and nth chromogenic moieties, wherein each of the first, second, and nth chromogenic moieties are each different. Alternatively, each of the PNA-antibody conjugates may be added simultaneously or sequentially, but before any labeling conjugate is added. As another example, three PNA-antibody conjugates may be sequentially applied initially, prior to introduction of any detection reagents, and then each of the detection reagents added sequentially.

In the context of a multiplex assay where multiple targets are detected sequentially, and where the detection employs the use of enzymes, it is desirable to inactivate any reagent or endogenous enzymes between successive detection steps. As a result, it is believed that enzymes present in any one detection step will not interfere with those in a later detection steps. This in turn is believed to improve upon the visualization and detection of the different detectable moieties used in the multiplex assay. Any enzyme inactivation composition known in the art may be used for this purpose. In some embodiments, an enzyme inactivation composition is applied to inactivate the reagent or endogenous enzymes after each detection step. Exemplary enzyme inactivation compositions are disclosed in application U.S. 62/159,297, the disclosure of which is incorporated by reference herein in its entirety.

In some embodiments, a denaturation step prevents the enzyme used in a first set of detection reagents from acting on a second substrate. In some embodiments, the denaturant is a substance that denatures the enzyme in the first detection reagent set. In some embodiments, the denaturant is, for example, formamide, an alkyl-substituted amide, urea or a urea-based denaturant, thiourea, guanidine hydrochloride, or derivatives thereof. Examples of alkyl-substituted amides include, but are not limited to, N-propylformamide, N-butylformamide, N-isobutylformamide, and N,N-dipropylaformamide. In some embodiments, the denaturant is provided in a buffer. For example, formamide may be provided in a hybridization buffer comprising 20 mM dextran sulfate (50-57% % formamide (UltraPure formamide stock), 2×SSC (20×SSC stock containing 0.3 M citrate and 3M NaCl), 2.5 mM EDTA (0.5M EDTA stock), 5 mM Tris, pH 7.4 (1 mM Tris, pH 7.4 stock), 0.05% Brij-35 (10% stock containing polyoxyethylene (23) lauryl ether), pH 7.4. In some embodiments, the sample is treated with the denaturant for a period of time and under conditions sufficient to denature the first target probe detection enzyme, for example alkaline phosphatase. In some embodiments, the sample is treated with the denaturant for about 15 to about 30 minutes, preferably about 20 to 24 minutes at about 37° C. In some embodiments, the sample is treated with the denaturant for a period of time and under conditions sufficient to denature the target enzyme while preserving hybridization of the second nucleic acid probe to the target.

For those embodiments employing an anti-label antibody conjugated to an enzyme, conditions suitable for introducing the signaling conjugates or chromogenic substrates with the biological sample are used, and typically include providing a reaction buffer or solution that comprises a peroxide (e.g., hydrogen peroxide), and that has a salt concentration and pH suitable for allowing or facilitating the enzyme to perform its desired function. In general, this step of the method is performed at temperatures ranging from about 35° C. to about 40° C., although the skilled artisan will be able to select appropriate temperature ranges appropriate for the enzymes and signalizing conjugates selected. For example, it is believed that these conditions allow the enzyme and peroxide to react and promote radical formation on the latent reactive moiety of the signaling conjugate. The latent reactive moiety, and therefore the signaling conjugate as a whole, will deposit covalently on the biological sample, particularly at one or more tyrosine residues proximal to the immobilized enzyme conjugate, tyrosine residues of the enzyme portion of the enzyme conjugate, and/or tyrosine residues of the antibody portion of the enzyme conjugate. The biological sample is then illuminated with light and the target may be detected through absorbance of the light produced by the chromogenic moiety of the signaling conjugate.

Methods of Detection with the Conjugates of any of Formulas (I), (IA), (IC), (ID), and (II) in Conjunction with Other Specific Binding Entities In some aspects of the present disclosure, the conjugates of any of Formulas (I), (IA), (IC), (ID), and (II) are used in conjugation with other specific binding entities to effect multiplex detection of targets in a tissue sample. The skilled artisan will appreciate that any of the above-identified methods and procedures may be adapted accordingly for any assay employing both conjugates of any of Formulas (I), (IA), (IC), (ID), and (II) and other specific binding entities.

In some embodiments, the other specific binding entities include nucleic acids for in situ hybridization and unmodified antibodies for IHC. As used herein, the terms "unmodified antibody" or "unmodified antibodies" refer to those antibodies that do not comprise a nucleotide sequence (e.g. a DNA or PNA nucleotide sequence as identified herein), but includes those antibodies conjugated to a hapten or another label. In essence, "unmodified antibodies" are native antibodies traditionally used in IHC assays, which are specific to a particular target (e.g. an anti-CD3 antibody) and which may be detected, such as with anti-species secondary antibodies or, if they comprise a label, an anti-label antibody. By way of example, a rabbit anti-CD3 antibody may be detected with a goat anti-rabbit antibody. Likewise, a rabbit anti-CD3 antibody conjugated to a hapten may be detected with an anti-hapten antibody.

Figure 14B:
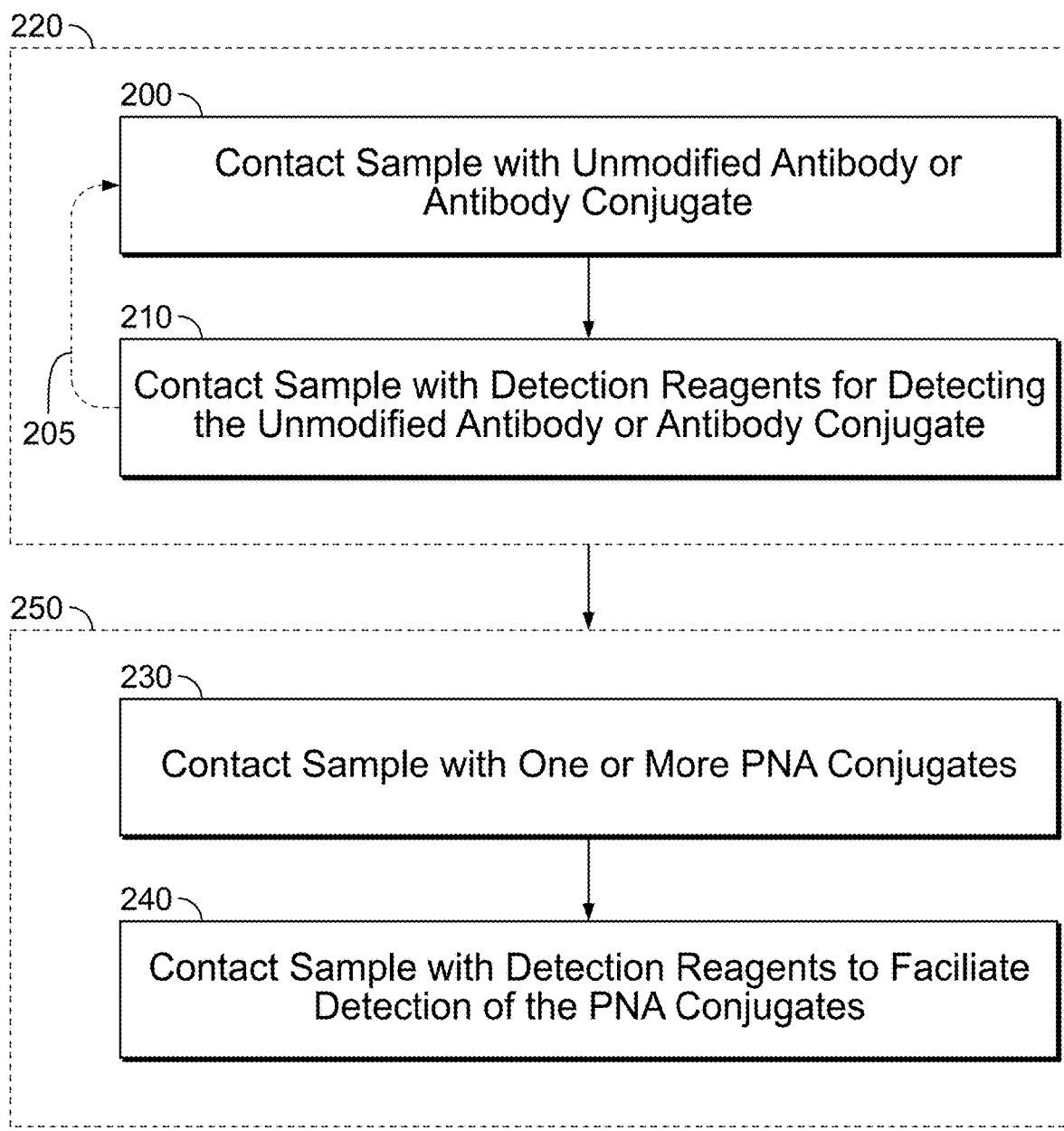
Figure 14C:
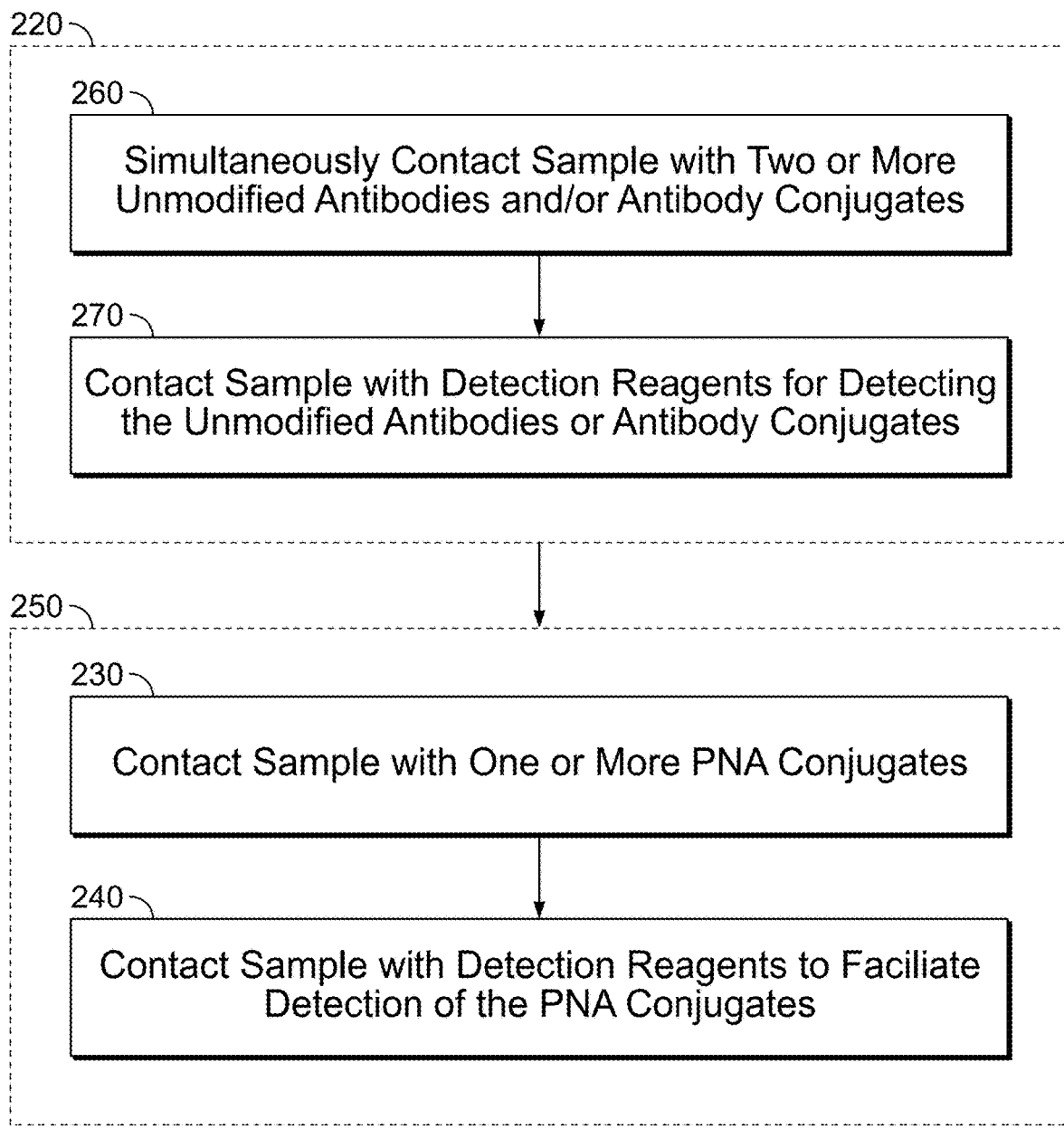
Figure 15A:
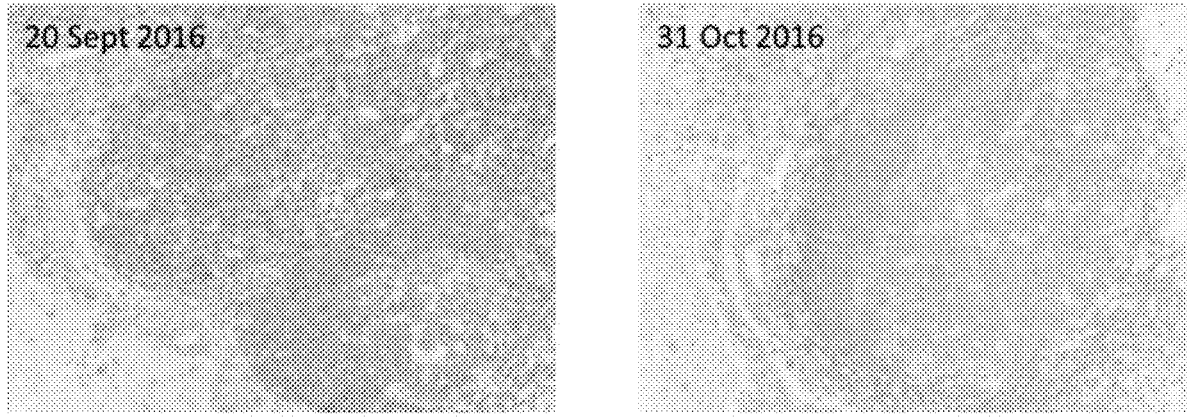
FIG. 15A illustrates the stability of the PNA antibody conjugates. Tonsil slides were incubated with primary antibodies (anti-CD45) followed by GAM-PNA and detected with SA-HRP and DAB deposition. The same antibody-PNA conjugates were used at later time as indicated to assess the conjugates stability.
Figure 15B:
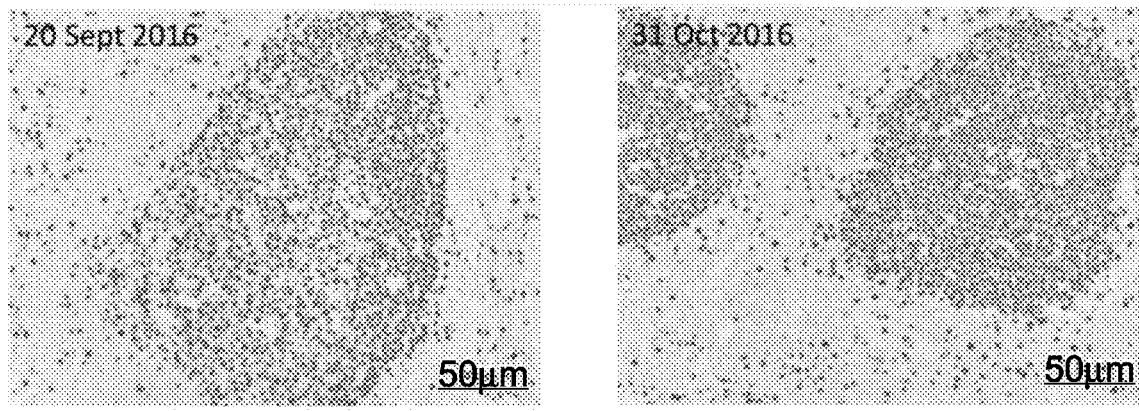
FIG. 15B illustrates the stability of the PNA antibody conjugates. Tonsil slides were incubated with primary antibodies (anti-Ki67) followed by GAR-PNA and detected with SA-HRP and DAB deposition. The same antibody-PNA conjugates were used at later time as indicated to assess the conjugates stability.

FIGS. 14B and 14C illustrate methods for the multiplex detection of targets where a tissue sample is contacted with one or more unmodified primary antibodies (simultaneously or sequentially) (first stage, 220) and then subsequently contacted with one or more PNA conjugates (simultaneously or sequentially) (second stage, 250). The skilled artisan will recognize that the first stage 220 and the second stage 250 may be reversed, such that the PNA conjugates are applied first to the tissue sample followed by application of the unmodified antibodies. The skilled artisan will also appreciate that appropriate nucleic acid probes (including those conjugated to a label) may be substituted for the unmodified antibodies such that the multiplex assay includes both ISH and IHC steps or stages (in any order). The skilled artisan will further appreciate that the conjugates or PNA conjugates (or any other fluids or reagents) may be applied manually or with a specimen processing apparatus as described herein.

In some embodiments, such as depicted in FIG. 14B, a first unmodified primary antibody may be applied to a tissue sample to form a first target-primary antibody complex (step 200). Next, first detection reagents specific to the unmodified primary antibody are applied to the tissue sample to detect the first target-primary antibody complex (step 210). Dotted line 205 in FIG. 14B illustrates that steps 200 and 210 of first stage 220 may be repeated one or more times to provide for the sequential multiplex detection of multiple, different targets within the tissue sample with unmodified primary antibodies. For example, a second unmodified primary antibody be applied to the tissue sample to form a second target-primary antibody complex (200), followed by application of second detection reagents specific to the second unmodified primary antibody detect the second target-primary antibody complex (210).

FIG. 14C represents an alternative method for the multiplex detection of targets using a two-stage method similar to that presented in FIG. 14B. In the method depicted in FIG. 14C, each of the unmodified antibody conjugates are simultaneously introduced to the tissue sample at step 260. Next, the sample is contacted with detection reagents (e.g. anti-species antibodies or anti-label antibodies) at step 270 to effectuate detection of the unmodified antibodies. In an alternative embodiment, all of the unmodified primary antibodies may be sequentially applied (step 260), followed by sequential application of the respective anti-species antibodies (step 270) (or, where appropriate, anti-hapten antibodies).

The skilled artisan will appreciate that the detection reagents for the unmodified antibodies may comprise anti-species antibodies specific to the utilized unmodified antibodies. Alternatively, the detection reagents for the unmodified antibodies may comprise anti-hapten antibodies specific to haptens conjugated to the unmodified antibodies. The skilled artisan will also appreciate that the anti-species or anti-hapten antibodies may comprise a reporter moiety and, in embodiments where the reporter moiety is an enzyme, additional chromogenic substrates may be supplied with the first and second detection reagents.

Following the first stage of the multiplex assay 220 (FIG. 14B or 14C), a second stage 250 is performed, where the tissue sample is simultaneously or sequentially contacted with a plurality of PNA conjugates (step 230), where each PNA conjugate is specific for a particular target, and where each PNA conjugate comprises a different PNA oligomer portion. The PNA conjugates may be supplied to the tissue sample as a "pool" or "cocktail" comprising each of the PNA conjugates needed for the particular assay. Each PNA conjugate will form a detectable target-PNA conjugate complex with a specific target. Following the simultaneous or sequential application of the PNA conjugates (step 230), anti-label antibodies (secondary antibodies) are simultaneously applied to the tissue sample (step 240), where each anti-label antibody is specific to one of PNA conjugates applied, and where each anti-label antibody comprises a different reporter moiety. The anti-label antibodies may be supplied to the tissue sample as a "pool" or "cocktail" comprising each of the anti-label antibodies necessary for detection of the target-PNA-antibody complexes.

Alternatively, following introduction of the respective PNA conjugates at step 230, the sample may be contacted at step 240 with a PNA sequence or a DNA sequence that is complementary to the PNA sequence of the PNA conjugate, the DNA sequence comprising a reporter moiety (e.g. an enzyme, chromogen, a fluorophore, or a hapten). In embodiments where the DNA sequence comprises a chromogen or a fluorophore, the "labeled" target complex may be directly detected. On the other hand, where the DNA sequence comprises a hapten, an anti-hapten antibody conjugated to a reporter moiety must be introduced to facilitate eventual detection of the "labeled" target complex.

Of course, and as an alternative embodiment, PNA sequences of the respective PNA conjugates may be quantified such as with the NanoString nCounter method described herein.

Following step 250, in some embodiments the tissue sample may be stained with a counterstain. Signals from each of the reporter moieties (e.g. from the anti-species or anti-label antibodies) may be visualized or otherwise detected (e.g. simultaneously visualized or detected).

As an example of a multiplex assay comprising both (i) unmodified antibodies, and (ii) PNA-antibody conjugates according to the present disclosure, a first antibody conjugate comprising a hapten label (e.g. an anti-CD3 antibody conjugated indirectly to a happen) is introduced to a tissue sample to form a target-antibody-conjugate complex. Simultaneously, an unmodified antibody (e.g. a rabbit anti-PDL1 antibody) is introduced to the tissue sample to form a target-unmodified-antibody complex. Next, detection reagents are introduced (simultaneously or sequentially) to detect the formed target-antibody-conjugate complex (e.g. an anti-happen antibody) and the formed target-unmodified-antibody complex (e.g. a goat anti-rabbit antibody), where each of the detection reagents are conjugated to a different fluorophore.

In a second stage of the multiplex assay, a first PNA-antibody conjugate comprising a first PNA oligomer and specific to a first target (e.g. specific to CD68) is introduced to a tissue sample. In some embodiments, the first PNA-antibody conjugate forms a detectable first target-PNA-antibody conjugate complex. Sequentially or simultaneously, a second PNA-antibody conjugate comprising a second PNA oligomer and specific to a second target (e.g. specific to Ki67) is introduced to the sample to form a second target-PNA-antibody conjugate complex. Third, fourth, and nth additional PNA-antibody conjugates specific to other targets (forming "n" target-PNA-antibody complexes) and having different PNA oligomers may be further introduced simultaneously with the first and second PNA-antibody conjugates. In alternative embodiments, PNA-antibody conjugates may be added sequentially, wherein the PNA sequence is cleaved from a PNA-antibody conjugate prior to introduction of a subsequent PNA-antibody conjugate. The cleaved PNA sequences may then be measured together.

After the PNA-antibody conjugates are deposited, they may be detected, either directly or indirectly depending, of course, on their configuration. In some embodiments, first, second, and nth detection reagents are simultaneously introduced, where each of the first, second, and nth detection reagents are specific to the different PNA-antibody conjugates. In other embodiments, first, second, and nth detection reagents are sequentially introduced, where each of the first, second, and nth detection reagents are specific to the different PNA-antibody conjugates. In some embodiments, anti-label antibodies are introduced to enable detection of each of the target-PNA-antibody conjugates complexes. In some embodiments, the detection reagents are anti-label antibodies that are specific to the different labels of the PNA-antibody conjugates and where the anti-label antibodies are each conjugated to a reporter moiety, e.g. a fluorophore or an enzyme. In some embodiments, the detectable reagents are anti-label antibodies each conjugated to a fluorophore. In other embodiments, the detectable reagents are anti-label antibodies each conjugated to an enzyme. In yet other embodiments, the detectable reagents are a combination of anti-label antibodies conjugated to a fluorophore and anti-label antibodies conjugated to an enzyme. In those embodiments where the anti-label antibodies are conjugated to an enzyme, substrates for the enzymes are provided to effect detection (as noted previously herein). In other embodiments, PNA or DNA sequences complementary to one or more of PNA sequences and comprising enzymes, fluorophores or haptens are introduced to enable detection of each of the target-PNA-antibody conjugates complexes. In yet other embodiments, the detection reagents are PNA or DNA sequences that are complementary to a PNA sequence of the PNA oligomer portion of the PNA conjugate. The skilled artisan will appreciate that where complementary PNA or DNA sequences are provided which are conjugated to a hapten, further reagents may be supplied to the sample to facilitate detection of the complementary PNA or DNA sequences. In alternative embodiments, the PNA-conjugated antibodies may be hybridized to a complementary PNA or DNA sequence ex situ and then the complex, i.e. PNA-conjugated antibody hybridized to the complementary PNA or DNA sequence) may be introduced to the tissue to enable labeling of targets within the sample.

Automation

The multiplex assays and methods may be automated and may be combined with a specimen processing apparatus. For example, a specimen processing apparatus or automated specimen processing apparatus may apply between about 100 microliters and about 500 microliters of a conjugate of the present disclosure to a sample disposed on a microscope slide. In some embodiments, a specimen processing apparatus is an automated apparatus, such as the BENCHMARK XT instrument, the BenchMark Special Stains instrument, the NexES Special Stainer instrument, the SYMPHONY instrument, or the BENCHMARK ULTRA instrument sold by Ventana Medical Systems, Inc. Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. Published Patent Application Nos. 2003/0211630 and 2004/0052685, each of which is incorporated herein by reference in its entirety. Alternatively, specimens can be manually processed. Examples of other commercially available specimen processing systems through which the acid fast staining composition may be applied include the VENTANA SYMPHONY (individual slide stainer) and the VENTANA HE 600 (individual slide stainer) series; the Dako CoverStainer (batch stainer) from Agilent Technologies; the Leica ST4020 Small Linear Stainer (batch stainer), Leica ST5020 Multistainer (batch stainer), and the Leica ST5010 Autostainer XL series (batch stainer) H&E stainers from Leica Biosystems Nussloch GmbH. In addition to applying any of the conjugates disclosed herein, the specimen processing apparatus may dispense other antibodies, antibody conjugates, counterstains, etc. to the specimen. Indeed, the specimen processing apparatus can apply a wide range of substances to the specimen. The substances include, without limitation, stains, probes, reagents, rinses, and/or conditioners. The substances can be fluids (e.g., gases, liquids, or gas/liquid mixtures), or the like. The fluids can be solvents (e.g., polar solvents, non-polar solvents, etc.), solutions (e.g., aqueous solutions or other types of solutions), or the like. Reagents can include, without limitation, stains, wetting agents, antibodies (e.g., monoclonal antibodies, polyclonal antibodies, etc.), antigen recovering fluids (e.g., aqueous- or non-aqueous-based antigen retrieval solutions, antigen recovering buffers, etc.), or the like. Probes can be an isolated nucleic acid or an isolated synthetic oligonucleotide, attached to a detectable label or reporter molecule. Labels can include radioactive isotopes, enzyme substrates, co-factors, ligands, chemiluminescent or fluorescent agents, haptens, and enzymes.

The specimen processing apparatus can apply fixatives to the specimen. Fixatives can include cross-linking agents (such as aldehydes, e.g., formaldehyde, paraformaldehyde, and glutaraldehyde, as well as non-aldehyde cross-linking agents), oxidizing agents (e.g., metallic ions and complexes, such as osmium tetroxide and chromic acid), protein-denaturing agents (e.g., acetic acid, methanol, and ethanol), fixatives of unknown mechanism (e.g., mercuric chloride, acetone, and picric acid), combination reagents (e.g., Carnoy's fixative, methacarn, Bouin's fluid, B5 fixative, Rossman's fluid, and Gendre's fluid), microwaves, and miscellaneous fixatives (e.g., excluded volume fixation and vapor fixation).

If the specimen is a sample embedded in paraffin, the sample can be deparaffinized with the specimen processing apparatus using appropriate deparaffinizing fluid(s). After the waste remover removes the deparaffinizing fluid(s), any number of substances can be successively applied to the specimen. The substances can be for pretreatment (e.g., protein-crosslinking, expose nucleic acids, etc.), denaturation, hybridization, washing (e.g., stringency wash), detection (e.g., link a visual or marker molecule to a probe), amplifying (e.g., amplifying proteins, genes, etc.), counterstaining, coverslipping, or the like.

After the specimens are processed, a user can transport specimen-bearing slides to the imaging apparatus. The imaging apparatus used here is a brightfield imager slide scanner. One brightfield imager is the iScan Coreo™ brightfield scanner sold by Ventana Medical Systems, Inc. In automated embodiments, the imaging apparatus is a digital pathology device as disclosed in International Patent Application No.: PCT/US2010/002772 (Patent Publication No.: WO/2011/049608) entitled IMAGING SYSTEM AND TECHNIQUES or disclosed in U.S. Patent Application Publication No. 2014/0178169, filed on Feb. 3, 2014, entitled IMAGING SYSTEMS, CASSETTES, AND METHODS OF USING THE SAME. International Patent Application No. PCT/US2010/002772 and U.S. Patent Application Publication No. 2014/0178169 are incorporated by reference in their entities. In other embodiments, the imaging apparatus includes a digital camera coupled to a microscope.

Counterstaining

Counterstaining is a method of post-treating the samples after they have already been stained with agents to detect one or more targets, such that their structures can be more readily visualized under a microscope. For example, a counterstain is optionally used prior to coverslipping to render the immunohistochemical stain more distinct. Counterstains differ in color from a primary stain. Numerous counterstains are well known, such as hematoxylin, eosin, methyl green, methylene blue, Giemsa, Alcian blue, and Nuclear Fast Red. DAPI (4',6-diamidino-2-phenylindole) is a fluorescent stain that may be used.

In some examples, more than one stain can be mixed together to produce the counterstain. This provides flexibility and the ability to choose stains. For example, a first stain, can be selected for the mixture that has a particular attribute, but yet does not have a different desired attribute. A second stain can be added to the mixture that displays the missing desired attribute. For example, toluidine blue, DAPI, and pontamine sky blue can be mixed together to form a counterstain. The counterstain may be applied by a specimen processing system as disclosed herein.

Imaging

Certain aspects, or all, of the disclosed embodiments can be automated, and facilitated by computer analysis and/or image analysis system. In some applications, precise color or fluorescence ratios are measured. In some embodiments, light microscopy is utilized for image analysis. Certain disclosed embodiments involve acquiring digital images. This can be done by coupling a digital camera to a microscope. Digital images obtained of stained samples are analyzed using image analysis software. Color or fluorescence can be measured in several different ways. For example, color can be measured as red, blue, and green values; hue, saturation, and intensity values; and/or by measuring a specific wavelength or range of wavelengths using a spectral imaging camera. The samples also can be evaluated qualitatively and semi-quantitatively. Qualitative assessment includes assessing the staining intensity, identifying the positively-staining cells and the intracellular compartments involved in staining, and evaluating the overall sample or slide quality. Separate evaluations are performed on the test samples and this analysis can include a comparison to known average values to determine if the samples represent an abnormal state.

Samples and Targets

Samples include biological components and generally are suspected of including one or more target molecules of interest. Target molecules can be on the surface of cells and the cells can be in a suspension, or in a tissue section. Target molecules can also be intracellular and detected upon cell lysis or penetration of the cell by a probe. One of ordinary skill in the art will appreciate that the method of detecting target molecules in a sample will vary depending upon the type of sample and probe being used. Methods of collecting and preparing samples are known in the art.

Samples for use in the embodiments of the method and with the composition disclosed herein, such as a tissue or other biological sample, can be prepared using any method known in the art by of one of ordinary skill. The samples can be obtained from a subject for routine screening or from a subject that is suspected of having a disorder, such as a genetic abnormality, infection, or a neoplasia. The described embodiments of the disclosed method can also be applied to samples that do not have genetic abnormalities, diseases, disorders, etc., referred to as "normal" samples. Such normal samples are useful, among other things, as controls for comparison to other samples. The samples can be analyzed for many different purposes. For example, the samples can be used in a scientific study or for the diagnosis of a suspected malady, or as prognostic indicators for treatment success, survival, etc.

Samples can include multiple targets that can be specifically bound by a probe or reporter molecule. The targets can be nucleic acid sequences or proteins. In some examples, the target is a protein or nucleic acid molecule from a pathogen, such as a virus, bacteria, or intracellular parasite, such as from a viral genome. For example, a target protein may be produced from a target nucleic acid sequence associated with (e.g., correlated with, causally implicated in, etc.) a disease.

The skilled artisan will appreciate that PNA conjugates may be developed which are specific to any of the following targets:

In specific, non-limiting examples, a target protein is produced by a target nucleic acid sequence (e.g., genomic target nucleic acid sequence) associated with a neoplasm (for example, a cancer). Numerous chromosome abnormalities (including translocations and other rearrangements, amplification or deletion) have been identified in neoplastic cells, especially in cancer cells, such as B cell and T cell leukemias, lymphomas, breast cancer, colon cancer, neurological cancers and the like. Therefore, in some examples, at least a portion of the target molecule is produced by a nucleic acid sequence (e.g., genomic target nucleic acid sequence) amplified or deleted in at least a subset of cells in a sample.

In other examples, a target protein produced from a nucleic acid sequence (e.g., genomic target nucleic acid sequence) that is a tumor suppressor gene that is deleted (lost) in malignant cells. For example, the p16 region (including D9S1749, D9S1747, p16(INK4A), p14(ARF), D9S1748, p15(INK4B), and D9S1752) located on chromosome 9p21 is deleted in certain bladder cancers. Chromosomal deletions involving the distal region of the short arm of chromosome 1 (that encompasses, for example, SHGC57243, TP73, EGFL3, ABL2, ANGPTL1, and SHGC—1322), and the pericentromeric region (e.g., 19p13-19q13) of chromosome 19 (that encompasses, for example, MAN2B1, ZNF443, ZNF44, CRX, GLTSCR2, and GLTSCR1) are characteristic molecular features of certain types of solid tumors of the central nervous system.

Numerous other cytogenetic abnormalities that correlate with neoplastic transformation and/or growth are known to those of ordinary skill in the art. Target proteins that are produced by nucleic acid sequences (e.g., genomic target nucleic acid sequences), which have been correlated with neoplastic transformation and which are useful in the disclosed methods, also include the EGFR gene (7p12; e.g., GENBANK™ Accession No. NC—000007, nucleotides 55054219-55242525), the C-MYC gene (8q24.21; e.g., GENBANK™ Accession No. NC—000008, nucleotides 128817498-128822856), D5S271 (5p15.2), lipoprotein lipase (LPL) gene (8p22; e.g., GENBANK™ Accession No. NC—000008, nucleotides 19841058-19869049), RB1 (13q14; e.g., GENBANK™ Accession No. NC—000013, nucleotides 47775912-47954023), p53 (17p13.1; e.g., GENBANK™ Accession No. NC—000017, complement, nucleotides 7512464-7531642)), N-MYC (2p24; e.g., GENBANK™ Accession No. NC—000002, complement, nucleotides 151835231-151854620), CHOP (12q13; e.g., GENBANK™ Accession No. NC—000012, complement, nucleotides 56196638-56200567), FUS (16p11.2; e.g., GENBANK™ Accession No. NC—000016, nucleotides 31098954-31110601), FKHR (13p14; e.g., GENBANK™ Accession No. NC—000013, complement, nucleotides 40027817-40138734), as well as, for example: ALK (2p23; e.g., GENBANK™ Accession No. NC—000002, complement, nucleotides 29269144-29997936), Ig heavy chain, CCND1 (11q13; e.g., GENBANK™ Accession No. NC—000011, nucleotides 69165054.69178423), BCL2 (18q21.3; e.g., GENBANK™ Accession No. NC—000018, complement, nucleotides 58941559-59137593), BCL6 (3q27; e.g., GENBANK™ Accession No. NC—000003, complement, nucleotides 188921859-188946169), MALF1, AP1 (1p32-p31; e.g., GENBANK™ Accession No. NC—000001, complement, nucleotides 59019051-59022373), TOP2A (17q21-q22; e.g., GENBANK™ Accession No. NC—000017, complement, nucleotides 35798321-35827695), TMPRSS (21q22.3; e.g., GENBANK™ Accession No. NC—000021, complement, nucleotides 41758351-41801948), ERG (21q22.3; e.g., GENBANK™ Accession No. NC—000021, complement, nucleotides 38675671-38955488); ETV1 (7p21.3; e.g., GENBANK™ Accession No. NC—000007, complement, nucleotides 13897379-13995289), EWS (22q12.2; e.g., GENBANK™ Accession No. NC—000022, nucleotides 27994271-28026505); FLI1 (11q24.1-q24.3; e.g., GENBANK™ Accession No. NC—000011, nucleotides 128069199-128187521), PAX3 (2q35-q37; e.g., GENBANK™ Accession No. NC—000002, complement, nucleotides 222772851-222871944), PAX7 (1p36.2-p36.12; e.g., GENBANK™ Accession No. NC—000001, nucleotides 18830087-18935219), PTEN (10q23.3; e.g., GENBANK™ Accession No. NC—000010, nucleotides 89613175-89716382), AKT2 (19q13.1-q13.2; e.g., GENBANK™ Accession No. NC—000019, complement, nucleotides 45431556-45483036), MYCL1 (1p34.2; e.g., GENBANK™ Accession No. NC—000001, complement, nucleotides 40133685-40140274), REL (2p13-p12; e.g., GENBANK™ Accession No. NC—000002, nucleotides 60962256-61003682) and CSF1R (5q33-q35; e.g., GENBANK™ Accession No. NC—000005, complement, nucleotides 149413051-149473128).

EXAMPLES

The non-limiting examples presented herein each incorporate the use of PNA conjugates. Applicants submit that the PNA conjugates disclosed herein are suitable for use in IHC assays. Of course, as detailed herein, the PNA conjugates may be used in conjunction with other detectable specific binding entities and may be utilized in assays which combine IHC and ISH.

Example 1: PNA/Antibody Conjugation

Exemplary conjugation of PNA to goat-anti-mouse (GAM), goat-anti-rabbit (GAR), and mouse-anti-DIG, is described below:

(1) 100 micrograms of antibody (0.667 nmole) was diluted in PBS to 2 mg/mL and treated with 15 molar equivalent of SPDP-PEG-NHS (10 nmole from 10 mM DMSO stock solution) for 2 hours. SPDP-PEG-NHS was available from Quanta Biodesign, Ohio, USA (SPDP-dPEG8-NHS ester, product #10376).

(2) The labeled antibody was purified with 7 KD MW cutoff Zeba spin desalting columns from ThermoFisher (product #89882).

(3) 2 nmole PNA (8 uL from 251 µM PNA stock solution dissolved 1:1 (v/v) water DMF), was added to the antibody solution with the addition of 5 uL DMF, and 35 uL of PBS to yield approximately total of 100 uL of reaction solution. The mixture was incubated overnight at room temperature.

(4) The conjugates were then purified using Zeba spin desalting columns were then used to purify PNA-conjugated antibodies from the reaction mixture.

The purified PNA-conjugated antibodies were diluted in a suitable diluent before use.

Example 2 UV-Vis Measurement of Antibody-PNA Conjugates

Figure 2A:
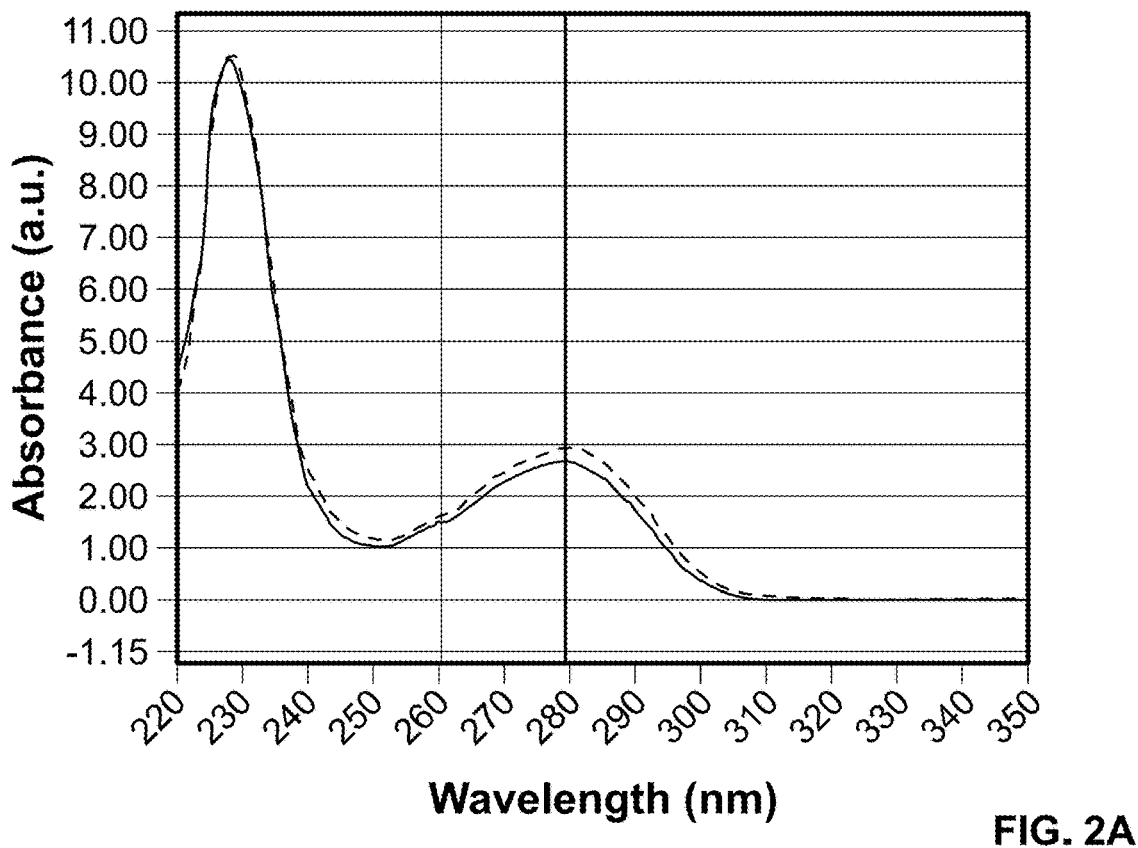
FIG. 2A illustrates the characterization of an antibody and corresponding PNA conjugate based on UV-Vis absorbance before PNA conjugation. Solid and dashed traces represent two different antibodies as examples.
Figure 2B:
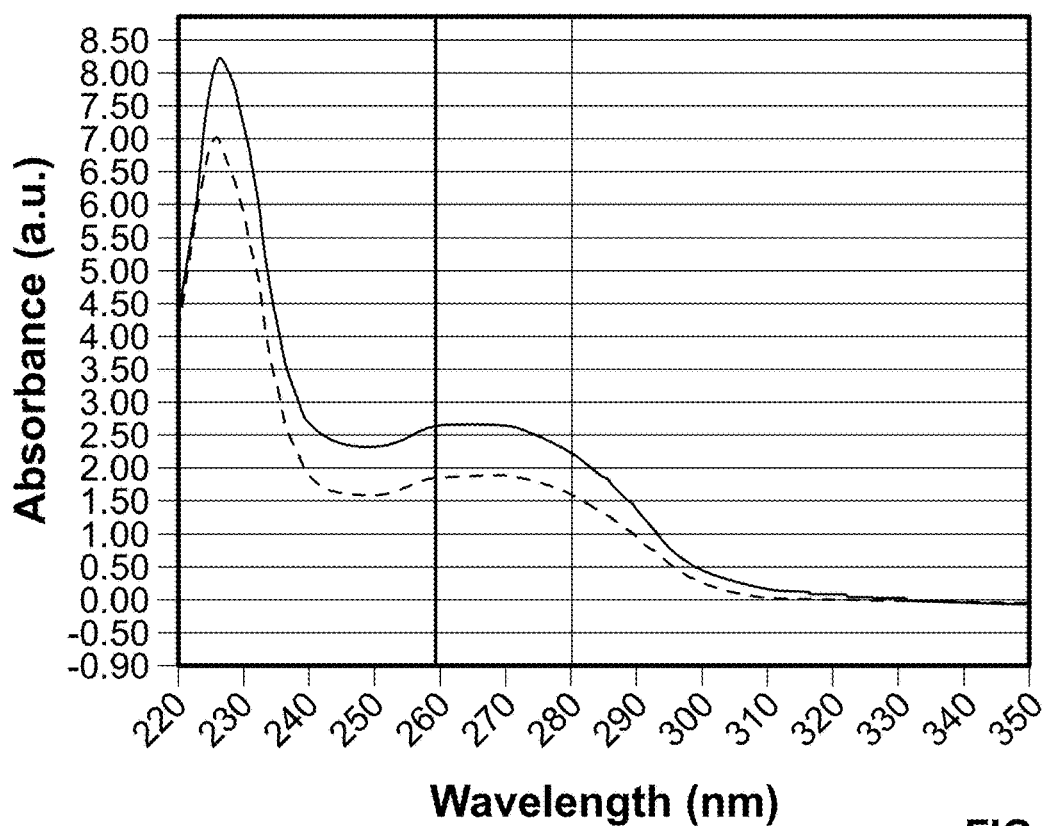
FIG. 2B illustrates the characterization of an antibody and corresponding PNA conjugate based on UV-Vis absorbance after PNA conjugation. Solid and dashed traces represent two different antibodies as examples.

The PNA-conjugated antibodies were characterized with UV-Vis absorbance. The increase of absorbance at 260 nm in the antibody-PNA conjugates indicated successful incorporation of PNA (see FIG. 2). The ratio of A260 to A280 nm may be used to qualitatively assess the efficiency of conjugation and potentially estimate the number of PNA oligomers per antibody.

Example 3: Detection of PNA-Antibody Conjugate Using SA-HRP

To prove that the conjugation of the short PNA (15 bases PNA, 10 bases PNA) oligo does not affect the binding affinity and specificity of the antibody, we performed IHC assays on tonsil tissues for different markers using PNA-conjugated secondary antibodies (primary and secondary). All IHC assays were run on Benchmark XT (Ventana) using protocols that were modified based on the specific assay. The PNA-conjugated antibodies were manually added as a titration at a volume of 100 uL.

Figure 3A:
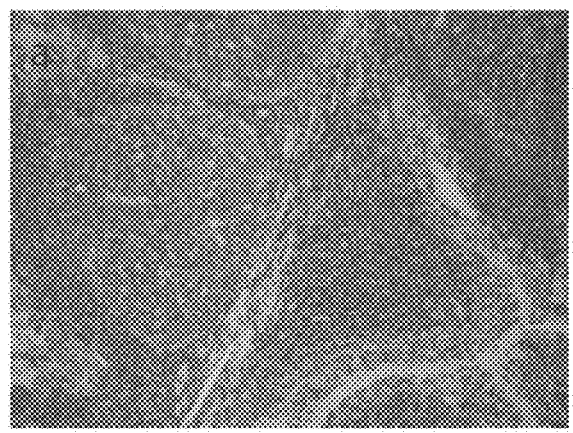
FIG. 3A illustrates IHC detection of a biotinylated PNA. Tonsil slides were treated with rabbit anti-CD45 followed by PNA-conjugated GAR. Biotin was then detected with SA-HRP and DAB deposition.
Figure 3B:
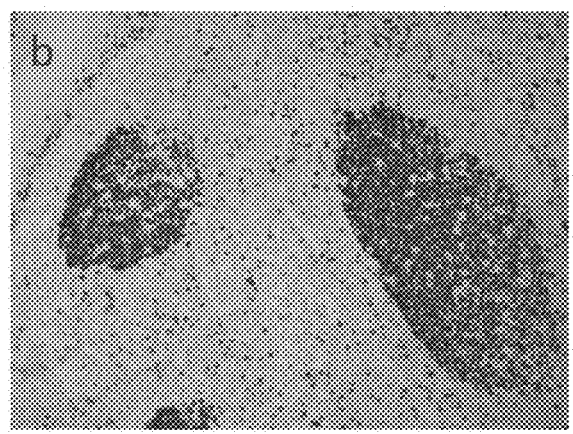
FIG. 3B illustrates IHC detection of a biotinylated PNA. Tonsil slides were treated with mouse anti-Ki67 followed by PNA-conjugated GAM. Biotin was then detected with SA-HRP and DAB deposition.
Figure 3C:
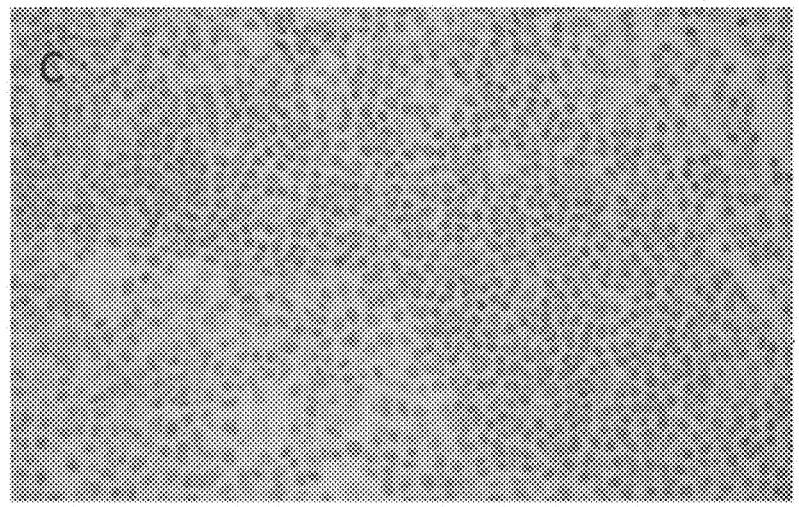
FIG. 3C illustrates IHC detection of a biotinylated PNA. Tonsil slides were treated with no primary antibody followed by PNA-conjugated GAM. Biotin was then detected with SA-HRP and DAB deposition.
Figure 3D:
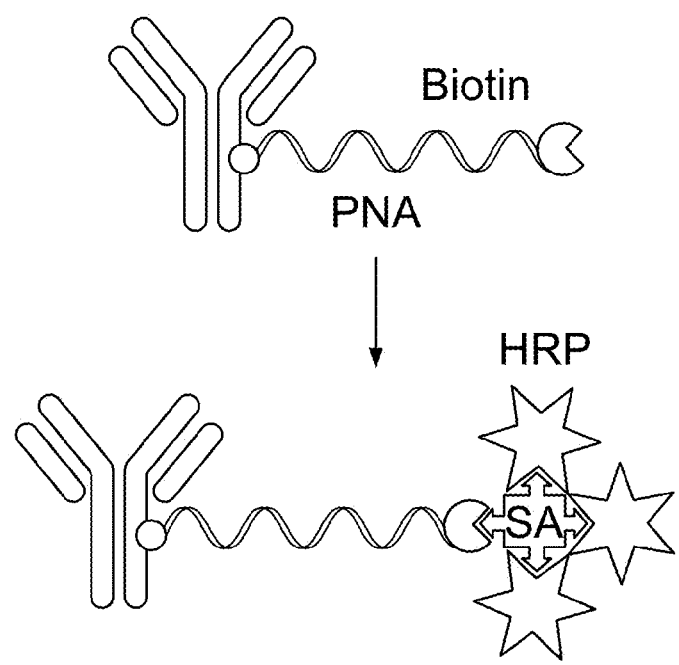
FIG. 3D provides a scheme illustrating detection strategy.

The biotin label on the PNA tag was directly detected. Two tonsil slides were incubated with anti-CD45 and anti-Ki67 primary antibodies followed by incubation with PNA-conjugated GAR and GAM secondary antibodies, respectively. The slides were then incubated with Streptavidin-HRP (SA-HRP) followed by DAB deposition (chromogenic detection). The markers were observed at their expected locations (FIGS. 3A and 3B). No background signal was observed when primary antibodies were omitted from the assays (FIG. 3C). Tonsil slides were also successfully stained against CK5/6 and using primary haptenated antibodies (Anti CK5/6:DIG) and secondary PNA-conjugated anti-hapten antibodies followed by SA-HRP and DAB deposition (FIG. 4A).

These first experiments provide strong evidence that PNA can be efficiently conjugated to secondary antibodies and the conjugation does not affect their binding affinity and specificity to the corresponding primary antibodies on tonsil slides.

The biotin label on the PNA tags (10 bases PNA) was directly detected. Tonsil slides were incubated with anti-CD8, anti-CD3, ant-PD-L1, anti-Ki67 conjugated primary antibodies. The slides were then incubated with Streptavidin-HRP (SA-HRP) followed by DAB deposition (chromogenic detection). The markers were observed at their expected locations (FIGS. 22A, 22B, 22C, 22D, 23, and 24).

Example 4A: Chemical Cleavage of the PNA Oligo

In some embodiments, the PNA-conjugate antibody is designed to allow multiplexed quantitative measurement of protein expression by methods such as Gyros technology or the NanoString nCounter platform, which is based on DNA counting. Therefore, the PNA sequence must be cleaved from the PNA-conjugated antibody after binding to the tissue to allow ex situ PNA counting. In this particular example, the PNA sequence was bound to the antibody via a disulfide bond, which could be chemically cleaved (e.g. by reduction of the disulfide bond) leading to PNA sequence release.

FIG. 5 shows tonsil slides stained for Ki67 and CD45 with primary antibodies followed by PNA-conjugated anti-species secondary antibodies and detected with SA-HRP DAB deposition. Incubating the slides with 20 mM TCEP (Tris (2-carboxyethyl)phosphine, reducing agent) before SA-HRP treatment resulted in the total loss of the brown staining color, which indicated the removal of the PNA tags.

Example 4B: Photo-Cleavage of the PNA Oligo

Tonsil slides were treated with primary antibody (rabbit Ki67), secondary antibody (GAR-PL-PNA, goat anti rabbit antibody with photocleavable PNA that has biotin on it). Slides were then irradiated with UV light (hand-held UV lamp, 365 nm) for different time periods. A control slide was not treated with UV and used for comparison. All slides were then treated with SA-HRP and DAB for detection.

Figure 13:
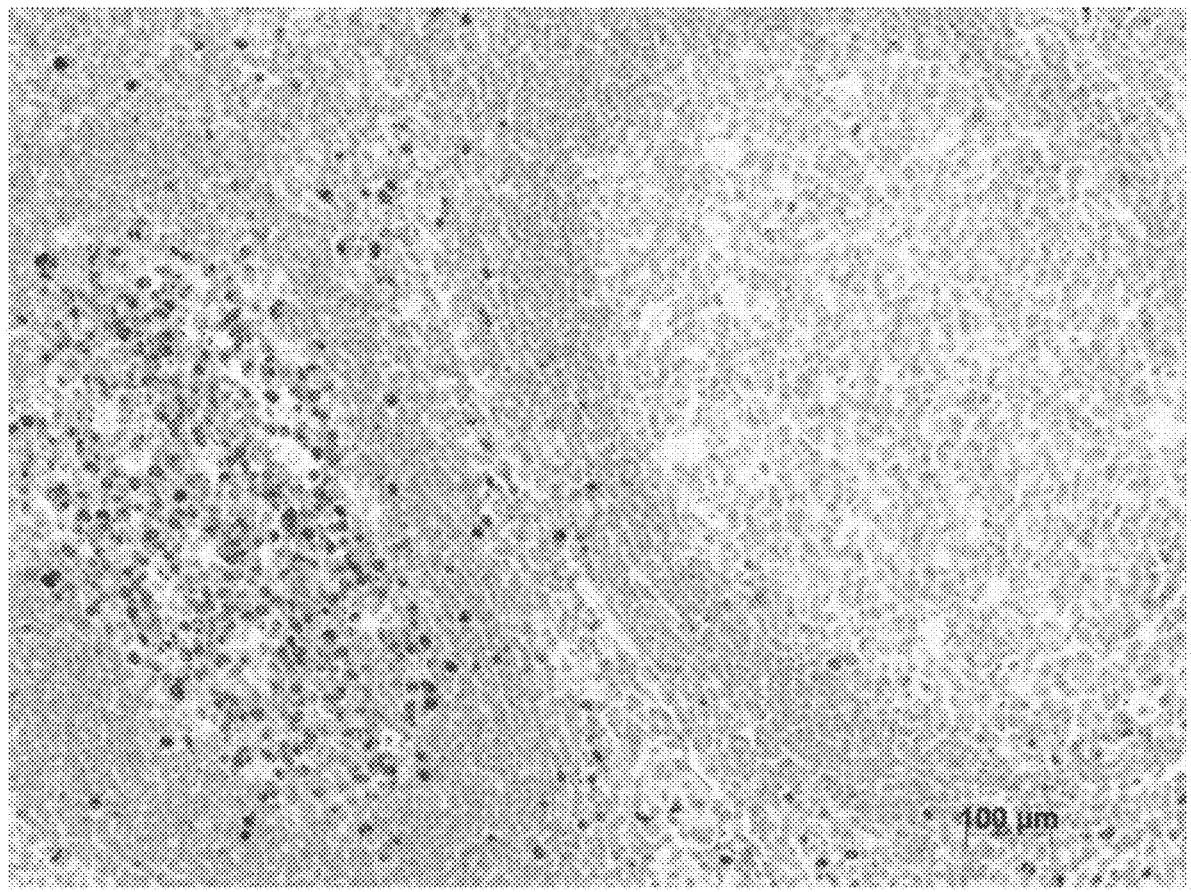
FIG. 13 illustrates the selective PNA photocleavage. Tonsil slide was treated with Ki67, then GAR-PL-PNA. The-indicated area was then irradiated with UV light from a laser capture microdissection instrument. LCM After washing the slide to remove the cleaved PNA, the staining was completed with SA-HRP and DAB detection. A UV irradiated germinal center lost color compared to non-irradiated germinal center on the same slide.

FIG. 12 shows that the irradiated slides do not have color indicating the photocleavage of the PNA sequence. In this experiment, the whole slides were irradiated with UV light. The cleavage of PNA from the whole slides can be achieved with chemical reduction of the disulfide bond. Light irradiation gives the possibility of selectively irradiating specific area of interest on the slide. To prove this concept, we have used a Laser Capture Microdissection (LCM) system to achieve selective irradiation. The LCM used UV light that came through an objective (high spatial precision) to cut specific area of the tissue (down to single cell). We have used UV to selectively irradiate specific areas on the tissue and photocleave the PNA. FIG. 13 illustrates tonsil slides where a germinal center was irradiated (-no staining) next to another germinal center that was not irradiated (positive staining). The LCM UV is 355 nm.

Example 5: Fluorescent Detection of the PNA/Antibody Conjugate Using SA-FITC

Besides chromogenic detection, biotin in the conjugate can also be fluorescently using SA-fluorophore. FIG. 6 shows a fluorescent image of a tonsil slide stained for Ki67 with a primary antibody followed by PNA-conjugated secondary antibody and detected with SA-FITC. SA-FITC binds biotin on the PNA sequence. The fluorescent signal is consistent with the localization of the Ki67 marker. This experiment demonstrated the versatility of detection schemes the PNA-conjugated antibody provides.

Example 6: Quantitative Measurement of PNA

Without wishing to be bound by any particular theory, it has been reported that the NanoString nCounter platform has the ability to potentially detect as high as 800 different DNA sequences allowing tremendous multiplexing capability for IHC once the antibody PNA conjugate is used. We assume that PNA can be detected in a similar manner to DNA as the detection scheme is based on the hybridization of a reporter strand to the target oligo (can presumably could be DNA or PNA). It is believed that the PNA oligomers can be significantly shorter than the standard DNA targets typically used with the NanoString nCounter platform (which are typically about 100 bases in length) because However, the presence of the biotin on the 3' end of the PNA excludes the need to use a capture strand. Moreover, the higher binding affinity of PNA to DNA compared to DNA to DNA is believed to provide enough stability to the relatively short PNA/DNA reporter duplex.

Figure 7A:
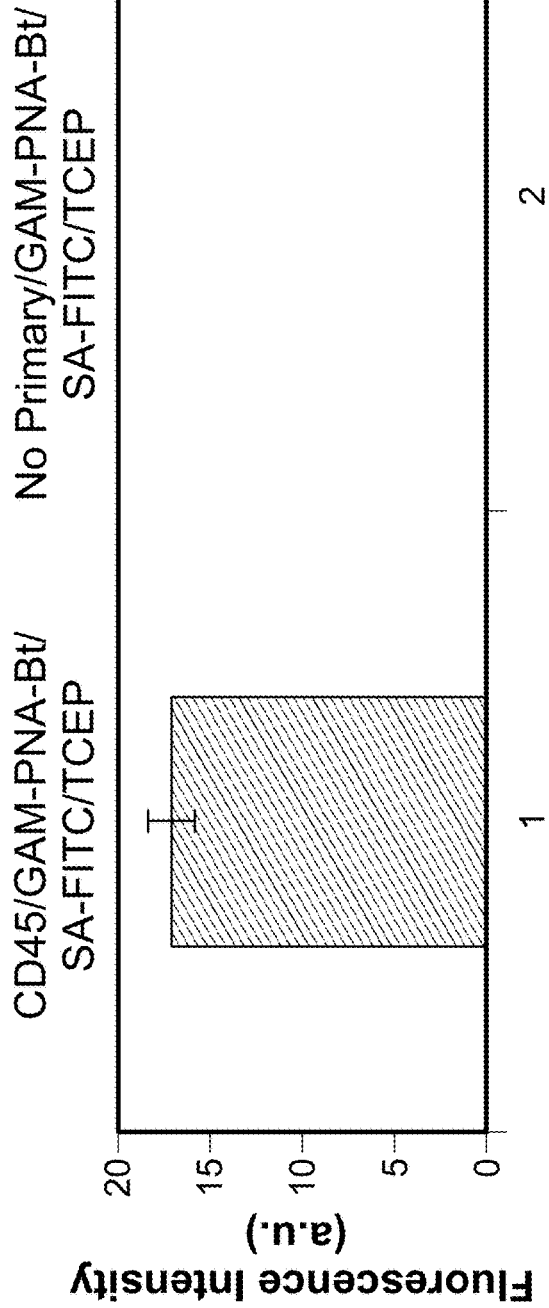
FIG. 7A sets forth a quantified measurement of antibody per slide based on cleaved PNA-SA-FITC fluorescence intensity. Bar graphs showing the fluorescence intensity of PNA-SA-FITC cleaved from a tonsil slide treated with mouse anti-CD45, PNA-conjugated GAM, followed by SA-FITC and finally incubated with 20 mM TCEP. The control is a tonsil slide treated the same as the experiment but without primary antibody FIG. 7B sets forth a quantified measurement of antibody per slide based on cleaved PNA-SA-FITC fluorescence intensity. The standard curve used to determine the concentration of PNA-SA-FITC cleaved from the experiment and control slides. Fluorescence intensities of sample and control are shown as mean±STDEV (N=3).
Figure 7B:
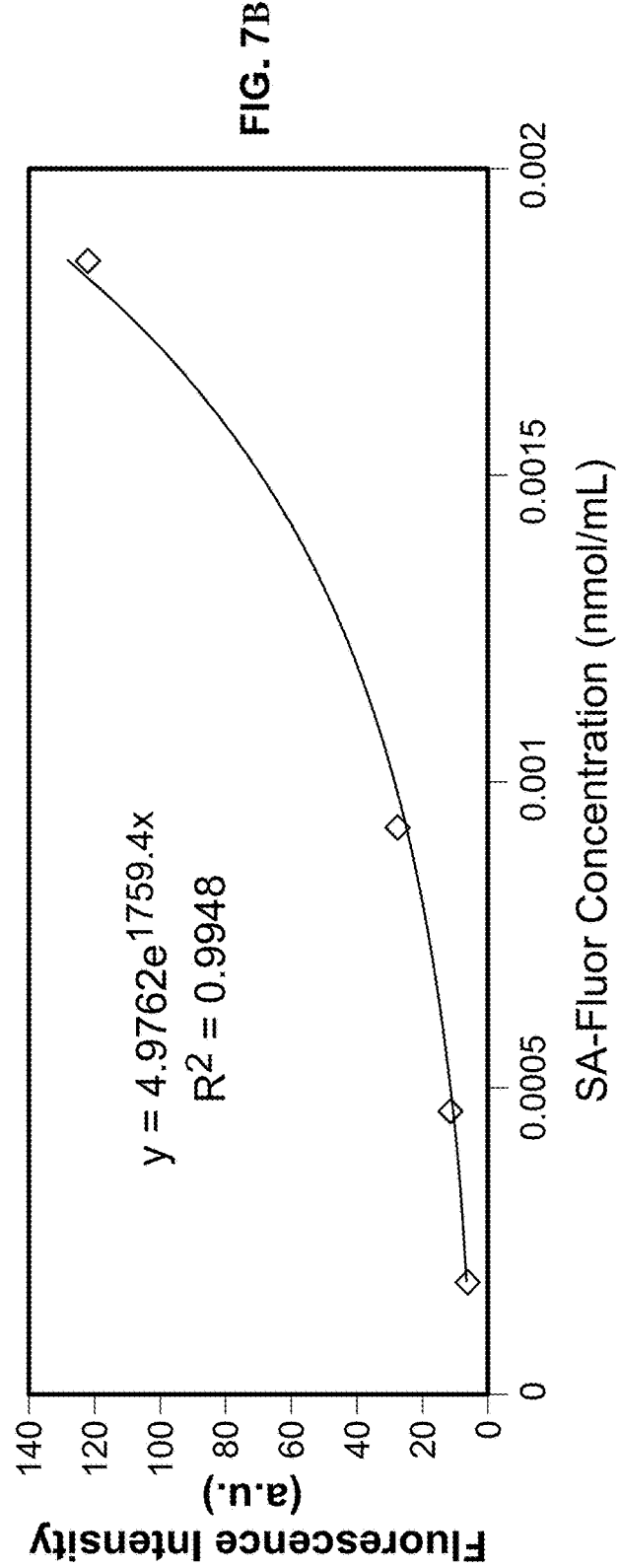
Figure 9A:
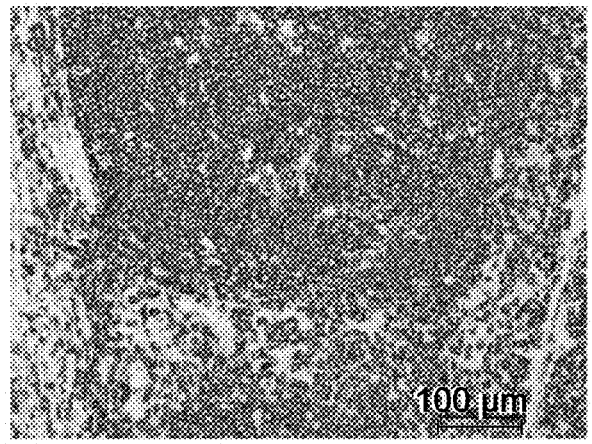
FIG. 9A illustrates chromogenic detection with compliment haptenated DNA. Tonsil slides treated with primary mouse-anti-CD2, and then incubated with PNA-conjugated GAM followed by hybridization with DIG-labeled DNA sequence that is compliment to the PNA tag. Finally, the slides were incubated with anti-DIG:HRP antibody and DAB deposition.
Figure 9B:
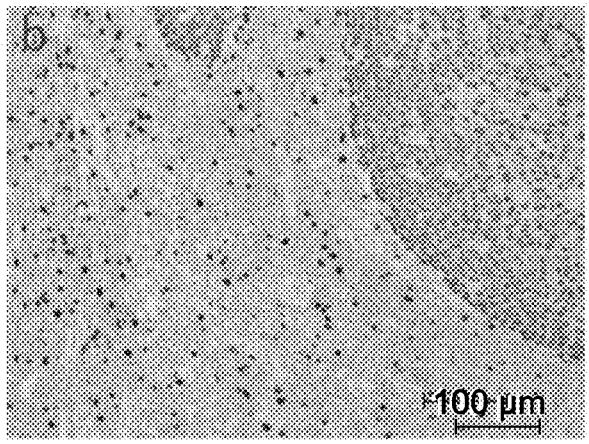
FIG. 9B illustrates chromogenic detection with compliment haptenated DNA. Tonsil slides treated with primary rabbit-anti-Ki67, and then incubated with PNA-conjugated GAR followed by hybridization with DIG-labeled DNA sequence that is compliment to the PNA tag. Finally, the slides were incubated with anti-DIG:HRP antibody and DAB deposition.
Figure 9C:
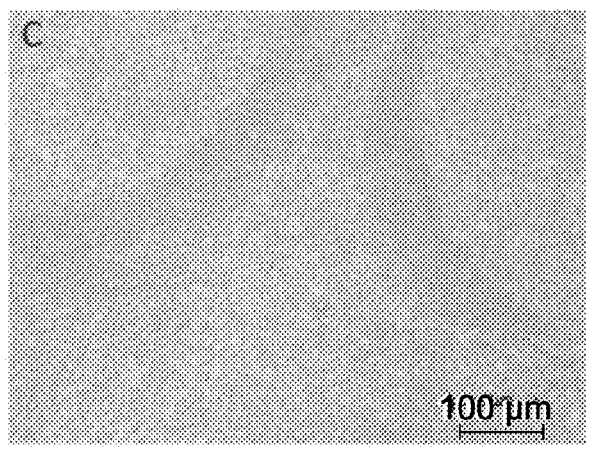
FIG. 9C illustrates tonsil slide treated in the same manner as FIGS. 9A and 9B but negative control with no primary antibody.
Figure 9D:
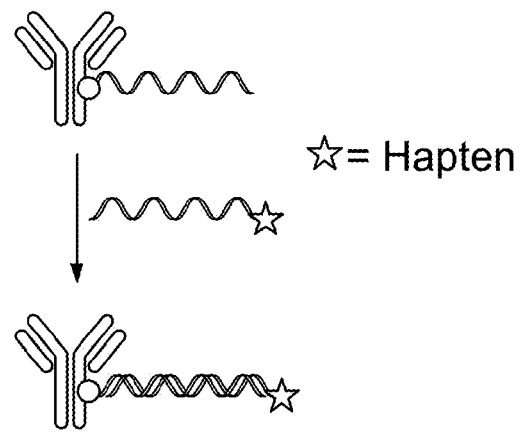
FIG. 9 D sets forth a schematic of a detection method using the haptenated DNA of FIGS. 9A-9C.

As a proof of concept, we showed that the fluorescently stained slide described in Example 8 herein could be incubated with TCEP (20 mM) to remove the PNA-SA-FITC. Released PNA-SA-FITC was measured based on the fluorescence intensity. The number of PNA-conjugated antibodies bound to the slide could then be estimated (FIG. 7)

Example 7: Detection of PNA Using Complement Fluorescent DNA

In the previous experiments the PNA was detected by staining against the biotin label. Complement DNA or PNA sequences carrying different labels (chromogenic, fluorogenic, etc.) may be used as alternative staining approaches. In this experiment, tonsil slides were incubated with rabbit anti-Ki67 primary antibody followed by PNA-conjugated GAR. Then, the slide was incubated with a DNA sequence complement to the PNA having fluorescent labels (e.g. FITC or Rhodamine). FIG. 8 shows that the slides were successfully stained through DNA hybridization. The fluorescent stains were consistent with the marker localization and no background signal was observed. DNA sequences were added as a manual titration at a concentration of about 185 nM and volume of about 100 uL.

DNA Sequences:

```
1:
                                    (SEQ ID NO: 16)
5'-CTGAAGATGGTTGAC/Rhodamine-3'

2:
                                    (SEQ ID NO: 17)
5'-FAM/CTGAAGATGGTTGAC-3'
```

This experiment demonstrates that PNA tag conjugated to the antibody is active and accessible through hybridization with complementary DNA on tissue. The two DNA sequences were complements to the same PNA, with each carrying a unique fluorophore. The two fluorophores were placed on different ends of the DNA sequence (FITC on the 5' end and Rhodamine on the 3' end). Consequently, FITC was located at the far end away from the antibody after hybridization with PNA, whereas Rhodamine was placed in the close proximity of the antibody. Positive staining was observed in both cases, proving the capability of detecting the PNA with hybridization to the complementary DNA sequences.

Example 8: Detection of PNA Using Complement Haptenated DNA

In this experiment, the complement DNA was labeled with a hapten (DIG). Two tonsil slides were incubated with rabbit anti-Ki67 and mouse anti-CD45 followed by PNA-conjugated GAR and PNA-conjugated GAM respectively. DIG-labeled complement DNA was incubated with both slides followed by HRP conjugated anti-DIG antibody and DAB deposition. DNA was added as a manual titration step at a concentration of about 185 nM and a volume of about 100 uL.

FIG. 9 shows that both slides were successfully stained and the staining pattern was consistent with the localization of the markers. No background signal was observed when primary antibodies were omitted.

```
DNA sequence:
                                    (SEQ ID NO: 18)
5'-CTGAAGATGGTTGAC/DIG/-3'
```

Example 9: PNA Ab Conjugation Via Click Chemistry

The steps of conjugating a PNA oligomer to an antibody are as follows:

(1) Antibody reduction to introduce sulfhydryl group (thiols): to 100 μg of Ab add 2.5 μL of 1 M DTT (Dithiothreitol) and incubate for 30 min (2) Remove excess DTT with Zeba desalting spin column (7 MWCO)

(3) Add DBCO-maleimide heterobifunctional linker (from click chemistry tools A108-25) at the ratio 1:12 Ab:linker and incubate overnight (4) Clean with Zeba column and add azide-PNA with ration 1:6 Ab:azide-PNA and incubate overnight.

(5) Clean with Zeba column.

Figure 17:
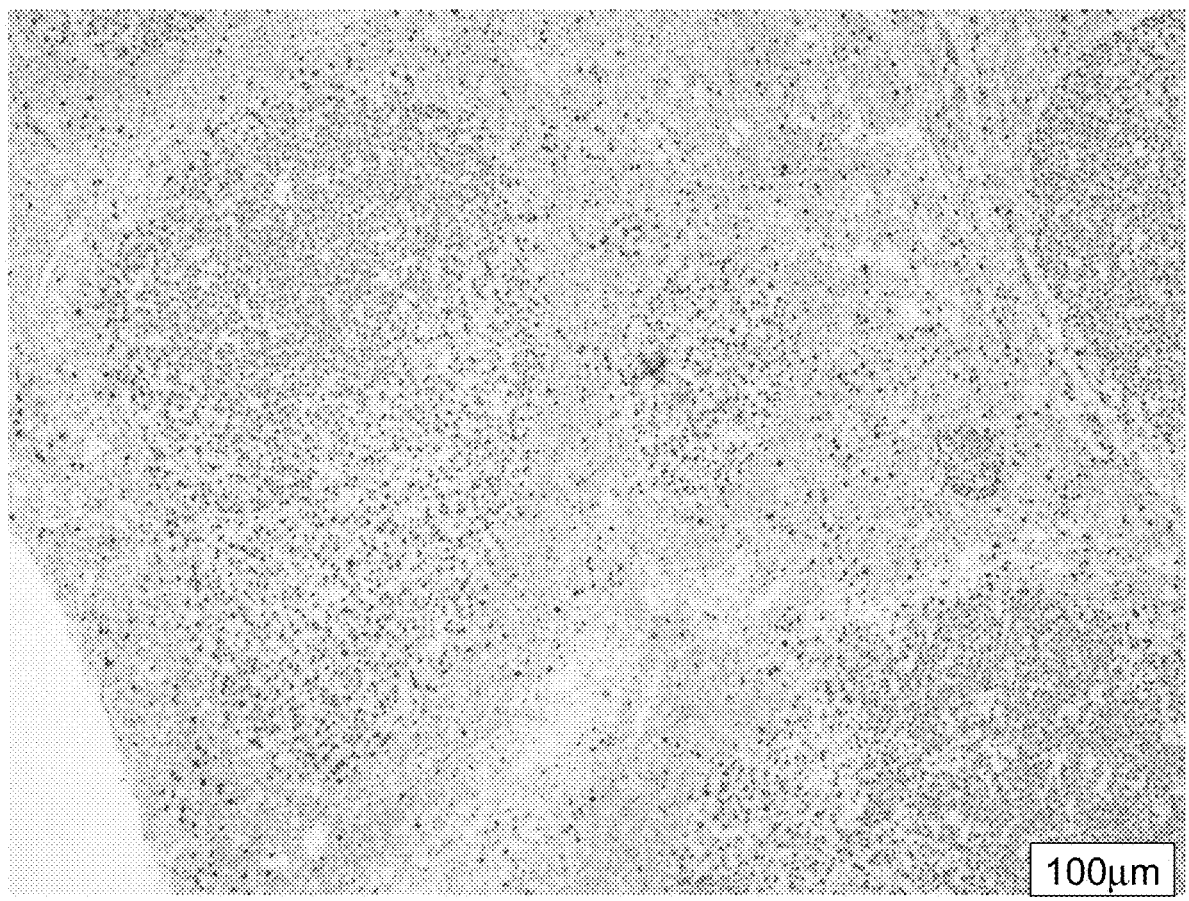
FIG. 17 illustrates tonsil tissue incubated with anti-Ki67 primary antibody (Rabbit mAb) and GAR-PNA (conjugated with click chemistry) secondary antibody and detected with SA-HRP. The image shows that the PNA was successfully conjugated via click chemistry to the Antibody.

FIG. 17 illustrates tonsil tissue incubated with anti-Ki67 primary antibody (Rabbit mAb) and GAR-PNA (conjugated with click chemistry) and detected with SA-HRP. The image shows that the PNA was successfully conjugated via click chemistry to the Antibody.

Example 10: PNA Ab Conjugation Via Maleimide Chemistry

The steps of conjugating a PNA oligomer to an antibody are as follows:

(1) Antibody reduction to introduce sulfhydryl group (thiol): to 100 μg of Ab add 2.5 of 1 M DTT (Dithiothreitol) and incubate for 30 min;

(2) Remove excess DTT with Zeba desalting spin column (7 MWCO);

(3) Add maleimide-PNA the ratio 1:6 Ab:maleimide DNA and incubate overnight; and (4) Clean with Zeba column

Example 11: PNA Quantification Using the Gyros Platform Technology

To demonstrated quantification of PNA using Gyros technology, a biotinylated PNA oligo (Bt-PNA) with concentration ranging from about 0.0274 nM to about 20 nM was tested (Table 1). For each concentration, a 1:2 ratio of Bt-PNA to a complementary single stranded DNA labeled with digoxigenin (DNA-DIG) was first hybridized at room temperature before being analyzed by Gyros in duplicates. The detection was achieved using Ms-anti-DIG followed by Alexa Fluor 647-GAM. A four-point curve (see Table 1) was fitted using the Gyros program, and a standard curve with $R^2$ greater than 0.998 was generated. Notably, the signal to background ratio (SB) of the lowest PNA concentration was about 10 about 10, suggesting very low background signal due to PNA or ssDNA.

TABLE 1

Standard Curve of PNA Having a Concentration Ranging from 0.0274 nM to 20 nM

| Sample ID | Exp Conc [nM] | Response | S/B | Calu Conc [nM] | Ave Conc, [nM] | CV Conc [%] | Bias [%] |
|---|---|---|---|---|---|---|---|
| Blank | 0 | 0.0576 | 1.07 | | | | |
| Blank | 0 | 0.0503 | 0.933 | | | | |
| Bt-PNA 1 | 0.0274 | 0.509 | 9.44 | 0.0263 | 0.0277 | 6.83 | −3.94 |
| Bt-PNA 1 | 0.0274 | 0.559 | 10.4 | 0.029 | 0.0277 | 6.83 | 5.81 |
| Bt-PNA 2 | 0.0823 | 1.43 | 26.6 | 0.0813 | 0.0804 | 1.51 | −1.27 |
| Bt-PNA 2 | 0.0823 | 1.41 | 26.1 | 0.0795 | 0.0804 | 1.51 | −3.36 |
| Bt-PNA 3 | 0.247 | 3.52 | 65.3 | 0.229 | 0.25 | 12 | −7.41 |
| Bt-PNA 3 | 0.247 | 4.07 | 75.5 | 0.271 | 0.25 | 12 | 9.73 |
| Bt-PNA 4 | 0.74 | 9.68 | 180 | 0.762 | 0.785 | 4.16 | 2.97 |
| Bt-PNA 4 | 0.74 | 10.2 | 188 | 0.808 | 0.785 | 4.16 | 9.21 |
| Bt-PNA 5 | 2.22 | 22.9 | 424 | 2.2 | 2.16 | 2.9 | −0.749 |
| Bt-PNA 5 | 2.22 | 22.1 | 410 | 2.11 | 2.16 | 2.9 | −4.74 |
| Bt-PNA 6 | 6.67 | 52 | 965 | 6.55 | 6.58 | 0.632 | −1.86 |
| Bt-PNA 6 | 6.67 | 52.4 | 971 | 6.6 | 6.58 | 0.632 | −0.975 |
| Bt-PNA 7 | 20 | 105 | 1940 | 19.1 | 20.3 | 8.55 | −4.44 |
| Bt-PNA 7 | 20 | 112 | 2080 | 21.6 | 20.3 | 8.55 | 7.86 |

To further demonstrate that PNA cleaved from the antibody conjugate can be quantified and the antibody can be further stained after PNA cleavage, experiments were performed as shown in FIG. 30. Three antibodies (Ki67, CD8 and PD-L1) were conjugated with Bt-PNA-1 and used for detecting the respective marker in normal tonsil tissue section. Most of the tissue processing steps were performed using a Ventana BenchMark XT autostainer. After standard antigen retrieval, PNA labeled primary antibodies were applied to tissue and incubated at about 37° C. for about 16 minutes. The slides were then removed from the tissue stainer and rinsed with reaction buffer and water. To each slide about 100 µL of 20 mM TCEP solution was added and incubated in a humidity box for about 20 minutes. Eighty microliters of the solution containing the cleaved PNA was collected and further quantified by Gyros (such as by using the techniques described herein). The slides after PNA cleavage were placed back in the autostainer and the primary antibody was further detected using a Ventana UltraView DAB universal detection kit.

The quantification of the cleaved Bt-PNA was achieved through hybridization with excess of complementary single stranded DNA-digoxigenin following the same procedure as previously described. The results were summarized in Table 2. The results clearly suggest that PNA from antibody conjugates for tissue staining can be successfully cleaved and further quantified using Gyros technology.

TABLE 2

Quantification of PNA Cleaved from Tissue

| | Sample ID | Exp Conc [pM] | Response | S/B | Cal Conc [pM] | Bias [%] |
|---|---|---|---|---|---|---|
| Standards | Blank | 0 | 0.748 | 1 | | |
| | Standard 1 | 5000 | 117 | 156 | 5020 | 0.394 |
| | Standard 2 | 1000 | 36.2 | 48.4 | 984 | −1.56 |
| | Standard 3 | 200 | 10.3 | 13.7 | 205 | 2.58 |
| | Standard 4 | 40 | 2.74 | 3.66 | 39.4 | −1.6 |
| | Standard 5 | 8 | 0.897 | 1.2 | 8.03 | 0.425 |
| Samples | Ki67 A[1] | unknown | 12.2 | 16.3 | 255 | N/A |
| | Ki67 B[1] | unknown | 14.4 | 19.2 | 310 | N/A |
| | CD8 A[1] | unknown | 1.85 | 2.47 | 23.3 | N/A |
| | CD8 B[1] | unknown | 2.39 | 3.19 | 32.9 | N/A |
| | PD-L1 A[1] | unknown | 4.62 | 6.18 | 76.6 | N/A |
| | PD-L1 B[1] | unknown | 4.94 | 6.6 | 83.2 | N/A |

TABLE 2-continued

Quantification of PNA Cleaved from Tissue

| | Sample ID | Exp Conc [pM] | Response | S/B | Cal Conc [pM] | Bias [%] |
|---|---|---|---|---|---|---|
| Negative Controls | Bt-PNA 125 nM[2] | | 1.01 | 1.35 | 9.67 | N/A |
| | Bt-PNA 12.5 nm[2] | | 0.529 | 0.707 | <8.00 | N/A |
| | DIG-DNA 250 nM[3] | | 0.553 | 0.739 | <8.00 | N/A |
| | TCEP solution | | 0.398 | 0.532 | <8.00 | N/A |

Figure 31A:
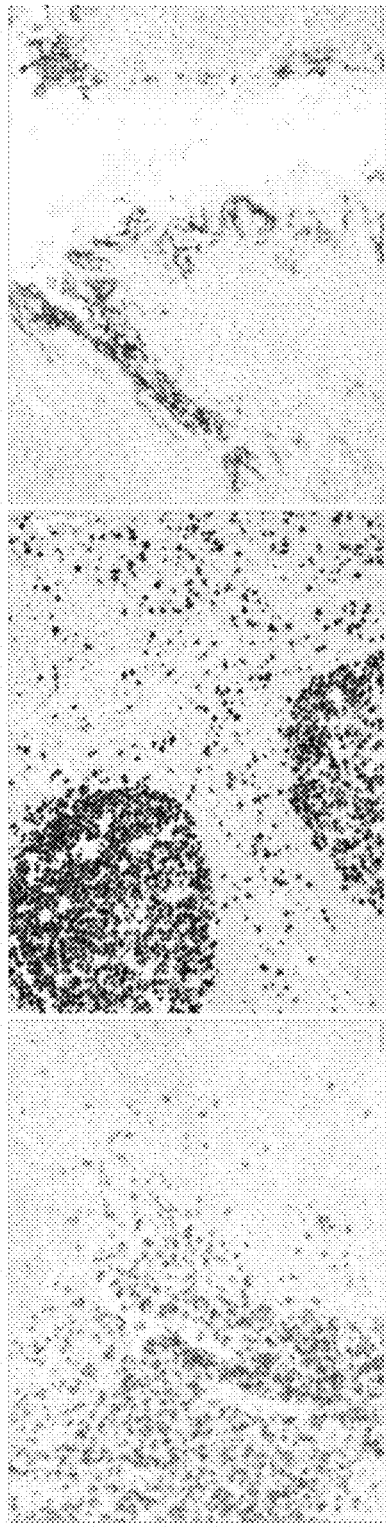
FIG. 31A illustrates IHC staining of the protein target following cleavage of a PNA sequence from a PNA-antibody conjugate.
Figure 31B:
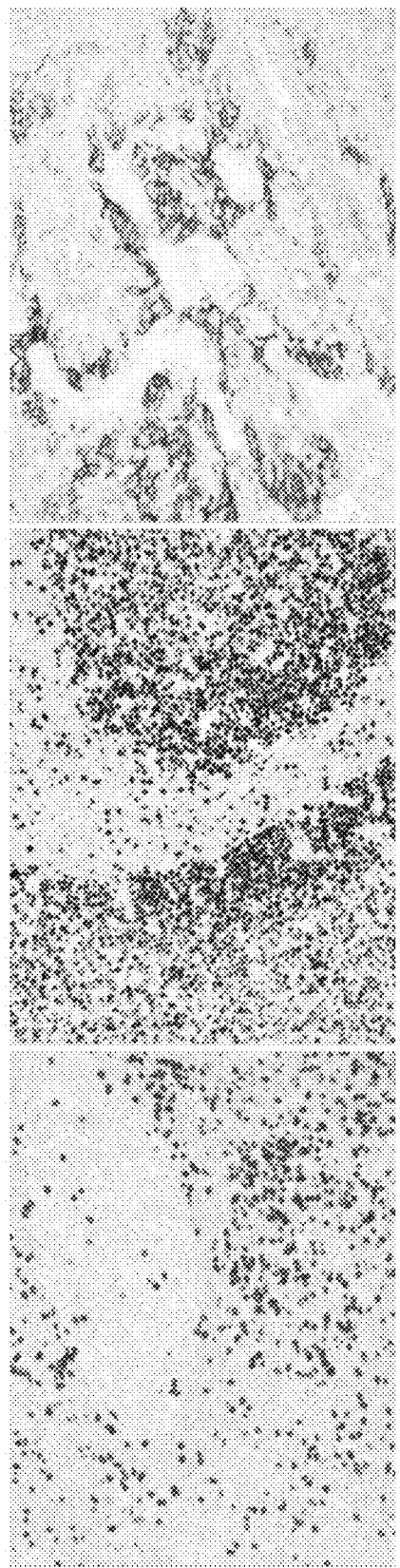
FIG. 31B illustrates IHC staining of the protein target following cleavage of a PNA sequence from a PNA-antibody conjugate.

[1]DIG-DNA final concentration = 250 nM
[2]NO DIG-DNA added, PNA only as negative control
[3]No Bt-PNA added, DIG-DNA only as negative control After PNA cleavage, the antibody on the very same tissue section can still be stained by standard IHC for visualization of the PNA encoded marker as shown in FIGS. 31A and 31B. Specific staining of each marker was observed, suggesting the cleavage conditions did not cause noticeable damage to the tissue or the binding of antibody to the marker. This result suggests a new way to combine quantification with visualization of spatial distribution of biomarkers in FFPE tissue, which is a unique advantage of the antibody-PNA conjugates.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary, to employ concepts of the various patents, applications and publications to provide yet further embodiments.

Although the disclosure herein has been described with reference to particular embodiments, it is to be understood that these embodiments are merely illustrative of the principles and applications of the present disclosure. It is therefore understood that numerous modifications may be made to the illustrative embodiments and that other arrangements may be devised without departing from the spirit and scope of the present disclosure as defined by the appended claims.

ADDITIONAL EMBODIMENTS

Additional Embodiment 1

A PNA conjugate having the structure of Formula (IC):

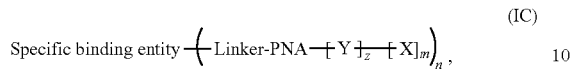

(IC)

wherein
- 'Specific binding entity' is selected from the group consisting of an antibody, an antibody fragment, a drug/antibody complex, and a nucleic acid;
- 'Linker' is a branched or unbranched, linear or cyclic, substituted or unsubstituted, saturated or unsaturated, group having between 2 and 80 carbon atoms, and optionally having one or more heteroatoms selected from O, N, or S;
- 'PNA' is a PNA sequence;
- X is selected from the group consisting of biotin, an enzyme, a chromogen, a fluorophore, a hapten, and a mass spectrometry tag;
- Y is a branched or unbranched, linear or cyclic, substituted or unsubstituted, saturated or unsaturated group having between 1 and 12 carbon atoms and optionally having one or more O, N, or S heteroatoms;
- m is 0 or an integer ranging from 1 to 6;
- z is 0 or 1; and
- n is an integer ranging from 1 to 12.

Additional Embodiment 2

The PNA conjugate of additional embodiment 1, wherein 'Specific binding entity' is a primary antibody.

Additional Embodiment 3

The PNA conjugate of additional embodiment 1, wherein 'Specific binding entity' is a secondary antibody.

Additional Embodiment 4

The PNA conjugate of additional embodiment 1, wherein X is biotin.

Additional Embodiment 5

The PNA conjugate of additional embodiment 1, wherein m is 0, z is 0, and n is greater than 1.

Additional Embodiment 6

The PNA conjugate of additional embodiment 5, wherein n is an integer ranging from between 2 and 6.

Additional Embodiment 7

The PNA conjugate of additional embodiment 1, wherein 'Linker' comprises at least one PEG group.

Additional Embodiment 8

The PNA conjugate of additional embodiment 1, wherein 'Linker' has the structure depicted in Formula (IIIa):

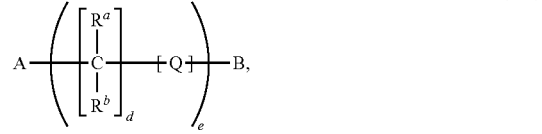

(IIIa)

wherein
- d and e are integers each independently ranging from 2 to 20;
- Q is a bond, O, S, or $N(R^c)(R^d)$;
- $R^a$ and $R^b$ are independently H, a $C_1$-$C_4$ alkyl group, F, Cl, or $N(R^c)(R^d)$;
- $R^c$ and $R^d$ are independently $CH_3$ or H; and
- A and B are independently a branched or unbranched, linear or cyclic, substituted or unsubstituted, saturated or unsaturated group having between 1 and 12 carbon atoms and optionally having one or more O, N, or S heteroatoms.

Additional Embodiment 9

The PNA conjugate of additional embodiment 8, wherein d and e are integers ranging from 2 to 6.

Additional Embodiment 10

The PNA conjugate of additional embodiment 8, wherein at least one of A or B comprises a cleavable moiety.

Additional Embodiment 11

The PNA conjugate of additional embodiment 10, wherein the cleavable moiety is a photocleavable group.

Additional Embodiment 12

The PNA conjugate of additional embodiment 10, wherein the cleavable moiety is a chemically cleavable group.

Additional Embodiment 13

The PNA conjugate of additional embodiment 1, wherein 'Specific binding entity' is an antibody, 'Linker' comprises at least one PEG group, m is 0, z is 0, and n is greater than 1.

Additional Embodiment 14

The PNA conjugate of additional embodiment 1, wherein 'Specific binding entity' is an antibody, 'Linker' comprises at least one PEG group, and n is greater than 1.

Additional Embodiment 15

The PNA conjugate of additional embodiment 14, wherein 'Linker' further comprises at least one cleavable group.

Additional Embodiment 16

The PNA conjugate of additional embodiment 15, wherein X is a hapten.

Additional Embodiment 17

A PNA oligomer having the structure of Formula (IB):

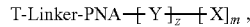
T-Linker-PNA$\mathrm{-\!\!+\!\!Y\!\!+\!\!\!\!\frac{}{z}\!\!+\!\!X]}_m$ ,                  (IB)

wherein
T is a group having between 1 and 4 carbon atoms and optionally substituted with O, N, or S and having a terminal reactive moiety;
'Linker' is a branched or unbranched, linear or cyclic, substituted or unsubstituted, saturated or unsaturated, group having between 2 and 80 carbon atoms, and optionally having one or more heteroatoms selected from O, N, or S;
'PNA' is a PNA sequence;
X is selected from the group consisting of biotin, an enzyme, a chromogen, a fluorophore, a hapten, and a mass spectrometry tag;
Y is a branched or unbranched, linear or cyclic, substituted or unsubstituted, saturated or unsaturated group having between 1 and 12 carbon atoms and optionally having one or more O, N, or S heteroatoms;
m is 0 or an integer ranging from 1 to 6; and
z is 0 or 1.

Additional Embodiment 18

The PNA oligomer of additional embodiment 17, wherein X is biotin.

Additional Embodiment 19

The PNA oligomer of additional embodiment 17, wherein m is 0, z is 0, and n is greater than 1.

Additional Embodiment 20

The PNA oligomer of additional embodiment 19, wherein n is an integer ranging from between 2 and 6.

Additional Embodiment 21

The PNA oligomer of additional embodiment 17, wherein 'Linker' comprises at least one PEG group.

Additional Embodiment 22

The PNA oligomer of additional embodiment 17, wherein 'Linker' has the structure depicted in Formula (IIIa):

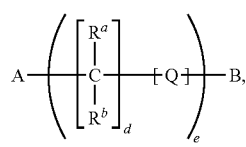

wherein
d and e are integers each independently ranging from 2 to 20;
Q is a bond, O, S, or N(R$^c$)(R$^d$);
R$^a$ and R$^b$ are independently H, a C$_1$-C$_4$ alkyl group, F, Cl, or N(R$^c$)(R$^d$);
R$^c$ and R$^d$ are independently CH$_3$ or H; and
A and B are independently a branched or unbranched, linear or cyclic, substituted or unsubstituted, saturated or unsaturated group having between 1 and 12 carbon atoms and optionally having one or more O, N, or S heteroatoms.

Additional Embodiment 23

The PNA oligomer of additional embodiment 22, wherein d and e are integers ranging from 2 to 6.

Additional Embodiment 24

The PNA oligomer of additional embodiment 22, wherein at least one of A or B comprises a cleavable moiety.

Additional Embodiment 25

The PNA oligomer of additional embodiment 24, wherein the cleavable moiety is a photocleavable group.

Additional Embodiment 26

The PNA oligomer of additional embodiment 24, wherein the cleavable moiety is a chemically cleavable group.

Additional Embodiment 27

A PNA conjugate comprising the PNA oligomer of any of additional embodiments 17 to 26 and a specific binding entity.

Additional Embodiment 28

The PNA conjugate of additional embodiment 27, wherein the specific binding entity is a primary antibody; and wherein the PNA sequence comprises between 5 and 30 bases.

Additional Embodiment 29

A method of synthesizing a PNA conjugate comprising reacting the PNA oligomer of any of additional embodiments 17 to 26 with a specific binding entity.

Additional Embodiment 30

A method of detecting a target in a sample, comprising:
contacting the sample with a first PNA conjugate, the first PNA conjugate having the structure of Formula (IC):

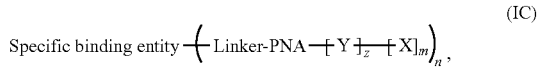

wherein
'Specific binding entity' is selected from the group consisting of an antibody, an antibody fragment, a drug/antibody complex, and a nucleic acid;

'Linker' is a branched or unbranched, linear or cyclic, substituted or unsubstituted, saturated or unsaturated, group having between 2 and 80 carbon atoms, and optionally having one or more heteroatoms selected from O, N, or S;
'PNA' is a PNA sequence;
X is selected from the group consisting of biotin, an enzyme, a chromogen, a fluorophore, a hapten, and a mass spectrometry tag;
Y is a branched or unbranched, linear or cyclic, substituted or unsubstituted, saturated or unsaturated group having between 1 and 12 carbon atoms and optionally having one or more O, N, or S heteroatoms;
m is 0 or an integer ranging from 1 to 6;
z is 0 or 1; and
n is an integer ranging from 1 to 12; and
contacting the sample with first detection reagents to facilitate detection of the PNA conjugate.

Additional Embodiment 31

The method of additional embodiment 30, wherein the 'Specific binding entity' is a primary antibody and wherein the primary antibody is specific to a first target.

Additional Embodiment 32

The method of additional embodiment 30, wherein the 'Specific binding entity' is a secondary antibody, and wherein the method further comprises the step of contacting the sample with a primary antibody specific for a first target prior to contacting the sample with the first PNA conjugate, and wherein the first PNA conjugate is specific to the first primary antibody.

Additional Embodiment 33

The method of additional embodiment 30, wherein the first detection reagents are anti-label antibodies specific to a label of the PNA conjugate.

Additional Embodiment 34

The method of additional embodiment 33, wherein the label is a hapten and the anti-label antibodies are anti-hapten antibodies.

Additional Embodiment 35

The method of additional embodiment 30, wherein the detection reagents comprise a PNA or DNA sequence complementary to a PNA sequence of the first PNA conjugate, the complementary PNA or DNA sequence conjugated to a reporter moiety.

Additional Embodiment 36

The method of additional embodiment 35, wherein the reporter moiety is a fluorophore.

Additional Embodiment 37

The method of additional embodiment 35, wherein the reporter moiety is a hapten, and where the method further comprises contacting the sample with anti-hapten antibodies specific to the hapten of the complementary PNA or DNA sequence.

Additional Embodiment 38

A method of detecting a target in a sample, comprising: contacting the sample with a first PNA conjugate, the first PNA conjugate having the structure of Formula (IC):

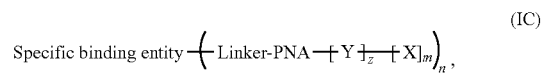

wherein
'Specific binding entity' is selected from the group consisting of an antibody, an antibody fragment, a drug/antibody complex, and a nucleic acid;
'Linker' is a branched or unbranched, linear or cyclic, substituted or unsubstituted, saturated or unsaturated, group having between 2 and 80 carbon atoms, and optionally having one or more heteroatoms selected from O, N, or S; the 'Linker' further comprising a cleavable group;
'PNA' is a PNA sequence;
X is selected from the group consisting of biotin, an enzyme, a chromogen, a fluorophore, a hapten, and a mass spectrometry tag;
Y is a branched or unbranched, linear or cyclic, substituted or unsubstituted, saturated or unsaturated group having between 1 and 12 carbon atoms and optionally having one or more O, N, or S heteroatoms;
m is 0;
z is 0; and
n is an integer ranging from 1 to 12; and
contacting the sample with a reagent to cleave the cleavable group on the 'Linker,' and
quantifying an amount of the cleaved 'PNA' sequence.

Additional Embodiment 39

The method of additional embodiment 38, wherein the quantification of the amount of the PNA sequence is performed using NanoString nCounter technology, Gyros technology, or mass spectrometry.

Additional Embodiment 40

The method of additional embodiment 38, wherein the cleavable group is selected from the group consisting of a photocleavable group, a chemically cleavable group, or an enzymatically cleavable group.

Additional Embodiment 41

The method of additional embodiment 38, further comprising visualizing the Specific Binding Entity from which the PNA sequence was cleaved.

Additional Embodiment 42

A conjugate having the structure of Formula (I):

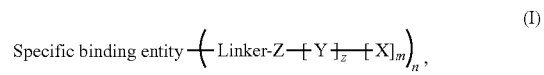

wherein
'Specific binding entity' is selected from the group consisting of an antibody, an antibody fragment, a drug/antibody complex, and a nucleic acid;
'Linker' is a branched or unbranched, linear or cyclic, substituted or unsubstituted, saturated or unsaturated, group having between 2 and 80 carbon atoms, and optionally having one or more heteroatoms selected from O, N, or S;
Z is selected from the group consisting of a PNA sequence, an uncharged DNA sequence, and a DNA sequence comprising charged and uncharged bases;
X is selected from the group consisting of biotin, an enzyme, a chromogen, a fluorophore, a hapten, and a mass spectrometry tag;
Y is a branched or unbranched, linear or cyclic, substituted or unsubstituted, saturated or unsaturated group having between 1 and 12 carbon atoms and optionally having one or more O, N, or S heteroatoms;
m is 0 or an integer ranging from 1 to 6;
z is 0 or 1; and
n is an integer ranging from 1 to 12.

Additional Embodiment 43

The conjugate of additional embodiment 42, wherein the conjugate of Formula (I) has the structure of Formula (IC):

wherein PNA is a PNA sequence.

Additional Embodiment 44

The conjugate of additional embodiment 42, wherein Z comprises a DNA sequence comprising only uncharged DNA bases.

Additional Embodiment 45

The conjugate of additional embodiment 42, wherein Z comprises a DNA sequence comprising a mixture of charged and uncharged bases.

Additional Embodiment 46

The conjugate of additional embodiment 45, wherein at least 50% of the bases in the DNA sequence are uncharged.

Additional Embodiment 47

A conjugate of Formula (II):

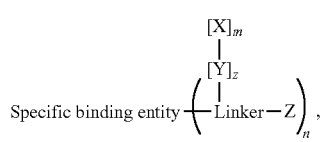

wherein
'Specific binding entity' is selected from the group consisting of an antibody, an antibody fragment, a drug/antibody complex, and a nucleic acid;
'Linker' is a branched or unbranched, linear or cyclic, substituted or unsubstituted, saturated or unsaturated, group having between 2 and 80 carbon atoms, and optionally having one or more heteroatoms selected from O, N, or S;
Z is selected from the group consisting of a PNA sequence, an uncharged DNA sequence, and a DNA sequence comprising charged and uncharged bases;
X is selected from the group consisting of biotin, an enzyme, a chromogen, a fluorophore, a hapten, and a mass spectrometry tag;
Y is a branched or unbranched, linear or cyclic, substituted or unsubstituted, saturated or unsaturated group having between 1 and 12 carbon atoms and optionally having one or more O, N, or S heteroatoms;
m is 0 or an integer ranging from 1 to 6;
z is 0 or 1; and
n is an integer ranging from 1 to 12.

Additional Embodiment 48

The conjugate of additional embodiment 47, wherein the 'Specific Binding Entity' is a primary antibody.

Additional Embodiment 49

The conjugate of additional embodiment 48, wherein Z is a PNA sequence having between about 5 and about 30 bases.

Additional Embodiment 50

The conjugate of additional embodiment 48, wherein Z is a PNA sequence having about 10 bases.

Additional Embodiment 51

A PNA conjugate having the structure of Formula (IC):

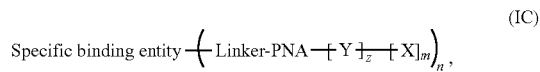

wherein
'Specific binding entity' is selected from the group consisting of an antibody, an antibody fragment, a drug/antibody complex, and a nucleic acid;
'Linker' is a branched or unbranched, linear or cyclic, substituted or unsubstituted, saturated or unsaturated, group having between 2 and 80 carbon atoms, and optionally having one or more heteroatoms selected from O, N, or S;
'PNA' is a PNA sequence;
X is selected from the group consisting of biotin, an enzyme, a chromogen, a fluorophore, a hapten, and a mass spectrometry tag;
Y is a branched or unbranched, linear or cyclic, substituted or unsubstituted, saturated or unsaturated group having between 1 and 12 carbon atoms and optionally having one or more O, N, or S heteroatoms;
m is 0 or an integer ranging from 1 to 6;
z is 0 or 1; and
n is an integer ranging from 1 to 12;

wherein the PNA sequence is selected from the group consisting of SEQ ID NO: 1, SEQ ID NO:2, SEQ ID NO:3, SEQ ID NO: 4, SEQ ID NO: 5, SEQ ID NO: 6, and SEQ ID NO: 7.

Additional Embodiment 52

The PNA conjugate of additional embodiment 51, wherein the specific binding entity is an antibody.

Additional Embodiment 53

The PNA conjugate of additional embodiment 52, wherein the antibody is a primary antibody.

Additional Embodiment 54

The PNA conjugate of additional embodiment 51, wherein the linker comprises a photocleavable group.

The invention claimed is:

1. A peptide nucleic acid conjugate having the structure of Formula (IC):

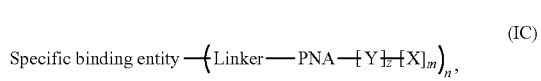
(IC)

wherein
'Specific binding entity' is selected from the group consisting of an antibody, an antibody fragment, a drug/antibody complex, and a nucleic acid;
'Linker' is a branched or unbranched, linear or cyclic, substituted or unsubstituted, saturated or unsaturated, group having between 2 and 80 carbon atoms, and optionally having one or more heteroatoms selected from O, N, or S;
'PNA' is a peptide nucleic acid sequence;
X is selected from the group consisting of biotin, an enzyme, a chromogen, a fluorophore, a hapten, and a mass spectrometry tag;
Y is a branched or unbranched, linear or cyclic, substituted or unsubstituted, saturated or unsaturated group having between 1 and 12 carbon atoms and optionally having one or more O, N, or S heteroatoms;
m is an integer ranging from 1 to 6;
z is 1; and
n is an integer ranging from 1 to 12.

2. The peptide nucleic acid conjugate of claim 1, wherein 'Specific binding entity' is selected from one of a primary antibody or a secondary antibody.

3. The peptide nucleic acid conjugate of claim 1, wherein X is biotin.

4. The peptide nucleic acid conjugate of claim 1, wherein m is 1, z is 1, and n is greater than 1.

5. The peptide nucleic acid conjugate of claim 4, wherein n is an integer ranging from between 2 and 6.

6. The peptide nucleic acid conjugate of claim 1, wherein 'Linker' comprises at least one PEG group.

7. The peptide nucleic acid conjugate of claim 1, wherein 'Linker' has the structure depicted in Formula (IIIa):

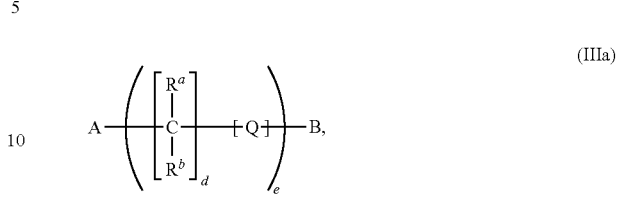
(IIIa)

wherein
d and e are integers each independently ranging from 2 to 20;
Q is a bond, O, S, or $N(R^c)(R^d)$;
$R^a$ and $R^b$ are independently H, a $C_1$-$C_4$ alkyl group, F, Cl, or $N(R^c)(R^d)$;
$R^c$ and $R^d$ are independently $CH_3$ or H; and
A and B are independently a branched or unbranched, linear or cyclic, substituted or unsubstituted, saturated or unsaturated group having between 1 and 12 carbon atoms and optionally having one or more O, N, or S heteroatoms.

8. The peptide nucleic acid conjugate of claim 7, wherein d and e are integers ranging from 2 to 6.

9. The peptide nucleic acid conjugate of claim 7, wherein at least one of A or B comprises a cleavable moiety.

10. The peptide nucleic acid conjugate of claim 1, wherein 'Specific binding entity' is an antibody, 'Linker' comprises at least one PEG group, and n is greater than 1.

11. The peptide nucleic acid conjugate of claim 1, wherein 'Specific binding entity' is an antibody, 'Linker' comprises at least one PEG group, and n is greater than 1.

12. The peptide nucleic acid conjugate of claim 1, wherein X is a hapten.

* * * * *

SEQUENCE LISTING

```
<160> NUMBER OF SEQ ID NOS: 22

<210> SEQ ID NO 1
<211> LENGTH: 15
<212> TYPE: DNA
<213> ORGANISM: Artificial Sequence
<220> FEATURE:
<223> OTHER INFORMATION: Synthetic: Synthetic PNA sequence

<400> SEQUENCE: 1
gtcaaccatc ttcag                                                          15

<210> SEQ ID NO 2
<211> LENGTH: 15
<212> TYPE: DNA
<213> ORGANISM: Artificial Sequence
<220> FEATURE:
<223> OTHER INFORMATION: Synthetic: Synthetic PNA sequence

<400> SEQUENCE: 2
ttagtccaac tggca                                                          15

<210> SEQ ID NO 3
<211> LENGTH: 12
<212> TYPE: DNA
<213> ORGANISM: Artificial Sequence
<220> FEATURE:
<223> OTHER INFORMATION: Synthetic: Synthetic PNA sequence

<400> SEQUENCE: 3
cattcaaatc cc                                                             12

<210> SEQ ID NO 4
<211> LENGTH: 10
<212> TYPE: DNA
<213> ORGANISM: Artificial Sequence
<220> FEATURE:
<223> OTHER INFORMATION: Synthetic: Synthetic PNA sequence

<400> SEQUENCE: 4
ccatcttcag                                                                10

<210> SEQ ID NO 5
<211> LENGTH: 10
<212> TYPE: DNA
<213> ORGANISM: Artificial Sequence
<220> FEATURE:
<223> OTHER INFORMATION: Synthetic: Synthetic PNA sequence

<400> SEQUENCE: 5
ttagtccaac                                                                10

<210> SEQ ID NO 6
<211> LENGTH: 10
<212> TYPE: DNA
<213> ORGANISM: Artificial Sequence
```

```
<220> FEATURE:
<223> OTHER INFORMATION: Synthetic: Synthetic PNA sequence

<400> SEQUENCE: 6
ggtagaagtc                                                              10

<210> SEQ ID NO 7
<211> LENGTH: 10
<212> TYPE: DNA
<213> ORGANISM: Artificial Sequence
<220> FEATURE:
<223> OTHER INFORMATION: Synthetic: Synthetic PNA sequence

<400> SEQUENCE: 7
aatcaggttg                                                              10

<210> SEQ ID NO 8
<211> LENGTH: 15
<212> TYPE: DNA
<213> ORGANISM: Artificial Sequence
<220> FEATURE:
<223> OTHER INFORMATION: Synthetic: Synthetic PNA conjugate
<220> FEATURE:
<221> NAME/KEY: modified_base
<222> LOCATION: (1)..(1)
<223> OTHER INFORMATION: Biotin-O on 5' end
<220> FEATURE:
<221> NAME/KEY: modified_base
<222> LOCATION: (15)..(15)
<223> OTHER INFORMATION: Lys(C6SH) on 3' end

<400> SEQUENCE: 8
gtcaaccatc ttcag                                                        15

<210> SEQ ID NO 9
<211> LENGTH: 15
<212> TYPE: DNA
<213> ORGANISM: Artificial Sequence
<220> FEATURE:
<223> OTHER INFORMATION: Synthetic: Synthetic PNA conjugate
<220> FEATURE:
<221> NAME/KEY: modified_base
<222> LOCATION: (1)..(1)
<223> OTHER INFORMATION: Biotin-O on 5' end
<220> FEATURE:
<221> NAME/KEY: modified_base
<222> LOCATION: (15)..(15)
<223> OTHER INFORMATION: Lys(C6SH) on 3' end

<400> SEQUENCE: 9
ttagtccaac tggca                                                        15

<210> SEQ ID NO 10
<211> LENGTH: 15
<212> TYPE: DNA
<213> ORGANISM: Artificial Sequence
<220> FEATURE:
<223> OTHER INFORMATION: Synthetic: Synthetic PNA conjugate
<220> FEATURE:
<221> NAME/KEY: modified_base
<222> LOCATION: (1)..(1)
<223> OTHER INFORMATION: Biotin-O on 5' end
<220> FEATURE:
<221> NAME/KEY: modified_base
<222> LOCATION: (15)..(15)
<223> OTHER INFORMATION: PL-Lys(C6SH) on 3' end

<400> SEQUENCE: 10
cattcaaatc cccga                                                        15
```

```
<210> SEQ ID NO 11
<211> LENGTH: 15
<212> TYPE: DNA
<213> ORGANISM: Artificial Sequence
<220> FEATURE:
<223> OTHER INFORMATION: Synthetic: Synthetic PNA conjugate
<220> FEATURE:
<221> NAME/KEY: modified_base
<222> LOCATION: (1)..(1)
<223> OTHER INFORMATION: Biotin-O on 5' end
<220> FEATURE:
<221> NAME/KEY: modified_base
<222> LOCATION: (15)..(15)
<223> OTHER INFORMATION: Lys(C6SH) on 3' end

<400> SEQUENCE: 11
ctgaagatgg tttac                                                      15

<210> SEQ ID NO 12
<211> LENGTH: 15
<212> TYPE: DNA
<213> ORGANISM: Artificial Sequence
<220> FEATURE:
<223> OTHER INFORMATION: Synthetic: Synthetic PNA conjugate
<220> FEATURE:
<221> NAME/KEY: modified_base
<222> LOCATION: (1)..(1)
<223> OTHER INFORMATION: Alexa488-O on 5' end
<220> FEATURE:
<221> NAME/KEY: modified_base
<222> LOCATION: (15)..(15)
<223> OTHER INFORMATION: Lys(C6SH) on 3' end

<400> SEQUENCE: 12
catcctgccg ctatg                                                      15

<210> SEQ ID NO 13
<211> LENGTH: 15
<212> TYPE: DNA
<213> ORGANISM: Artificial Sequence
<220> FEATURE:
<223> OTHER INFORMATION: Synthetic: Synthetic PNA conjugate
<220> FEATURE:
<221> NAME/KEY: modified_base
<222> LOCATION: (1)..(1)
<223> OTHER INFORMATION: Biotin-O on 5' end
<220> FEATURE:
<221> NAME/KEY: modified_base
<222> LOCATION: (15)..(15)
<223> OTHER INFORMATION: Arg-O-Cys on 3' end

<400> SEQUENCE: 13
gtcaaccatc ttcag                                                      15

<210> SEQ ID NO 14
<211> LENGTH: 15
<212> TYPE: DNA
<213> ORGANISM: Artificial Sequence
<220> FEATURE:
<223> OTHER INFORMATION: Synthetic: Synthetic PNA conjugate
<220> FEATURE:
<221> NAME/KEY: modified_base
<222> LOCATION: (1)..(1)
<223> OTHER INFORMATION: Biotin-O on 5' end
<220> FEATURE:
<221> NAME/KEY: modified_base
<222> LOCATION: (15)..(15)
<223> OTHER INFORMATION: Lys(eg3-N3) on 3' end

<400> SEQUENCE: 14
gtcaaccatc ttcag                                                      15
```

```
<210> SEQ ID NO 15
<211> LENGTH: 15
<212> TYPE: DNA
<213> ORGANISM: Artificial Sequence
<220> FEATURE:
<223> OTHER INFORMATION: Synthetic: Synthetic PNA conjugate
<220> FEATURE:
<221> NAME/KEY: modified_base
<222> LOCATION: (1)..(1)
<223> OTHER INFORMATION: Biotin-O on 5' end
<220> FEATURE:
<221> NAME/KEY: modified_base
<222> LOCATION: (15)..(15)
<223> OTHER INFORMATION: Lys(SMCC) on 3' end

<400> SEQUENCE: 15
gtcaaccatc ttcag                                                15

<210> SEQ ID NO 16
<211> LENGTH: 15
<212> TYPE: DNA
<213> ORGANISM: Artificial Sequence
<220> FEATURE:
<223> OTHER INFORMATION: Synthetic: Synthetic DNA conjugate
<220> FEATURE:
<221> NAME/KEY: modified_base
<222> LOCATION: (15)..(15)
<223> OTHER INFORMATION: Rhodamine on 3' end

<400> SEQUENCE: 16
ctgaagatgg ttgac                                                15

<210> SEQ ID NO 17
<211> LENGTH: 15
<212> TYPE: DNA
<213> ORGANISM: Artificial Sequence
<220> FEATURE:
<223> OTHER INFORMATION: Synthetic: Synthetic DNA conjugate
<220> FEATURE:
<221> NAME/KEY: modified_base
<222> LOCATION: (1)..(1)
<223> OTHER INFORMATION: FAM on 5' end

<400> SEQUENCE: 17
ctgaagatgg ttgac                                                15

<210> SEQ ID NO 18
<211> LENGTH: 15
<212> TYPE: DNA
<213> ORGANISM: Artificial Sequence
<220> FEATURE:
<223> OTHER INFORMATION: Synthetic: Synthetic DNA conjugate
<220> FEATURE:
<221> NAME/KEY: modified_base
<222> LOCATION: (15)..(15)
<223> OTHER INFORMATION: DIG on 3' end

<400> SEQUENCE: 18
ctgaagatgg ttgac                                                15

<210> SEQ ID NO 19
<211> LENGTH: 10
<212> TYPE: DNA
<213> ORGANISM: Artificial Sequence
<220> FEATURE:
<223> OTHER INFORMATION: Synthetic: Synthetic PNA conjugate
<220> FEATURE:
<221> NAME/KEY: modified_base
<222> LOCATION: (1)..(1)
```

```
<223> OTHER INFORMATION: Biotin-O on 5' end
<220> FEATURE:
<221> NAME/KEY: modified_base
<222> LOCATION: (10)..(10)
<223> OTHER INFORMATION: MAL on 3' end

<400> SEQUENCE: 19
ccatcttcag                                                                  10

<210> SEQ ID NO 20
<211> LENGTH: 10
<212> TYPE: DNA
<213> ORGANISM: Artificial Sequence
<220> FEATURE:
<223> OTHER INFORMATION: Synthetic: Synthetic PNA conjugate
<220> FEATURE:
<221> NAME/KEY: modified_base
<222> LOCATION: (1)..(1)
<223> OTHER INFORMATION: Biotin-O on 5' end
<220> FEATURE:
<221> NAME/KEY: modified_base
<222> LOCATION: (10)..(10)
<223> OTHER INFORMATION: Lys(SMCC) on 3' end

<400> SEQUENCE: 20
ttagtccaac                                                                  10

<210> SEQ ID NO 21
<211> LENGTH: 10
<212> TYPE: DNA
<213> ORGANISM: Artificial Sequence
<220> FEATURE:
<223> OTHER INFORMATION: Synthetic: Synthetic PNA conjugate
<220> FEATURE:
<221> NAME/KEY: modified_base
<222> LOCATION: (1)..(1)
<223> OTHER INFORMATION: Biotin-O on 5' end
<220> FEATURE:
<221> NAME/KEY: modified_base
<222> LOCATION: (10)..(10)
<223> OTHER INFORMATION: Lys(C6SH) on 3' end

<400> SEQUENCE: 21
ccatcttcag                                                                  10

<210> SEQ ID NO 22
<211> LENGTH: 15
<212> TYPE: DNA
<213> ORGANISM: Artificial Sequence
<220> FEATURE:
<223> OTHER INFORMATION: Synthetic: Synthetic PNA conjugate
<220> FEATURE:
<221> NAME/KEY: modified_base
<222> LOCATION: (1)..(1)
<223> OTHER INFORMATION: Biotin-O on 5' end
<220> FEATURE:
<221> NAME/KEY: modified_base
<222> LOCATION: (15)..(15)
<223> OTHER INFORMATION: PC-Lys(C6H) on 3' end

<400> SEQUENCE: 22
cattcaaatc cccga                                                            15
```